(12) United States Patent
Yu et al.

(10) Patent No.: US 10,597,447 B2
(45) Date of Patent: Mar. 24, 2020

(54) COMPOSITIONS COMPRISING PURIFIED RECOMBINANT IL-13 ANTIBODY

(71) Applicant: Genentech, Inc., South San Francisco, CA (US)

(72) Inventors: X. Christopher Yu, Piedmont, CA (US); Susan C. Fisher, San Carlos, CA (US); Ailen M. Sanchez, Foster City, CA (US); Martin Vanderlaan, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 58 days.

(21) Appl. No.: 15/902,139

(22) Filed: Feb. 22, 2018

(65) Prior Publication Data

US 2018/0291094 A1 Oct. 11, 2018

Related U.S. Application Data

(60) Division of application No. 15/065,693, filed on Mar. 9, 2016, now Pat. No. 9,920,120, which is a continuation of application No. PCT/US2014/055387, filed on Sep. 12, 2014.

(60) Provisional application No. 61/877,517, filed on Sep. 13, 2013.

(51) Int. Cl.
| | |
|---|---|
| *C07K 16/24* | (2006.01) |
| *C07K 16/06* | (2006.01) |
| *C07K 16/08* | (2006.01) |
| *C07K 16/40* | (2006.01) |
| *C07K 1/18* | (2006.01) |
| *C07K 1/22* | (2006.01) |
| *C07K 1/36* | (2006.01) |
| *C07K 16/18* | (2006.01) |
| *A61K 39/00* | (2006.01) |

(52) U.S. Cl.
CPC .............. *C07K 16/244* (2013.01); *C07K 1/18* (2013.01); *C07K 1/22* (2013.01); *C07K 1/36* (2013.01); *C07K 16/065* (2013.01); *C07K 16/088* (2013.01); *C07K 16/18* (2013.01); *C07K 16/40* (2013.01); *A61K 2039/505* (2013.01); *C07K 2317/14* (2013.01); *C07K 2317/24* (2013.01); *C07K 2317/51* (2013.01); *C07K 2317/515* (2013.01); *C07K 2317/56* (2013.01); *C07K 2317/565* (2013.01)

(58) Field of Classification Search
CPC .................................................. C07K 16/244
See application file for complete search history.

(56) References Cited

U.S. PATENT DOCUMENTS

| | | |
|---|---|---|
| 3,645,090 A | 2/1972 | Mochizuki et al. |
| 3,691,016 A | 9/1972 | Patel |
| 3,940,475 A | 2/1976 | Gross |
| 3,969,287 A | 7/1976 | Jaworek et al. |
| 4,195,128 A | 3/1980 | Hildebrand et al. |
| 4,229,537 A | 10/1980 | Hodgins et al. |
| 4,247,642 A | 1/1981 | Hirohara et al. |
| 4,330,440 A | 5/1982 | Ayers et al. |
| 4,376,110 A | 3/1983 | David et al. |
| 4,737,456 A | 4/1988 | Weng et al. |
| 4,816,567 A | 3/1989 | Cabilly et al. |
| 5,011,778 A | 4/1991 | Newman et al. |
| 5,229,275 A | 7/1993 | Goroff |
| 5,359,037 A | 10/1994 | Wallach et al. |
| 5,534,615 A | 7/1996 | Baker et al. |
| 5,545,807 A | 8/1996 | Surani et al. |
| 5,550,045 A | 8/1996 | Musters et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,596,072 A | 1/1997 | Culpepper et al. |
| 5,641,870 A | 6/1997 | Rinderknecht et al. |
| 5,652,123 A | 7/1997 | Caput et al. |
| 5,677,165 A | 10/1997 | De Boer et al. |
| 5,693,780 A | 12/1997 | Newman et al. |
| 5,705,154 A | 1/1998 | Dalie et al. |
| 5,710,023 A | 1/1998 | Collins et al. |
| 5,717,072 A | 2/1998 | Mosley et al. |
| 5,747,037 A | 5/1998 | Noelle et al. |
| 5,783,181 A | 7/1998 | Browne et al. |
| 5,928,915 A | 7/1999 | Warner et al. |
| 5,965,709 A | 10/1999 | Presta et al. |
| 5,994,514 A | 11/1999 | Jardieu et al. |

(Continued)

FOREIGN PATENT DOCUMENTS

| | | |
|---|---|---|
| CN | 101472947 | 7/2009 |
| CN | 101979404 A | 2/2011 |

(Continued)

OTHER PUBLICATIONS

"Monoclonal Anti-Human IL 13 Antibody," R&D Systems, Inc. Catalog [On-line], Oct. 2002 [retrieved on Oct. 14, 2002], Retrieved from the Internet: <URL: http://www.rndsystems.com/asp/c_search.asp?ucategory=3&factors=IL%2D13>.

(Continued)

*Primary Examiner* — Prema M Mertz

(74) *Attorney, Agent, or Firm* — McNeill Baur PLLC

(57) ABSTRACT

Purified recombinant polypeptides isolated from Chinese hamster ovary host cells, including antibodies, such as therapeutic antibodies, and methods of making and using such polypeptides are provided.

36 Claims, 3 Drawing Sheets

Specification includes a Sequence Listing.

(56) References Cited

U.S. PATENT DOCUMENTS

| | | |
|---|---|---|
| 6,037,453 A | 3/2000 | Jardieu et al. |
| 6,127,526 A | 10/2000 | Blank |
| 6,143,871 A | 11/2000 | Bonnefoy et al. |
| 6,156,321 A | 12/2000 | Thorpe et al. |
| 6,299,875 B1 | 10/2001 | Caplan et al. |
| 6,329,509 B1 | 12/2001 | Jardieu et al. |
| 6,333,398 B1 | 12/2001 | Blank |
| 6,468,528 B1 | 10/2002 | Mak et al. |
| 6,518,061 B1 | 2/2003 | Puri et al. |
| 6,576,232 B1 | 6/2003 | Debinski et al. |
| 6,664,227 B1 | 12/2003 | Wynn et al. |
| 6,743,604 B1 | 6/2004 | Bonnefoy et al. |
| 6,870,034 B2 | 3/2005 | Breece et al. |
| 6,911,530 B1 | 6/2005 | Willson et al. |
| 7,026,139 B2 | 4/2006 | Yang |
| 7,078,494 B1 | 7/2006 | Collins et al. |
| 7,078,496 B2 | 7/2006 | Roberts et al. |
| 7,157,276 B2 | 1/2007 | Pham |
| 7,312,024 B2 | 12/2007 | Mak et al. |
| 7,323,553 B2 | 1/2008 | Fahrner et al. |
| 7,501,121 B2 | 3/2009 | Tchistiakova et al. |
| 7,553,487 B2 | 6/2009 | Collins et al. |
| 7,615,213 B2 | 11/2009 | Kasaian et al. |
| 7,674,459 B2 | 3/2010 | Fung et al. |
| 7,759,117 B2 | 7/2010 | Pham |
| 7,863,426 B2 | 1/2011 | Wan et al. |
| 8,067,182 B2 | 11/2011 | Kelley et al. |
| 8,067,199 B2 | 11/2011 | Fung et al. |
| 8,088,618 B2 | 1/2012 | Fung et al. |
| 8,137,561 B2 | 3/2012 | Kozlov et al. |
| 8,318,160 B2 | 11/2012 | Fung et al. |
| 8,383,350 B1 | 2/2013 | Kolz et al. |
| 8,435,406 B2 | 5/2013 | Kozlov et al. |
| 8,449,885 B2 | 5/2013 | Meng et al. |
| 8,491,904 B2 | 7/2013 | Hickman |
| 8,715,669 B2 | 5/2014 | Masternak et al. |
| 9,605,065 B2 | 3/2017 | Fung et al. |
| 2003/0049257 A1 | 3/2003 | Mak et al. |
| 2003/0235555 A1 | 12/2003 | Shealey et al. |
| 2004/0242851 A1 | 12/2004 | Zhu |
| 2005/0032175 A1 | 2/2005 | Stahl et al. |
| 2005/0037333 A1 | 2/2005 | Pham |
| 2005/0226883 A1 | 10/2005 | Averback et al. |
| 2005/0277126 A1 | 12/2005 | Collins et al. |
| 2006/0073148 A1 | 4/2006 | Tchistiakova et al. |
| 2006/0194280 A1 | 8/2006 | Dillon et al. |
| 2006/0292643 A1 | 12/2006 | Goletz et al. |
| 2007/0037966 A1 | 2/2007 | Rasmussen et al. |
| 2007/0218516 A1 | 9/2007 | Palys et al. |
| 2007/0292442 A1 | 12/2007 | Wan et al. |
| 2008/0008648 A1 | 1/2008 | Fung et al. |
| 2008/0207497 A1 | 8/2008 | Ramakrishna et al. |
| 2008/0261249 A1 | 10/2008 | Wang et al. |
| 2009/0214523 A1 | 8/2009 | Fung et al. |
| 2009/0324604 A1 | 12/2009 | Liu et al. |
| 2010/0041039 A1 | 2/2010 | Harvey |
| 2010/0055103 A1 | 3/2010 | Chen et al. |
| 2010/0135987 A1 | 6/2010 | Hickman et al. |
| 2010/0150864 A1 | 6/2010 | Hickman et al. |
| 2010/0266494 A1 | 10/2010 | Fung et al. |
| 2011/0014199 A1 | 1/2011 | Fung et al. |
| 2011/0038877 A1 | 2/2011 | Way et al. |
| 2011/0093965 A1 | 4/2011 | O'Donoghue et al. |
| 2011/0123530 A1 | 5/2011 | Arron et al. |
| 2011/0256144 A1 | 10/2011 | Okano et al. |
| 2012/0027773 A1 | 2/2012 | Whalen et al. |
| 2012/0156194 A1 | 6/2012 | Arron et al. |
| 2012/0156203 A1 | 6/2012 | Fung et al. |
| 2012/0189639 A1 | 7/2012 | Schebye et al. |
| 2012/0210467 A1 | 8/2012 | Barton et al. |
| 2012/0214971 A1 | 8/2012 | Fung et al. |
| 2012/0294796 A1 | 11/2012 | Johnson et al. |
| 2012/0328624 A1 | 12/2012 | Yoshida et al. |
| 2013/0030159 A1 | 1/2013 | Han et al. |
| 2013/0089872 A1 | 4/2013 | Nakamura et al. |
| 2013/0142786 A1 | 6/2013 | Liu et al. |
| 2013/0224210 A1 | 8/2013 | Adamkewicz et al. |
| 2014/0105897 A1 | 4/2014 | Fung et al. |

FOREIGN PATENT DOCUMENTS

| | | |
|---|---|---|
| EP | 0 404 097 B1 | 6/1990 |
| EP | 0 164 656 B1 | 9/1990 |
| EP | 1 270 595 B1 | 1/2003 |
| EP | 0 876 482 B1 | 3/2003 |
| EP | 1 327 681 A1 | 7/2003 |
| EP | 1 141 286 B1 | 10/2006 |
| JP | H0799971 | 4/1995 |
| WO | 89/04838 A1 | 6/1989 |
| WO | 91/09059 A1 | 6/1991 |
| WO | 93/11161 A1 | 6/1993 |
| WO | 93/15766 | 8/1993 |
| WO | 93/16185 A2 | 8/1993 |
| WO | 93/16185 A3 | 8/1993 |
| WO | 94/04680 A1 | 3/1994 |
| WO | 94/11026 A2 | 5/1994 |
| WO | 94/14975 A1 | 7/1994 |
| WO | 95/14780 A2 | 6/1995 |
| WO | 95/22389 | 8/1995 |
| WO | 97/15663 A1 | 5/1997 |
| WO | 97/20926 | 6/1997 |
| WO | 97/29131 | 8/1997 |
| WO | 97/31946 | 9/1997 |
| WO | 97/47742 | 12/1997 |
| WO | 98/10638 A1 | 3/1998 |
| WO | 98/30240 | 7/1998 |
| WO | 00/15663 | 3/2000 |
| WO | 00/23410 | 4/2000 |
| WO | 00/29004 A1 | 5/2000 |
| WO | 00/36103 | 6/2000 |
| WO | 00/44407 A2 | 8/2000 |
| WO | 01/34645 A2 | 5/2001 |
| WO | 01/92514 A1 | 6/2001 |
| WO | 2001/062801 | 8/2001 |
| WO | 02/051870 A2 | 7/2002 |
| WO | 02/051870 A3 | 7/2002 |
| WO | 02/055100 A2 | 7/2002 |
| WO | 03/035694 A2 | 5/2003 |
| WO | 03/035694 A3 | 5/2003 |
| WO | 03/035847 A2 | 5/2003 |
| WO | 03/040164 A2 | 5/2003 |
| WO | 03/018635 A1 | 6/2003 |
| WO | 03/086451 A1 | 10/2003 |
| WO | 2004/001655 A1 | 12/2003 |
| WO | 2004/019974 A2 | 3/2004 |
| WO | 2004/019975 A2 | 3/2004 |
| WO | 2004/019979 A2 | 3/2004 |
| WO | 2004/071408 | 8/2004 |
| WO | 2005/007699 A2 | 1/2005 |
| WO | 2005/007699 A3 | 1/2005 |
| WO | 2005/007699 A8 | 1/2005 |
| WO | 2005/035572 A2 | 4/2005 |
| WO | 2005/035572 A3 | 4/2005 |
| WO | 2005/062967 A2 | 7/2005 |
| WO | 2005/062967 A3 | 7/2005 |
| WO | 2005/062972 A2 | 7/2005 |
| WO | 2005/121177 A2 | 12/2005 |
| WO | 2005/123126 A2 | 12/2005 |
| WO | 2006/003407 A2 | 1/2006 |
| WO | 2006/085938 A2 | 7/2006 |
| WO | 2006/085938 A3 | 7/2006 |
| WO | 2006/099308 A2 | 9/2006 |
| WO | 2006/110277 | 10/2006 |
| WO | 2007/064972 | 2/2007 |
| WO | 2007/036745 A2 | 4/2007 |
| WO | 2007/036745 A3 | 4/2007 |
| WO | 2007/045477 A2 | 4/2007 |
| WO | 2007/045477 A3 | 4/2007 |
| WO | 2007/045477 A8 | 4/2007 |
| WO | 2007/068412 | 6/2007 |
| WO | 2007/068429 A1 | 6/2007 |
| WO | 2007/124143 | 11/2007 |
| WO | 2008/011348 A2 | 1/2008 |
| WO | 2008/011348 A3 | 1/2008 |

(56) References Cited

FOREIGN PATENT DOCUMENTS

| | | |
|---|---|---|
| WO | 2008/060364 | 5/2008 |
| WO | 2008/086395 A2 | 7/2008 |
| WO | 2008/086395 A3 | 7/2008 |
| WO | 2008/140455 A1 | 11/2008 |
| WO | 2008/156621 | 12/2008 |
| WO | 2008/156622 | 12/2008 |
| WO | 2009/048537 | 4/2009 |
| WO | 2009/048538 | 4/2009 |
| WO | 2009/048539 | 4/2009 |
| WO | 2009/124090 A1 | 10/2009 |
| WO | 2009/131643 A1 | 10/2009 |
| WO | 2009/136286 | 11/2009 |
| WO | 2010/041037 A2 | 4/2010 |
| WO | 2010/048190 | 4/2010 |
| WO | 2010/048192 | 4/2010 |
| WO | 2010/073119 A1 | 7/2010 |
| WO | 2011/031397 A1 | 3/2011 |
| WO | 2011/050071 A2 | 4/2011 |
| WO | 2011109400 | 9/2011 |
| WO | 2011/150110 | 12/2011 |
| WO | 2012/016173 | 2/2012 |
| WO | 2012/047732 A2 | 4/2012 |
| WO | 2012/075037 A1 | 6/2012 |
| WO | 2012/083132 | 6/2012 |
| WO | 2012/145493 A1 | 10/2012 |
| WO | 2013/66707 A1 | 5/2013 |
| WO | 2013/066866 A1 | 5/2013 |
| WO | 2015/038884 A2 | 3/2015 |

OTHER PUBLICATIONS

"Hamster putative phospholipase B-like 2 (PLBD2) ELISA kit" CUSABIO (Catalog No. CSB-EL018125HA).

Abbas et al., Cell Molec Immunol (W.B. Saunders Co., Philadelphia, PA, p. 54), (1991).

Ahlers et al., "A push-pull approach to maximize vaccine efficacy: Abrogating suppression with an IL-13 inhibitor while augmenting help with granulocyte/macrophage colony-stimulating factor and CD40L" Proc Nat Acad Sci USA 99(20):13020-13025 (Oct. 1, 2002).

Akbari et al., "Essential role of NKT cells producing IL-4 and IL-13 in the development of allergen-induced airway hyperreactivity" Nature Medicine 9(5):582-588 (2003).

Alberts et al. Molec Biol Cell "The Immune System" 3RD edition, New York & London:Garland Publishing, Inc.,(Suppl Ch 23):1208-1209 (1994).

Amrad Corporation, Ltd., "Project: IL-13 receptor antibody," pp. 1-2, Aug. 17, 2005.

Andrews et al., "Kinetic analysis of the interleukin-13 receptor complex" J Biol Chem 277(48):46073-46078 (Nov. 29, 2002).

Anicetti et al., "Immunoassay for the detection of E. coli proteins in recombinant DNA derived human growth hormone" J Immunol Methods 91(2):213-224 (1986).

Arima et al., "Characterization of the interaction between interleukin-13 and interleukin-13 receptors" J Biol Chem 280(26):24915-24922 (Jul. 1, 2005).

Arima et al., "Upregulation of IL-13 concentration in vivo by the IL13 variant associated with bronchial asthma." J Allergy Clin Immunol 109(6):980-987 (2002).

Asthma and Allergy Foundation of America and The national Pharmaceutical Council, "A closer look at asthma" pp. 1-6.

Becker et al., "Unraveling the chinese hamster ovary cell line transcriptome by next-generation sequencing" J Biotechnol 156:227-235 (2011).

Bellanti, JA, "Cytokines and allergic diseases: clinical aspects" Allergy Asthma Proc ((Abstract only)), 19(6):337-341 (1998).

Blanchard et al., "Inhibition of human interleukin-13-induced respiratory and oesophageal inflammation by anti-human-interleukin-13 antibody (CAT-354)" Clin Exp Allergy 35:1096-1103 (2005).

Blattner et al., "The complete genome sequence of *Escherichia coli* K-12." Science 277:1453-1462 (Sep. 1997).

Blease et al., "Therapeutic effect of IL-13 immunoneutralization during chronic experimental fungal asthma" J Immuinol 165:5219-5224 (2001).

Bomans et al., "Identification and monitoring of host cell proteins by mass spectrometry combined with high performance immunochemistry testing" PLoS One 8(11):e81639 (2013).

Bosmann et al., "Detection of serum free light chains: the problem with antigen excess" Clin Chem Lab Med 48(10):1419-1422 (2010).

Bost et al., "In vivo treatment with anti-interleukin-13 antibodies significantly reduces the humoral immune response against an oral immunogen in mice" Immunology 87(4):633-641 (1996).

Bree et al., "IL-13 blockade reduces lung inflammation after Ascaris suum challenge in cynomolgus monkeys" J Allergy Clin Immunol 119:1251-1257 (2007).

Brennan et al., "Preparation of bispecific antibodies by chemical recombination of monoclonal immunoglobulin $G_1$ fragments" Science 229:81-83 (1985).

Brewer et al., "Inhibition of key cytokines by tetrathiomolybdate in the bleomycin model of pulmonary fibrosis" J Inorg Biochem 98:2160-2167 (2004).

Brinkmann et al., "TCR-stimulated naive human $CD4^+45R0^-$ T cells develop into effector cells that secrete IL-13, IL-5, and IFN-y, but no IL-4, and help efficient IgR production by B cells" J Immunol 154(7):3078-3087 (1995).

Brinks et al., "Immunogenicity of therapeutic proteins: the use of animal models" Pharm Res 28:2379-2385 (2011).

Brodeur et al., "Mouse-human myeloma partners for the production of heterohybridomas" Monoclonal Antibody Production Techniques and Applications, (New York: Marcel Dekker, Inc.),:51-63 (1987).

Brodsky et al., "Caprylic acid precipitation method for impurity reduction: An alternative to conventional chromatography for monoclonal antibody purification" Biotechnol Bioeng 109(10):2589-2598 (Oct. 2012).

Brown et al., "A family of small inducible proteins secreted by leukocytes are members of a new superfamily that includes leukocyte and fibroblast-derived inflammatory agents, growth factors, and indicators of various activation processes" J Immunol 142(2):679-687 (Jan. 15, 1989).

Bruggermann et al., "Designer mice: The production of human antibody repertoires in transgenic animals" Year Immun 7:33-40 (1993).

Caldas et al., "Humanization of the anti-CD18 antibody 6.7: an unexpected effect of a framework residue in binding to antigen" Mol Immunol 39:941-952 (2003).

Campbell et al., "Allergic humans are hyporesponsive to a CXCR3 ligand-mediated Th1 immunity-promoting loop" FASEB J 18(2):329-331 (2003).

Caput et al., "Clining and characterization of a specific interleukin (IL)-13 binding protein structurally related to the IL-5 receptor α chain" J Biol Chem 271(28):16921-16926 (Jul. 12, 1996).

Carbadillo et al., "IL-4 induces human B cell maturation and IgE synthesis in SCID-hu mice" J Immunol 155(9):4162-4170 (1995).

Carrington, "BIAcore analysis of hIL-13Ra2 binding/blocking to hIL-13 pre-bound to antibody JES10-5A2 or antibody 213" UCB Celltech:1-3 (Jun. 7, 2007).

Carter et al., "High level *Escherichia coli* expression and production of a bivalent humanized antibody fragment" Bio/Technology 10(2):163-167 (Feb. 1992).

Carter et al., "Humanization of an anti-p185$^{HER2}$ antibody for human cancer therapy" P Natl Acad Sci USA 89:4285-4289 (May 1992).

Casolaro et al., "Biology and genetics of atopic disease" Curr Opin Immunol 8:796-803 (1996).

Casset et al., "A peptide mimetic of an anti-CD4 monoclonal antibody by rational design" Biochem Bioph Res Co 307(1):198-205 (Jul. 18, 2003).

Champion et al., "The challenges of monitoring host cell protein impurities," CMC Strategy Forum, Jul. 19-20, 2004.

(56) References Cited

OTHER PUBLICATIONS

Champion et al., "Defining your product profile and maintaining control over it, Part 2, Challenges of monitoring host cell protein impurities" Bioproc Int:52-57 (Sep. 2005).
Champion et al., "Similarity of the *Escherichia coli* proteome upon completion of different biopharmaceutical fermentation processes" Proteomics 1:1133-1148 ( 2001).
Chen et al., "Quantitation of *E. coli* protein impurities in recombinant human interferon-γ" Applied Biochem Biotechnol 36:137-152 ( 1992).
Chen, A., "Development and validation of immunoassays for host cell proteins in recombinant DNA-derived protein pharmaceuticals" J Biotechnology Healthcare 3(1):70-80 ( 1996).
Chien et al., "Significant structural and functional change of an antigen-binding site by a distant amino acid substitution: Proposal of a structural mechanism" P Natl Acad Sci USA 86:5532-5536 (Jul. 1989).
Chothia et al., "Canonical structures for the hypervariable regions of immunoglobulins" J Mol Biol 196:901-917 ( 1987).
Clackson et al., "Making antibody fragments using phage display libraries" Nature 352(6336):624-628 (Aug. 15, 1991).
Cohn et al. et al., "Induction of Airway Mucus Production By T Helper 2 (Th2) Cells: A Critical Role for Interleukin 4 In Cell Recruitment But Not Mucus Production" J Exp Med 186(10):1737-1747 (Nov. 17, 1997).
Cohn et al., "Cutting Edge: IL-4-independent induction of airway hyperresponsiveness by Th2, but not Th1, cells" J Immunol 161:3813-3816 ( 1998).
Corren et al., "Lebrikizumab treatment in adults with asthma" N Engl J Med 365(12):1088-1098 (Sep. 22, 2011).
Coutinho et al., "Mannose-6-phosphate pathway: a review on its role in lysosomal function and dysfunction" Molec Genetics Metabolism 105:542-550 ( 2012).
Cunningham and Wells, "High-resolution epitope mapping of hGH-receptor interactions by alanine-scanning mutagenesis" Science 24:1081-1085 (Jun. 2, 1989).
Daniels et al., "Imatinib mesylate inhibits the profibrogenic activity of TGF-β and prevents bleomycin-mediated lung fibrosis" J Clin Invest 114(9):1308-1316 ( 2004).
Daval et al., "Risk of antigen excess in serum free light chain measurements" Clin Chem 53:1985-1986 ( 2007).
David and Reisfeld, "Protein Iodination with Solid State Lactoperoxidase" Biochemistry-US 13(5):1014-1021 (Feb. 26, 1974).
Davies et al., "'Camelising' human antibody fragments: NMR studies on VH domains" FEBS Lett 330:285-290 ( 1994).
De Pascalis et al., "Grafting of 'abbreviated' complementarity-determining regions containing specificity-determining residues essential for ligand contact to engineer a less immunogenic humanized monoclonal antibody" J Immunol 169:3076-3084 ( 2002).
De Swart et al., "Immunization of Macaques with formalin-inactivated respiratory syncytial virus (RSV) induces interleukin-13-associated hypersensitivity to subsequent RSV infection" J Virol 76(22):11561-11569 ( 2002).
De Vries et al., "Modulation of the human IgE response" Eur Respir J (Suppl. 9( Suppl 22):58s-62s ( 2002).
De Vries, J. E., "Novel fundamental approaches to intervening in IgE-mediated allergic diseases" J Invest Dermatol 102:141-144 ( 1994).
Debinski et al., "A novel chimeric protein composed of interleukin 13 and pseudomonas exotoxin is highly cytotoxic to human carcinoma cells expressing receptors for interleukin 13 and interleukin 4" J Biol Chem 270(28):16775-16780 ( 1995).
Debinski et al., "Human glioma cells overexpress receptors for interleukin 13 and are extremely sensitive to a novel chimeric protein composed of interleukin 13 and pseudomonas exotoxin" Clin Cancer Res 1:1253-1258 ( 1995).
Deuschl et al., "Molecular characterization of the hypothetical 66.3-kDa protein in mouse: lysosomal targeting, glycosylation, processing and tissue distribution" FEBS Lett 580:5747-5752 ( 2006).

Donaldson et al., "The murine IL-13 receptor α2: Molecular cloning, characterization, and comparison with murine IL-13 receptor α1" J Immunol 161:2317-2324 ( 1998).
Doneaunu et al., "Analysis of host-cell proteins in biotherapeutic proteins by comprehensive online two-dimensional liquid chromatography/mass spectrometry" mAbs (10.4161/mabs.4.1.18748), 4:1, 24-44 ( 2012).
Dooley and Flajnik, "Antibody repertoire development in cartilaginous fish" Developmental and Comparative Immunol 30:43-56 ( 2006).
Dorland's Illustrated Medical Dictionary 28th edition, Philadelphia:W. B. Saundres,:151 ( 1994).
Doucet et al., "Interleukin (IL)4 and IL-13 act on human lung fibroblasts, Implication in Asthma" J Clin Invest 101:2129-2139 ( 1998).
Eaton, L., "Host cell contaminant protein assay development for recombinant biopharmaceuticals" J Chromatogr A 705(1):105-114 (Jun. 23, 1995).
Economides et al., "Designer cytokines: Targeting actions to cells of choice" Science 270:1351-1353 ( 1995).
Encyclopedia Britannica's Guide to the Nobel Prizes, "Immune system disorders" [on-line], Jun. 27, 2007 [retrieved on Jun. 27, 2007], pp. 1-4, Retrieved from the Internet:<URL: http://www.britannica.com/nobelprize/article-215507>.
Enomoto et al., "High-throughput miniaturized immunoassay for human interleukin-13 secreted from NK3.3 cells using homogenous time-resolved fluorescence" J Pharm Biomed Analysis 28:73-79 ( 2002).
European Supplemental Search Report EP 14 84 4121, dated Feb. 20, 2017, pp. 1-5.
Fauci et al. Harrison's Principles of Internal Medicine "Asthma" 14th edition,McGraw-Hill,:1419-1420, 1760-1761 ( 1998).
Fichtner-Feigl et al., "IL-13 signaling through the IL-12α$_2$ receptor is involved in induction of TGF-β$_1$ production and fibrosis" Nat Med 12(1):99-106 (Jan. 2006).
Flatman et al., "Process analytics for purification of monoclonal antibodies" J Chromatography 848:79-87 ( 2007).
Gabrielsson et al., "Increased frequencies of allergen-induced interleukin-13-producing cells in atopic individuals during the pollen season" Scand J Immunol 48:429-435 ( 1998).
Gagnon, "Monoclonal antibody purification with hydroxyapatite" New Biotechnol 25(5):287-293 (Jun. 2009).
Gao et al., "Fragmentation of a highly purified monoclonal antibody attributed to residual CHO cell protease activity" Biotechnol Bioeng 108(4):977-982 (Apr. 2011).
Gauvreau et al., "Effects of interleukin-13 blockade on allergen-induced airway responses in mild atopic asthma." Am J Respir Crit Care Med 183:1007-1014 ( 2011).
GE Healthcare Life Sciences, Data file 11-0011-65 AC, "MabSelect SuRe".
Genebank Accession No. NP 002179 (Apr. 7, 2003) Interleukin 13 Precursor (*Homo sapiens*), 2 pages, http://www.ncbi.nlm.nih.gov/protein/26787978?sat=24&satkey=4532247.
George et al., "Differential effects of anti-β$_2$-glycoprotein I antibodies on endothelial cells and on the manifestations of experimental antiphospholipid syndrome" Circulation 97:900-906 ( 1998).
Ghaderi et al., "Implications of the presence of N-glycolylneuraminic acid in recombinant therapeutic glycoproteins" Nature Biotechnol 28(8):863-869 (Aug. 2010).
Ghaffar et al., "IL-13 mRNA and Immunoreactivity in Allergen-induced rhinitis: Comparison with IL-4 expression and modulation by topical glucocorticoid therapy" Am J Respir Cell Mol Biol 17:17-324 ( 1997).
Ghamdi et al., "IL-4 and IL-13 expression in chronic sinusitis: relationship with cellular infiltrate and effect of topical corticosteroid treatment" J Otolaryngology 26(3):160-166 ( 1997).
Ghose et al., Sep./Oct. 2013, mAbs, 5:5, pp. 795-800.f.
Giusti et al., "Somatic Diversification of S107 from an Antiphosphocholine to an anti-DNA Autoantibody is Due to a Single Base Change in its Heavy Chain Variable Region" P Natl Acad Sci USA 84:2926-2930 (May 1987).

(56) References Cited

OTHER PUBLICATIONS

Goding, Monoclonal Antibodies: Principles and Practice "Production and Application of Monoclonal Antibodies in Cell Biology, Biochemistry and Immunology" Academic Press,:56-103 ( 1986).
Grampp et al., "Managing unexpected events in the manufacturing of biologic medicines," Biodrugs DOI 10.1007/s40259-013-0018-5 Published online on Mar. 26, 2013.
Griffiths et al., "Human anti-self antibodies with high specificity from phage display libraries" EMBO J 12(2):725-734 ( 1993).
Grunig et al., "Requirement of IL-13 independently of IL-4 in experimental asthma" Science 282:2261-2263 (Dec. 18, 1998).
Gussow et al., "Humanization of Monoclonal Antibodies" Meth Enzymol 203:99-121 ( 1991).
Haggerty, "Hamster MCP-1: Potential Culprit of Clinical Adverse Events" Slides CRL Biotechnology.Symposium, pp. 1-26 (Sep. 2014).
Hamid et al., "In vivo expression of IL-12 and IL-13 in atopic dermatitis" J Allergy Clin Immunol 98:225-231 ( 1996).
Hanania et al., "Lebrikizumab in moderate-to-severe asthma: pooled data from two randomised placebo-controlled studies" Thorax 70:748-756 ( 2015).
Hasegawa et al., "Serum levels of tumor necrosis factor and interleukin-13 are elevated in patients with localized scleroderma" Dermatology 207:141-147 ( 2003).
Heller et al., "Interleukin-13 is the key effector Th2 cytokine in ulcerative colitis that affects epithelial tight junctions, apoptosis, and cell restitution" Gastroenterology 129:550-564 ( 2005).
Heller et al., "Oxazolone colitis, a Th2 colitis model resembling ulcerative colitis, is mediated by IL-13-producing NK-T cells" Immunity 17:629-638 ( 2002).
Hershey et al., "IL-13 receptors and signaling pathways: an evolving web" J Allergy Clin Immunol 111(4):677-690 (Apr. 2003).
Hoffman, "Strategies for Host Cell Protein Analysis" Biopharm 13:38-45 ( 2000).
Hogwood et al., "Host cell protein dynamics in recombinant CHO cells" Bioengineered 4(5):288-291 ( 2013).
Hollinger et al., "Diabodies: Small Bivalent and Bispecific Antibody Fragments" P Natl Acad Sci USA 90:6444-6448 (Jul. 1993).
Holm et al., "Functional mapping and single chain construction of the anti-cytokeratin 8 monoclonal antibody TS1" Mol Immunol 44:1075-1084 (2007).
Holt et al., "Domain antibodies: proteins for therapy" Trends Biotechnol 21(11):484-490 (Nov. 2003).
Huang et al., "IL-13 expression at the sites of allergen challenge in patients with asthma" J Immunol 155:2688-2694 (1995).
Humbert et al., "Elevated expression of messenger ribonucleic acid encoding IL-13 in the bronchial mucosa of atopic and nonatopic subjects with asthma" J Allergy Clin Immunol 99:657-665 (1997).
Hunter et al., "Preparation of Iodine-131 Labelled Human Growth Hormone of High Specific Activity" Nature 194(4827):495-496 (May 5, 1962).
Iba et al., "Changes in the specificity of antibodies against steroid antigens by introduction of mutatations into complementarity-determining regions of the VH domain" Protein Eng (Abstract only), 11(5):361-370 (1998).
Ingram et al., "IL-13 in asthma and allergic disease: Asthma phenotypes and targeted therapies" J Allergy Clin Immunol 130:829-842 ( 2012).
Inspiration Biopharmaceuticals announces clinical hold of clinical trials evaluating IB1001 for the treatment and prevention of bleeding in hemophilia B, Cambridge, MA (2012).
International Preliminary Report on Patentability issued in related Application No. PCT/US2014/055387, dated Mar. 15, 2016, 5 pages.
International Search Report for International Patent Application No. PCT/US14/55382, dated Jun. 15, 2015, 7 pages.
International Search Report on patentability for International Patent Application No. PCT/US2014/055387.
Ipsen and Inspiration Biopharmaceuticals announce closing of the IB1001 sale to Cangene Corporation Paris, France (2013).
Jakobovits et al., "Analysis of homozygous mutant chimeric mice: Deletion of the immunoglobulin heavy-chain joining region blocks B-cell development and antibody production" P Natl Acad Sci USA 90:2551-2555 (Mar. 1993).
Jakobovits et al., "Germ-line transmission and expression of a human-derived yeast artificial chromosome" Nature 362:255-258 (Mar. 18, 1993).
Jakubzick et al., "Therapeutic attenuation of pulmonary fibrosis via targeting of IL-4- and IL-13-responsive cells" J Immunol 171:2684-2693 ( 2003).
Janeway and Travers Immunobiology: The Immune System in Health and Disease "Allergy and Hypersensitivity" 3rd edition, New York and London:Garland Publishing Inc.,:11:1-11.25.
Janeway and Travers Immunobiology: The Immune System in Health and Disease "Adaptive immunity to infection" 3rd edition, New York and London:Garland Publishing Inc.,:9:31-9:33.
Jawa et al., "Evaluating Immunogencity Risk Due to Host Cell Protein Impurities in Antibody-Based Biotherapeautics" The AAPS Journal 18(6):14 (Nov. 2016).
Jenner et al., "Serum five light chain immunoassays: a guide to antigen excess detection" Clin Chim Acta 413:949 ( 2012).
Jensen et al., "Biochemical characterization and lysosomal localization of the mannose-6-phosphate protein p76 (hypothetical protein LOC196463)" Biochem J 402:449-463 ( 2007).
Jiang et al., "A novel peptide isolated from a phage display peptide library with trastuzumab can mimic antigen epitope of HER-2*" J Biol Chem 280(6):4656-4662 ( 2005).
Johnson et al., "Human Antibody Engineering" Curr Opin Struc Biol 3:564-571 ( 1993).
Jones et al., "Replacing the complementarity-determining regions in a human antibody with those from a mouse" Nature 321:522-525 (May 29, 1986).
Jones The Impact of Chemistry on Biotechnology "Sensitive detection and quantitation of protein contaminants in rDNA products" Phillips M.,American chemical Society,:193-201 ( 1988).
Kabat et al. Sequences of Proteins of Immunological Interest 5th edition,NIH,:2 pages ( 1991).
Kapp et al., "Interleukin 13 is secreted by and stimulates the growth of Hodgkin and Reed-Sternberg cells" J Exp Med 189(12):1939-1945 (Jun. 21, 1999).
Kasaian et al., "Efficacy of IL-13 neutralization in a sheep model of experimental asthma" Am J Respir Cell Mol Biol 36:368-376 ( 2007).
Kawakami et al., "Interleukin-13 receptor-targeted cancer therapy in an immunodeficient animal model of human head and neck cancer" Cancer Res 61:6194-6200 ( 2001).
Kawakami et al., "Intratumor administration of interleukin 13 receptor-targeted cytotoxin induces apoptotic cell death in human malignant glioma tumor xenografts" Mol Cancer Ther 1:999-1007 (Oct. 2002).
Keane et al., "IFN-γ-inducible protein-10 attenuates bleomycin-induced pulmonary fibrosis via inhibition of angiogenesis" J Immunol 163:5686-5692 ( 1999).
Keane et al., "Neutralization of the CXC chemokine, macrophage inflammatory protein-2, attenuates bleomycin-induced pulmonary fibrosis" J Immunol 162:5511-5518 ( 1999).
Kettleborough et al. et al., "Humanization of a Mouse Monoclonal Antibody by CDR-grafting: the Importance of Framework Residues on Loop Conformation" Protein Eng 4(7):773-783 ( 1991).
Kim et al., "IL-13-induced Clara cell secretory protein expression in airway epithelium: role of EGFR signaling pathway" Am J Physiol Lung Cell Mol Physiol 283:L67-L75 ( 2002).
Kimata et al., "Involvement of interleukin (IL)-13, but not IL-4, in spontaneous IgE and IgG4 production in nephrotic syndrome" Eur J Immunol (Abstract only), 25(6):1497-1501 ( 1995).
Kindt et al. Kuby Immunology "Antigens and Antibodies Chapter 4" 6th ed edition, N.Y.:W.H. Freeman and Co,:p. 91 ( 2007).
Kita et al., "Biochemical properties and pathophysiological roles of cytosolic phospholipase $A_2S$" Biochim Biophys Acta 1761:1317-1322 ( 2006).
Kohler and Milstein, "Continuous cultures of fused cells secreting antibody of predefined specificity" Nature 256:495-497 (Aug. 7, 1975).

(56) References Cited

OTHER PUBLICATIONS

Kotsimbos et al., "Interleukin-13 and interleukin-4 are coexpressed in atopic asthma" Proc Assoc Am Physicians 108(5):368-373 ( 1996).
Kozbor et al., "A Human Hybrid Myeloma for Production of Human Monoclonal Antibodies" J Immunol 133(6):3001-3005 (Dec. 1, 1984).
Krawitz et al., "Proteomic studies support the use of multi-product immunoassays to monitor host cell protein impurities" Proteomics 6:94-100 ( 2006).
Kroegel et al., "Endobronchial secretion of interleukin-13 following local allergen challenge in atopic asthma relationship to interleukin-4 and eosinophil counts" Eur Respir J 9:899-904 ( 1996).
Kuperman et al., "Direct effects of interleukin-13 on epithelial cells cause airway hyperreactivity and mucus overproduction in asthma" Nat Med 8(8):885-889 ( 2002).
Lakomek et al., "Initial insight into the function of the lysosomal 66.3 kDa protein from mouse by means of X-ray crystallography" BMC Structural Biol 9:56 ( 2009).
Laporte et al., "Molecular and structural basis of cytokine receptor pleiotropy in the interleukin-4/13 system" Cell 132(2):259-272 ( 2008).
Lee et al., "Interleukin-13 induces tissue fibrosis by selectively stimulating nad activating transforming growth factor $B_1$" J Exp Med 194(4):809-821 (Sep. 17, 2001).
Lee et al., "Serum levels of interleukins (IL)-4, IL-5, IL-13, and interferon-γ in acute asthma" J Asthma 38(8):665-671 ( 2001).
Leister, "Identification and control of process impurities and product related variants in the development and manufacture of a glycoprotein" IBC Life Sciences Product and Process Variants and Impurities Conference, Washington, D.C. ( 2013).
Levy et al., "Role of IL-13 in CD4 T cell-dependent IgE production in atopy" Int Arch Allergy Immunol 112:49-58 ( 1997).
Lewis et al., "Genomic landscapes of Chinese hamster ovary cell lines as revealed by the Cricetulus griseus draft genome" Nat Biotechnol 31(8):759-765 (Aug. 2013).
Liu et al., "Regulation of found in inflammatory zone 1 expression in bleomycin-induced lung fibrosis: Role of IL-4/IL-13 and mediation via STAT-6" J Immunol 173:3425-3431 ( 2004).
Liu et al., Sep./Oct. 2010, mAbs, 2:5, pp. 480-499.
Lucas et al., "Enzyme-linked immunosorbent assays (ELISAs) for the determination of contaminants resulting from the immunoaffinity purification of recombinant proteins" J Immunol Methods 113:113-122 ( 1988).
Luhrs et al., "Evicting hitchhiker antigens from purified antibodies" J Chromatograph B:1543-1552 ( 2009).
Lukacs et al., "Respiratory syncytial virus predisposes mice to augmented allergic airway responses via IL-13-mediated mechanisms" J Immunol 167:1060-1065 ( 2001).
MacCallum et al., "Antibody-antigen interactions: contact analysis and binding site topography" J Mol Biol 262(5):732-745 (Oct. 11, 1996).
Madhankumar et al., "Alanine-scanning mutagenesis of α-helix D segment of interleukin-13 reveals new functionally important residues of the cytokine" J Biol Chem 277(45):43194-43205 (Nov. 8, 2002).
Maini et al., "Interleukin-13 receptors on human prostate carcinoma cell lines represent a novel target for a chimeric protein composed of IL-13 and a mutated form of pseudomonas exotoxin" J Urology 158:945-953 ( 1997).
Mariuzza et al., "The Structure Basis of Antigen-Antibody Recognition" Ann Rev Biophys Biophys Chem 16:139-159 ( 1987).
Marks et al., "By-passing immunization, human antibodies from V-gene libraries displayed on phage" J Mol Biol 222:581-597 ( 1991).
Marks et al., "By-passing immunization. building high affinity human antibodies by chain shuffling" Bio/Technology 10:779-783 (Jul. 1992).

Marsh et al., "Linkage analysis of IL4 and other chromosome 5q31.1 markers and total serum immunoglobulin E concentrations" Science 264:1152-1156 (May 20, 1994).
Matshushita et al., "Upregulation of interleukin-13 and its receptor in a murine model of bleomycin-induced scleroderma" Int Arch Allergy Immunol 135:348-356 ( 2004).
McCafferty et al., "Phage Antibodies: Filamentous Phage Displaying Antibody Variable Domains" Nature 348:552-554 (Dec. 1990).
McKenzie et al., "Impaired development of Th2 cells in Il-13-deficient mice" Immunity 9:423-432 (Sep. 1998).
McKenzie et al., "Interleukin 13, a T-cell-derived cytokine that regulates human monocyte and B-cell function" Proc Natl Acad Sci USA 90:3735-3739 (Apr. 1993).
McKenzie et al., "Measurement of interleukin-13" Curr Protocols Immunol (Unit 6.18, Suppl. 10:6.18.1-6.18.5, Coligan et al., eds., John Wiley & Sons, New York).
Mechetner et al., "The effects of hitchhiker antigens co-eluting with affinity-purified research antibodies" J Chromatograph B 879:2583-2594 ( 2011).
Mehta et al., "Purifying therapeutic monoclonal antibodies" SBE Special Section/Bioprocessing:S14-S20.
Mentink-Kane et al., "Opposing roles for IL-13 and IL-13 receptor α2 in health and disease" Immunological Rev 202:191-202 ( 2004).
Merck Manual—Online Medical Dictionary, "Hyperimmunoglobulinemia E Syndrome," [on-line], Jul. 7, 2007 [Retrieved on Jul. 7, 2007], Retried from the Internet: <URL: http://www.merck.com/mmhe/sec16/ch184k.html>, pp. 1-2., pp. 1-2 (Jul. 7, 2007).
Merrifield, "Solid phase peptide synthesis: The synthesis of a tetrapeptide" J Am Chem Soc 85:2149-2154 ( 1963).
Mihara et al., "Host Cell Proteins: The Hidden Side of Biosimilarity Assessment" Journal of Pharmaceutical Sciences 104:3991-3996 ( 2015).
Millipore Technical Bulletin, Lit. No. 1026EN00, Jul. 2006 (available at www.Millipore.com).
Miloux et al., "Cloning of the human IL-13Rα1 chain and reconstitution with the IL-4Rα of a functional IL-4/IL-13 receptor complex" FEBS Lett 401:163-166 ( 1997).
Morimoto and Inouye, "Single-step purification of $F(ab^1)_2$ fragments of mouse monoclonal antibodies (immunoglobulins G1) by hydrophobic interaction high performance liquid chromatography using TSKgel phenyl-5PW" J Biochem Biophys Meth 24:107-117 ( 1992).
Morrison et al., "Chimeric human antibody molecules: Mouse antigen-binding domains with human constant region domains" P Natl Acad Sci USA 81:6851-6855 (Nov. 1984).
Mueller et al., "Structure, binding, and antagonists in the IL-4/IL-13 receptor system" Biochim Biophys Acta 1592:237-250 ( 2002).
Munson and Rodbard, "LIGAND: A Versatile Computerized Approach for Characterization of Ligand-Binding Systems" Anal Biochem 107(1):220-239 (Sep. 1, 1980).
Muyldermans et al., "Recognition of antigens by single-domain antibody fragments: the superfluous luxury of paired domains" Trends Biochem Sci 26(4):230-235 (Apr. 2001).
Naseer et al., "Expression of IL-12 and IL-13 mRNA in asthma and their modulation in response to steroid therapy" Am Respir Crit Care Med 155:845-857 ( 1997).
Noonan et al., "Dose-ranging study of lebrikizumab in asthmatic patients not receiving inhaled steroids" J Allergy Clin Immunol 132:567-574 ( 2013).
Noverr et al., "Production of eicosanoids and other oxylipins by pathogenic eukaryotic microbes" Clin Microbiol Rev 16(3):517-533 (Jul. 2003).
Noverr et al., "Role of PLB1 in pulmonary inflammation and cryptococcal eicosanoid production" Infect Immun 71(3):1538-1547 (Mar. 2003).
Nygren, H., "Conjugation of Horseradish Peroxidase to Fab Fragments with Different Homobifunctional and Heterobifunctional Cross-Linking Reagents" J Histochem Cytochem 30(5):407-412 (May 1982).
Ohno et al., "Antigen binding specificities of antibodies are primarily determined by seven residues of VH" Proc. Natl. Acad Sci. USA 82(9):2945-2949 ( 1985).

(56) References Cited

OTHER PUBLICATIONS

Okuma et al., "C-C chemokine receptor 2 (CCR2) deficiency improves bleomycin-induced pulmonary fibrosis by attenuation of both macrophage infiltration and production of macrophage-derived matrix metalloproteinases" J Pathol 204:594-604 ( 2004).
Omnitrope: EPAR-Scientific Discussion, European Medicines Agency, 2006.
Oshima et al., "Characterization of a powerful high affinity antagonist that inhibits biological activities of human interleukin-13" J Biol Chem 276(18):15185-15191 (May 4, 2001).
Oxford Concise Medical Dictionary "Atopy" 4th edition, Great Britian:Oxford Univeristy Press,:54-55 ( 1994).
Pahl et al., "Regulation of IL-13 synthesis in human lymphocytes: implications for asthma therapy" British Journal of Pharmacology 135:1915-1926 ( 2002).
Pain and Surolia, "Preparation of Protein A-Peroxidase Monoconjugate Using a Heterobifunctional Reagent, and its Use in Enzyme Immunoassays" J Immunol Methods 40(2):219-230 ( 1981).
Pawankar et al., "Nasal mast cells in perennial allergic rhinitics exhibit increased expression of the FceRI, CD40L, IL-4, and IL-13, and can induce IgE synthesis in B cells" J Clin Invest 99(7):1492-1499 (Apr. 1997).
Peebles et al., "Immune interaction between respiratory syncytial virus infection and allergen sensitization critically depends on timing of challenges" J Infect Dis 184:1374-1379 ( 2001).
Pluckthun, A. The Pharmacology of Monoclonal Antibodies. Handbook of Pharmacology "Antibodies from *Escherichia coli*" (Chapter 11), Rosenberg and Moore, eds., Berlin:Springer-Verlag, vol. 113:269-315 ( 1994).
Pluckthun, A., "Mono- and bivalent antibody fragments produced in *Escherichia coli*: engineering, folding and antigen binding" Immunol Reviews(130):151-188 ( 1992).
Portolano et al., "Lack of promiscuity in autoantigen-specific H and L chain combinations as revealed by human H and L chain 'roulette'" J Immunol 150(3):880-7 (Feb. 1, 1993).
Postma et al., "Genetic susceptibility to asthma—bronchial hyperresponsiveness coinherited with a major gene for atopy" N Engl J Med 333(14):894-900 ( 1995).
Presta et al., "Humanization of an antibody directed against IgE" J Immunol 151(5):2623-2632 (Sep. 1993).
Presta, "Antibody engineering" Curr Opin Struct Biol 2:593-596 ( 1992).
Punnonen et al. Allergy and Allergic Diseases: The New Mechanisms and Therpeutics "Cytokines and IgE regulation" J.A. Denburg, Totowa, NJ:Humana Press Inc.,:13-40 ( 1998).
Quarmby et al., "Immunogenicity: A critical issue in biotherapeutic development" AAPS Newsmagazine, May 12.
Rader et al., "A Phage Display Approach for Rapid Antibody Humanization. Designed Combinatorial V Gene Libraries" P Natl Acad Sci USA 95:8910-8915 (Jul. 1998).
Rasmussen et al., "Manufacture of recombinant polyclonal antibodies" Biotechnol Lett 29:845-852 ( 2007).
Reeck et al., "Homology in Proteins and Nucleic Acids: A Terminology Muddle and a Way out of it" Cell 50(5):667 ( 1987).
Repo et al., "Is the bovine lysosomal phospholipase B-like protein an amidase?" Proteins 82:300-311 ( 2014).
Rey et al., "Full automation and validation of a flexible ELISA platform for host cell protein and protein A impurity detection in biopharmaceuticals" J Pharmmaceutical and Biomedical Analysis 70:580-586 ( 2012).
Riechmann et al., "Reshaping human antibodies for therapy" Nature 332:323-327 (Mar 24, 1988).
Riemer et al., "Matching of trastuzumab (Herceptin) epitope mimics onto the surface of Her-2/neu—a new method of epitope definition" Mol Immunol 42:1121-1124 ( 2005).
Roberg et al., "Treatment of uveitis with recombinant human interleukin-13" B F Ophthalmol 82:1195-1198 ( 1998).
Roitt et al. Roitt's Essential Immunology "Chanter 6" (English Translation),:110-111 ( 2000).
Roitt, I.M. Essential Immunology "Hypersensitivity" 6TH edition, oXFORD:Blackwell Scientific Publications,:195-196 ( 1988).
Romer et al., "Efficacy and safety of a new ready-to-use recombinant human growth hormone solution" J Endocrinol Invest 30:578-589 ( 2007).
Rudikoff et al., "Single amino acid substitution altering antigen-binding specificity," Proc. Nat. Acad. Sci. USA, vol. 79, pp. 1979-1983, Mar. 1982.
Saenger, "Current status of biosimilar growth hormone" Int J Pediatric Endrocin:370329 ( 2009).
Saha et al., "Increased sputum and bronchial biopsy IL-13 expression in severe asthma" J Allergy Clin Immunol:685-691 (Mar. 2008).
Sambrook et al. Molecular Cloning: A Laboratory Manual (Table of Contents only, in 32 pages), 2nd edition, Cold Spring Harbor, NY: Cold Spring Harbor Laboratory Press, ( 1989).
Sandberg et al., "Mapping and partial characterization of proteases expressed by a CHO production cell line" Biotechnol Bioeng 95:961-971 ( 2006).
Santangelo et al., "Detection of antibodies to phospholipase B in patients infected with Cryptococcus neoformans by enzyme-linked immunosorbent assay 9ELISA)" medical mycology 43:335-341 (Jun. 2005).
Schacker et al., "Collagen deposition in HIV-1 infected lymphatic tissues and T cell homeostasis" J Clin Invest 110(8):1133-1139 (Oct. 2002).
Scheerens et al., "The effects of lebrikizumab in patients with mild asthma following whole lung allergen challenge" Clin Exper Allergy 44:38-46 ( 2014).
Schenauer et al., "Identification and quantification of host cell protein impuristies in biotherapeutics using mass spectrometry" Analyt Biochem 428:150-157 ( 2012).
Schildbach et al., "Modulation of antibody affinity by a non-contact residue" Protein Science 2:206-214 ( 1993).
Sharma, "Immunogenicity of therapeutic proteins, Part 2: Impact of container closures" Biotechnol Advances 25:318-324 ( 2007).
Shimoni, "Host Cell Protein ELISAs and the Use of Orthogonal Methods" Slides Washington, DC, pp. 25 ( Jan. 30, 2013).
Shukla et al., "Downstream processing of monoclonal antibodies—application of platform approaches" J Chromatograph B 848:28-39 ( 2007).
Shukla et al., "Host cell protein clearance during protein A chromatography: development of an improved column wash step" Biotechnol Prog 24:1115-1121 ( 2008).
Sims et al., "A Humanized CD18 Antibody Can Block Function Without Cell Destruction" J Immunol 151(4):2296-2308 (Aug. 15, 1993).
Singer et al., "Gens and Genoms" Moscow Mir. ((In Russian with English translation)), 1:63 ( 1988).
Sisodiya et al., "Studying host cell protein interactions with monoclonal antibodies using high throughput protein A chromatography" Biotechnol J 7:1233-1241 ( 2012).
Skerra, A., "Bacterial expression of immunoglobulin fragments" Curr Opin Immunol 5:256-262 ( 1993).
Skinnider et al., "Signal transducer and activator of transcription 6 is frequently activated in Hodgkin and Reed-Sternberg cells of Hodgkin lymphoma" Blood 99(2):618-626 (Jan. 15, 2002).
Skinnider et al., "The role of interleukin 13 in classical Hodgkin lymphoma" Leuk Lymphoma 43(6):1203-1210 ( 2002).
Stewart et al. Solid-Phase Peptide Synthesis, San Francisco, CA:W. H. Freeman Co. (1969).
Taber's Cyclopedic Medical Dictionary, "Atopy," p. 170 (1997), 18th Ed., F.A. Davis Company, Phladelphia.
Tait et al., "Host cell protein dynamics in the supermatant of a mAb producing CHO cell line" Biotechnol Bioeng 109(4):971-982 (Apr. 2012).
Tekkanat et al., "IL-13-induced airway hyperreactivity during respiratory syncytial virus infection is STAT6 dependent" J Immunol 166:3542-3548 ( 2001).
Teplyakov et al., "Epitope mapping of anti-interleukin-13 neutralizing antibody CNT0607" J Mol Biol 389:115-123 ( 2009).
Teplyakov et al., "On the domain pairing in chimeric antibodies" Mol Immunol 47:2422-2426 ( 2010).

(56) References Cited

OTHER PUBLICATIONS

Terabe et al., "NKT cell-mediated repression of tumor immunosurveillance by IL-13 and the IL-4R-STAT6 pathway" Nat Immunol 1(6):515-520 (Dec. 2000).
Terabe et al., "Role of IL-13 in regulation of anti-tumor immunity and tumor growth" Cancer Immunol Immunother 53:79-85 ( 2004).
Thakrar et al., "Assessing the efficacy and safety of Omnitrope" British J Clin Pharmacy 2:298-301 ( 2010).
Thompson et al., "Mutants of interleukin 13 with altered reactivity toward interleukin 13 receptors" J Biol Chem 274(42):29914-29950 (Oct. 15, 1999).
Thomson et al., "Lebrikizumab in the personalized management of asthma" Biologics: Targets and Therapy 6:329-335 ( 2012).
Tran et al., "Investigating interactions between phospholipase B-like 2 and antibodies during prodein a chromatography" J Chromatograph A 1438:31-38 ( 2016).
Trieu et al., "Inhibition of Hodgkin lymphoma cell line growth using an adenovirus expressing the soluble IL-13 decoy receptor (sIL-13Ralpha2)" Blood (Abstract No. 2272 only), 100.
Trieu et al., "Soluble interleukin-13R$\alpha$2 decoy receptor inhibits Hodgkin's lymphoma growth in vitro and in vivo" Cancer Res 64:3271-3275 ( 2004).
Triggiani et al., "Activation of human inflammatory cells by secreted phospholipases $A_2$" Biochim Biophys Acta 1761:1289-1300 ( 2006).
Tsarbopoulos et al., "Mass spectrometric mapping of disulfide bonds in recombinant human interleukin-13" J Mass Spectrometry 35:446-453 ( 2000).
Ultsch et al., "Structural basis of signaling blockade by anti-IL-13 antibody lebrikizumab" J Mol Biol. 425:1330-1339 ( 2013).
Vajdos et al. et al., "Comprehensive functional maps of the antigen-binding site of an anti-ErbB2 antibody obtained with shotgun scanning mutagenesis" J Mol Biol 320(2):415-428 (Jul. 5, 2002).
Van Cleave et al., "Validation of immunoassays for anti-drug antibodies" Dev Biol (Basel) 112:107-112 ( 2003).
Van Der Pouw Kraan et al., "Human IL-13 production is negatively influencedby CD3 engagement" J Immunol 156:1818-1823 ( 1996).
Van Der Pouw Kraan et al., "The role of IL-13 in IgE synthesis by allergic asthma patients" Clin Exp Immunol 111:129-135 ( 1998).
Vanderlaan et al., "Hamster phospholipase B-like 2 (PLBL2); A host-cell protein impurity in therapeutic monoclonal antibodies derived from Chinese hamster ovary cells" Bioprocess International 13(4):18 (Apr. 2015).
Venkayya et al., "The Th2 lymphocyte products IL-4 and IL-13 rapidly induce airway hyperresponsiveness through direct effects on resident airway cells" Am J Respir Cell Mol Biol 26:202-208 ( 2002).
Verhoeyen et al., "Reshaping human antibodies: Grafting an antilysozyme activity" Science 239:1534-1536 (Mar. 1988).
Vita et al., "Characterization and comparison of the interleukin 13 receptor with the interleukin 4 receptor on several cell types" J Biol Chem 270(8):3512-3517 ( 1995).
Vugmeyster et al., "Preclinical pharmacokinetics, interspecies scaling, and tissue distribution of humanized monoclonal anti-IL-13 antibodies with different IL-13 neutralization mechanisms" Int Immunopharmacology 8:477-483 ( 2008).
Wang et al., "Host cell proteins in biologics development: Identification, quantitation and risk assessment" Biotechnol Bioeng 103(3):446-458 (Jun. 15, 2009).
Wang et al., "Impact of residual impurities and contaminants on protein stability" J Pharm Sci 103:1315-1330 ( 2014).
Wang et al., "Precipitation of process-drived impurities in non-protein A purification schemes for antibodies" Biopharm Int, Downstream Processing 2010:4-10 (Oct. 2009).
Ward et al., "Binding activities of a repertoire of sigle immunoglobulin variable domains" Nature 341:544-546 (Oct. 12, 1989).
Wardemann et al., "Predominant autoantibody production by early human B cell precursors" Science 301:1374-1377 (Sep. 5, 2003).
Warner, J. O., "Bronchial hyperresponsiveness, atopy, airway inflammation, and asthma" Pediatr Allergy Immunol 9:56-60 ( 2003).

Waterhouse et al., "Combinatorial infection and in vivo recombination: a strategy for making large phage antibody repertoires" Nucl Acids Res 21(9):2265-2266 ( 1993).
Webb, S., "Attacks on asthma" Nat Biotechnol 29(10):860-863 ( 2011).
Wensel et al., "High-throughput screening of chromatographic separations: III. Monoclonal antibodies on ceramic hydroxyapatite" Biotechnol Bioeng 100(5):839-854 (Aug. 1, 2008).
Wikipedia entry for "Hypersensitivity" [on-line], [Retrieved on Jul. 2, 2007], pp. 1-4, Retrieved from the Internet: <URL: http://en.wikipedia.org/wiki/Hypersensitivity>, pp. 1-4 (Jul. 2, 2007).
Wills-Karp et al., "Interleukin-13: Central mediator of allergic asthma" Science 282:2258-2261 ( 1998).
Wills-Karp, "Interleukin-13 in asthma pathogenesis" Curr Allergy Asthma Rep 4(2):123-131 ( 2004).
Winkler et al. et al., "Changing the antigen binding specificity by single point mutations of an anti-p24 (HIV-1) antibody" J Immunol 165:4505-4514 ( 2000).
Wood et al., "Enhanced interleukin (IL)-13 responses in mice lacking IL-13 receptor $\alpha$ 2" J Exp Med 197(6):703-(Mar. 17, 2003).
World Health Organization, "International statistical classification of diseases and related health problems," 10th Revision, 1:535-537 (1992).
Wu et al., "Humanization of a murine monoclonal antibody by simultaneous optimization of framework and CDR residues" J Mol Biol 294(1):151-162 ( 1999).
Wynn, T A, "IL-13 effector functions" Annu. Rev Immunol 21:425-456 ( 2003).
Xu et al., "The genomic sequence of the Chinese hamster ovary (CHO)-K1 cell line" Nature Biotechnol 29(8):735-741 (Aug. 2011).
Xue et al., "Prevalence and isotypic complexity of the anti-Chinese hamster ovary host cell protein antibodies in normal human serum" AAPS J 12(1):98-106 (Mar. 2010).
Yang et al., "Anti-IL-13 monoclonal antibody inhibits airway hyperresponsiveness, inflammation and airway remodeling" Cytokine 28:224-232 ( 2004).
Yang et al., "Therapeutic dosing with anti-interleukin-13 monoclonal antibody inhibits asthma progression in mice" J Pharmacol Exp Ther 312:8-15 ( 2005).
Yssel et al. et al., Clinical Expermental Allergy 28( SUPPL Supplement 5):104-109 ( 1998).
Zafra et al., "Host cell proteins in biotechnology-derived products: A risk assessment framework" Biotechnol Bioeng 112(11):2284-2291 (Nov. 2015).
Zapata et al., "Engineering linear $F(ab')_2$ fragments for efficient production in *Escherichia coli* and enhanced antiproliferative activity" Protein Eng 8(10):1057-1062 ( 1995).
Zhang et al., "Identification, purification, and characterization of a soluble interleukin (IL)-13-binding protein" J Biol Chem 272(14):9474-9480 (Apr. 4, 1997).
Zhu et al., "A rapid cIEF-ESI-MS/MS method for host cell protein analysis of a recombinant human monoclonal antibody" Talanta 98:253-256 ( 2012).
Zhu-Shimoni et al., "Host cell protein testing by ELISAs and the use of orthogonal methods" Biotechnol Bioeng 111(12):2367-2379 (Dec. 2014).
Zuegg et al., "Structural model of human IL-13 defines the spatial interactions with the IL-13R$\alpha$/IL-4R$\alpha$ receptor" Immunol Cell Biol 79:332-339 ( 2001).
Vanderlaan et al., "Experience with Host Cell Protein Impurities in Biopharmaceuticals" Biotechnol. Prog. 34(4):827-837 (2018).
Fischer et al., "Specific Immune Response to Phospholipase B-Like 2 Protein, a Host Cell Impurity in Lebrikizumab Clinical Material", The AAPS Journal, 19(1):254-263 (Jan. 2017).
Adolfsson, O. et al., "An Effector-Reduced Anti-$\beta$-Amyloid (A$\beta$) Antibody with Unique A$\beta$ Binding Properties Promotes Neuroprotection and Glial Engulfment of A$\beta$", The Journal of Neuroscience, vol. 32, No. 28, Jul. 11, 2012, pp. 9677-9689.
Barghorn, S. et al., "Globular Amyloid $\beta$-Peptide$_{1-42}$ Oligomer—A Homogenous and Stable Neuropathological Protein in Alzheimer's Disease", Journal of Neurochemistry, vol. 95, 2005, pp. 834-847.
Hogwood, C. et al., "The Dynamics of the CHO Host Cell Protein Profile During Clarification and Protein A Capture in a Platform

(56) References Cited

OTHER PUBLICATIONS

Antibody Purification Process", Biotechnology and Bioengineering, vol. 110, No. 1, Jan. 2013, pp. 240-251.
Clinical trial NCT01875003, version Jun. 7, 2013, and version May 15, 2017, retrieved from www.clinicaltrials.gov, 27 pages.
Clinical trial NCT01867125, version May 29, 2013, and version May 18, 2017, retrieved from www.clinicaltrials.gov, 31 pages.
Clinical trial NCT01868061, version May 30, 2013, and version May 18, 2017, retrieved from www.clinicaltrials.gov, 35 pages.
Marek et al., "Isolation of monoclonal antibody from a Chinese hamster ovary supernatant. I: Assessment of different separation concepts" Journal of Chromatography A 1305:55-63 (2013).

SEQUENCE LISTING

<160> NUMBER OF SEQ ID NOS: 34

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Tyr Ser Val Asn
1               5

<210> SEQ ID NO 2
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ile Trp Gly Asp Gly Lys Ile Val Tyr Asn Ser Ala Leu Lys Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Gly Tyr Tyr Pro Tyr Ala Met Asp Asn
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Lys Ser Val Asp Ser Tyr Gly Asn Ser Phe Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Asn Asn Glu Asp Pro Arg Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Thr Leu Arg Glu Ser Gly Pro Ala Leu Val Lys Pro Thr Gln Thr
```

```
1               5                   10                  15
Leu Thr Leu Thr Cys Thr Val Ser Gly Phe Ser Leu Ser Ala Tyr Ser
            20                  25                  30

Val Asn Trp Ile Arg Gln Pro Pro Gly Lys Ala Leu Glu Trp Leu Ala
            35                  40                  45

Met Ile Trp Gly Asp Gly Lys Ile Val Tyr Asn Ser Ala Leu Lys Ser
            50                  55                  60

Arg Leu Thr Ile Ser Lys Asp Thr Ser Lys Asn Gln Val Val Leu Thr
65                  70                  75                  80

Met Thr Asn Met Asp Pro Val Asp Thr Ala Thr Tyr Tyr Cys Ala Gly
            85                  90                  95

Asp Gly Tyr Tyr Pro Tyr Ala Met Asp Asn Trp Gly Gln Gly Ser Leu
            100                 105                 110

Val Thr Val Ser Ser
            115
```

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
            50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
            85                  90                  95

Gly Asp Gly Tyr Tyr Pro Tyr Ala Met Asp Asn Trp Gly Gln Gly Ser
            100                 105                 110

Leu Val Thr Val Ser Ser
            115
```

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
```

```
                    50                  55                  60
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                     85                  90                  95

Glu Asp Pro Arg Thr Phe Gly Gly Gly Thr Lys Val Glu Ile Lys Arg
                100                 105                 110
```

<210> SEQ ID NO 10
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Val Thr Leu Arg Glu Ser Gly Pro Ala Leu Val Lys Pro Thr Gln Thr
 1               5                  10                  15

Leu Thr Leu Thr Cys Thr Val Ser Gly Phe Ser Leu Ser Ala Tyr Ser
                 20                  25                  30

Val Asn Trp Ile Arg Gln Pro Pro Gly Lys Ala Leu Glu Trp Leu Ala
             35                  40                  45

Met Ile Trp Gly Asp Gly Lys Ile Val Tyr Asn Ser Ala Leu Lys Ser
 50                  55                  60

Arg Leu Thr Ile Ser Lys Asp Thr Ser Lys Asn Gln Val Val Leu Thr
 65                  70                  75                  80

Met Thr Asn Met Asp Pro Val Asp Thr Ala Thr Tyr Tyr Cys Ala Gly
                 85                  90                  95

Asp Gly Tyr Tyr Pro Tyr Ala Met Asp Asn Trp Gly Gln Gly Ser Leu
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly
            435                 440

<210> SEQ ID NO 11
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
                20                  25                  30

Ser Val Asn Trp Ile Arg Gln Pro Pro Gly Lys Ala Leu Glu Trp Leu
            35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220
```

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 12
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Thr Leu Arg Glu Ser Gly Pro Ala Leu Val Lys Pro Thr Gln Thr
1               5                   10                  15

Leu Thr Leu Thr Cys Thr Val Ser Gly Phe Ser Leu Ser Ala Tyr Ser
                20                  25                  30

Val Asn Trp Ile Arg Gln Pro Pro Gly Lys Ala Leu Glu Trp Leu Ala
            35                  40                  45

Met Ile Trp Gly Asp Gly Lys Ile Val Tyr Asn Ser Ala Leu Lys Ser
50                  55                  60

Arg Leu Thr Ile Ser Lys Asp Thr Ser Lys Asn Gln Val Val Leu Thr
65                  70                  75                  80

Met Thr Asn Met Asp Pro Val Asp Thr Ala Thr Tyr Tyr Cys Ala Gly
                85                  90                  95

Asp Gly Tyr Tyr Pro Tyr Ala Met Asp Asn Trp Gly Gln Gly Ser Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys

```
            130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 13
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45
```

```
Ala Met Ile Trp Gly Asp Gly Lys Ile Val Tyr Asn Ser Ala Leu Lys
 50                  55                  60

Ser Arg Leu Thr Ile Ser Lys Asp Thr Ser Lys Asn Gln Val Val Leu
 65                  70                  75                  80

Thr Met Thr Asn Met Asp Pro Val Asp Thr Ala Thr Tyr Tyr Cys Ala
                 85                  90                  95

Gly Asp Gly Tyr Tyr Pro Tyr Ala Met Asp Asn Trp Gly Gln Gly Ser
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 14
<211> LENGTH: 218
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 14

```
Asp Ile Val Met Thr Gln Ser Pro Asp Ser Leu Ser Val Ser Leu Gly
1               5                   10                  15
Glu Arg Ala Thr Ile Asn Cys Arg Ala Ser Lys Ser Val Asp Ser Tyr
            20                  25                  30
Gly Asn Ser Phe Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Asn Asn
                85                  90                  95
Glu Asp Pro Arg Thr Phe Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

```
Asp Tyr Ala Met His
1               5
```

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

```
Gly Ile Asn Trp Ser Ser Gly Gly Ile Gly Tyr Ala Asp Ser Val Lys
1               5                   10                  15
Gly
```

```
<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ile Gly Gly Phe Gly Glu Phe Tyr Trp Asn Phe Gly Leu
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gln Ser Val Arg Ser Tyr Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ala Ser Asn Arg Ala Thr
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Arg Ser Asn Trp Pro Pro Ala Thr
1               5                   10

<210> SEQ ID NO 21
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Ser Ser Gly Gly Ile Gly Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Arg Asp Ile Gly Gly Phe Gly Phe Tyr Trp Asn Phe Gly Leu
            100                 105                 110

Trp Gly Arg Gly Thr Leu Val Thr Val Ser Ser
            115                 120
```

<210> SEQ ID NO 22
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Thr Phe Gly Gly Gly Thr Lys Val Glu Ile Lys
            100                 105
```

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

```
Gly Phe Thr Phe Ser Ser Tyr Gly Met Ser
 1               5                  10
```

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

```
Ser Ile Asn Ser Asn Gly Gly Ser Thr Tyr Tyr Pro Asp Ser Val Lys
 1               5                  10                  15
```

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gly Asp Tyr
1

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Ser Gln Ser Leu Val Tyr Ser Asn Gly Asp Thr Tyr Leu His
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Val Ser Asn Arg Phe Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Gln Ser Thr His Val Pro Trp Thr
1               5

<210> SEQ ID NO 29
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser

```
            100                 105                 110
Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
            435

<210> SEQ ID NO 30
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Ser Pro Leu Ser Leu Pro Val Thr Pro Gly
1               5                   10                  15
```

```
Glu Pro Ala Ser Ile Ser Cys Arg Ser Ser Gln Ser Leu Val Tyr Ser
                20                  25                  30

Asn Gly Asp Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Val Leu Leu Asp Ala Ala Ser Gly Gln Leu Arg
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Leu Glu Asp Ser Tyr Glu Gly Arg
1               5

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Phe Ile Pro Asn Gly Pro Ser Pro Gly Ser Arg
```

```
<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Thr Ser Phe Ser Leu Ala Lys
1               5
```

COMPOSITIONS COMPRISING PURIFIED RECOMBINANT IL-13 ANTIBODY

CROSS REFERENCE TO RELATED APPLICATION

This application is a divisional of U.S. application Ser. No. 15/065,693, filed Mar. 9, 2016, which is a continuation of International Application No. PCT/US2014/055387 having an international filing date of Sep. 12, 2014, which claims the benefit of priority of provisional U.S. Application No. 61/877,517 filed Sep. 13, 2013, each of which is incorporated by reference herein in its entirety for any purpose.

SEQUENCE LISTING

The instant application contains a Sequence Listing which has been submitted via EFS-Web and is hereby incorporated by reference in its entirety. Said ASCII copy, created on Feb. 1, 2018, is named 2018-02-01_01146-0063-02US_sequence_listing.txt and is 34,888 bytes in size.

FIELD

Purified recombinant polypeptides isolated from Chinese hamster ovary host cells, including antibodies, such as therapeutic antibodies, and methods of making and using such polypeptides are provided.

BACKGROUND

A number of drugs are on the market or in development for treating asthma and other respiratory disorders. One of the targets for asthma therapy is IL-13. IL-13 is a pleiotropic TH2 cytokine produced by activated T cells, NKT cells, basophils, eosinophils, and mast cells, and it has been strongly implicated in the pathogenesis of asthma in preclinical models. IL-13 antagonists, including anti-IL-13 antibodies, have previously been described. Certain such antibodies have also been developed as human therapeutics. Recently, several studies have shown clinical activity of monoclonal antibodies against IL-13 in the treatment of asthma (See, e.g., Corren et al., 2011, *N. Engl. J. Med.* 365, 1088-1098; Gauvreau et al., 2011, *Am. J. Respir. Crit. Care Med.* 183, 1007-1014; Ingram and Kraft, 2012, *J. Allergy Clin. Immunol.* 130, 829-42; Webb, 2011, *Nat Biotechnol* 29, 860-863). Of these, lebrikizumab, a humanized IgG4 antibody that neutralizes IL-13 activity, improved lung function in asthmatics who were symptomatic despite treatment with, for the majority, inhaled corticosteroids and a long-acting beta2-adrenergic receptor agonist (Corren et al., 2011, *N. Engl. J. Med.* 365, 1088-1098).

In addition, IL-13 has been implicated in numerous other allergic and fibrotic disorders. For example, such diseases and/or conditions mediated by IL13 include, but are not limited to, allergic asthma, non-allergic (intrinsic) asthma, allergic rhinitis, atopic dermatitis, allergic conjunctivitis, eczema, urticaria, food allergies, chronic obstructive pulmonary disease, ulcerative colitis, RSV infection, uveitis, scleroderma, and osteoporosis.

For recombinant biopharmaceutical proteins to be acceptable for administration to human patients, it is important that residual impurities resulting from the manufacture and purification process are removed from the final biological product. These process components include culture medium proteins, immunoglobulin affinity ligands, viruses, endotoxin, DNA, and host cell proteins. These host cell impurities include process-specific host cell proteins (HCPs), which are process-related impurities/contaminants in the biologics derived from recombinant DNA technology. While HCPs are typically present in the final drug substance in small quantities (in parts-per-million or nanograms per milligram of the intended recombinant protein), it is recognized that HCPs are undesirable and their quantities should be minimized. For example, the U.S. Food and Drug Administration (FDA) requires that biopharmaceuticals intended for in vivo human use should be as free as possible of extraneous impurities, and requires tests for detection and quantitation of potential contaminants/impurities, such as HCPs.

Procedures for purification of proteins from cell debris initially depend on the site of expression of the protein. Some proteins are secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by centrifugation or by filtration. The same problem arises with directly secreted proteins due to the natural death of cells and release of intracellular host cell proteins in the course of the protein production run.

Once a solution containing the protein of interest is obtained, its separation from the other proteins produced by the cell is usually attempted using a combination of different chromatography techniques. Typically, these techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Ion-exchange chromatography, named for the exchangeable counterion, is a procedure applicable to purification of ionizable molecules. Ionized molecules are separated on the basis of the non-specific electrostatic interaction of their charged groups with oppositely charged molecules attached to the solid phase support matrix, thereby retarding those ionized molecules that interact more strongly with solid phase. The net charge of each type of ionized molecule, and its affinity for the matrix, varies according to the number of charged groups, the charge of each group, and the nature of the molecules competing for interaction with the charged solid phase matrix. These differences result in resolution of various molecule types by ion-exchange chromatography. In typical protein purification using ion exchange chromatography, a mixture of many proteins derived from a host cell, such as in mammalian cell culture, is applied to an ion-exchange column. After non-binding molecules are washed away, conditions are adjusted, such as by changing pH, counter ion concentration and the like in step- or gradient-mode, to release from the solid phase a non-specifically retained or retarded ionized protein of interest and separating it from proteins having different charge characteristics. Anion exchange chromatography involves competition of an anionic molecule of interest with the negative counter ion for interaction with a positively charged molecule attached to the solid phase matrix at the pH and under the conditions of a particular separation process. By contrast, cation exchange chromatography involves competition of a cationic molecule of interest with the positive counter ion for a negatively charged molecule attached to the solid phase matrix at the pH and under the conditions of a particular separation process. Mixed mode ion exchange chromatography (also referred to as multimodal ion exchange chromatography) involves the use of a combination of cation and anion exchange chromatographic media in the same step. In particular, "mixed mode" refers to a solid phase support matrix to which is covalently attached a mixture of cation exchange, anion exchange, and hydrophobic interaction moieties.

Hydroxyapatite chromatography of proteins involves the non-specific interaction of the charged amino or carboxylate groups of a protein with oppositely charged groups on the hydroxyapatite, where the net charge of the hydroxyapatite and protein are controlled by the pH of the buffer. Elution is accomplished by displacing the non-specific protein-hydroxyapatite pairing with ions such as $Ca2+$ or $Mg2+$. Negatively charged protein groups are displaced by negatively charged compounds, such as phosphates, thereby eluting a net-negatively charged protein.

Hydrophobic interaction chromatography (HIC) is typically used for the purification and separation of molecules, such as proteins, based on differences in their surface hydrophobicity. Hydrophobic groups of a protein interact non-specifically with hydrophobic groups coupled to the chromatography matrix. Differences in the number and nature of protein surface hydrophobic groups results in differential retardation of proteins on a HIC column and, as a result, separation of proteins in a mixture of proteins.

Affinity chromatography, which exploits a specific structurally dependent (i.e., spatially complementary) interaction between the protein to be purified and an immobilized capture agent, is a standard purification option for some proteins, such as antibodies. Protein A, for example, is a useful adsorbent for affinity chromatography of proteins, such as antibodies, which contain an Fc region. Protein A is a 41 kD cell wall protein from *Staphylococcus* aureas which binds with a high affinity (about $10^{-8}M$ to human IgG) to the Fc region of antibodies.

Purification of recombinant polypeptides is typically performed using bind and elute chromatography (B/E) or flow-through (F/T) chromatography. These are briefly described below.

Bind and Elute Chromatography (B/E): Under B/E chromatography the product is usually loaded to maximize dynamic binding capacity (DBC) to the chromatography material and then wash and elution conditions are identified such that maximum product purity is attained in the eluate.

Various B/E methods for use with protein A affinity chromatography, including various intermediate wash buffers, have been described. For example, U.S. Pat. Nos. 6,127,526 and 6,333,398 describe an intermediate wash step during Protein A chromatography using hydrophobic electrolytes, e.g., tetramethylammonium chloride (TMAC) and tetraethylammonium chloride (TEAC), to remove the contaminants, but not the immobilized Protein A or the protein of interest, bound to the Protein A column. U.S. Pat. No. 6,870,034 describes additional methods and wash buffers for use with protein A affinity chromatography.

Flow Through Chromatography (F/T): Using F/T chromatography, load conditions are identified where impurities strongly bind to the chromatography material while the product flows through. F/T chromatography allows high load density for standard monoclonal antibody preparations (MAbs).

In recombinant anti-IL13 MAb preparations and certain other recombinant polypeptides produced in CHO cells, we identified an enzyme, phospholipase B-like 2, as a single CHOP species present in excess of available antibodies in a total CHOP ELISA assay. As used herein, "PLB2" and "PLBL2" and "PLBD2" are used interchangeably and refer to the enzyme "phospholipase B-like 2" or its synonym, "phospholipase B-domain-like 2". Certain scientific publications on PLBL2 include Lakomek, K. et al., BMC Structural Biology 9:56 (2009); Deuschl, et al., FEBS Lett 580:5747-5752 (2006). PLBL2 is synthesized as a pre-pro-enzyme with parent MW of about 66,000. There is an initial leader sequence which is removed and potential 6 mannose-6-phosphate (M-6-P) groups are added during post-translational modification. M-6-P is a targeting modification that directs this enzyme to the lysosome via the M-6-P receptor. PLBL2 contains 6 cysteines, two of which have free sulfhydrals, and four form disulfide bonds. In acidic environments, PLBL2 is further clipped into the N- and C-terminal fragments having 32,000 and 45,000 MW, respectively. By analogy with other lysosomal enzymes, this cleavage is an activating step, allowing and access of the substrate to the active site.

There is about 80% PLBL2 amino acid sequence homology between hamster and human forms of the enzyme. The enzyme activity is thought to be to cleave either fatty acid chain from the phospholipids that make up cell membranes. There are other phospholipases with different substrate cleavage specificities. Similar enzymatic activities exist in microorganisms, where they are often a virulence factor. Although microorganisms have a similar enzymatic activity, the protein generating this activity is different, and there is low sequence homology between microbial and mammalian PLBL2 enzymes. Phospholipases produce free fatty acids (FFA) as one product of the substrate hydrolysis. Free fatty acids are themselves a potential immune-signaling factor. Dehydrogenation converts FFA to arachadonic acid which potentially participates in inflammation cascades involving eicosanoids.

Having identified PLBL2 as a single HCP (CHOP) in recombinant anti-IL13 MAb preparations and certain other recombinant polypeptides produced in CHO cells, we developed reagents, methods, and kits for the specific, sensitive, and quantitative determination of PLBL2 levels in anti-IL-13 Mab preparations (and other recombinant polypeptide products) and at various stages of purification. These are briefly described in the Examples below and also in U.S. Provisional Patent Application Nos. 61/877,503 and 61/991,228. In addition, there was the formidable challenge of developing a large-scale, robust, and efficient process for the purification of anti-IL13 MAb (and other recombinant polypeptide products) resulting in MAb of sufficient purity (including removal of PLBL2) for human therapeutic use including late-stage clinical and commercial use. The invention described herein meets certain of the above-described needs and provides other benefits.

All references cited herein, including patent applications and publications, are incorporated by reference in their entirety.

SUMMARY

The invention is based, at least in part, on the development of improved processes for the purification of recombinant polypeptides produced in Chinese hamster ovary (CHO) cells that provide purified product with substantially reduced levels of hamster PLBL2. Recombinant polypeptides purified according to the methods of the invention, including therapeutic antibodies such as an anti-IL13 antibody, may have reduced immunogenicity when administered to human subjects.

Accordingly, in one aspect, compositions comprising an anti-IL13 monoclonal antibody purified from CHO cells comprising the anti-IL13 antibody and a residual amount of hamster PLBL2 are provided. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6. In certain embodiments, the anti-IL13 antibody comprises a heavy chain variable region having the amino acid sequence of SEQ ID NO.: 7. In certain embodiments, the anti-IL13 antibody comprises a light chain variable region having the amino acid sequence of SEQ ID NO.: 9. In certain embodiments, the anti-IL13 antibody comprises a heavy chain having the amino acid sequence of SEQ ID NO.: 10. In certain embodiments, the anti-IL13 antibody comprises a light chain having the amino acid sequence of SEQ ID NO.: 14. In certain embodiments, the anti-IL13 antibody comprises a heavy chain variable region having the amino acid sequence of SEQ ID NO.: 7 and a light chain variable region having the amino acid sequence of SEQ ID NO.: 9. In certain embodiments, the anti-IL13 antibody comprises a heavy chain having the amino acid sequence of SEQ ID NO.: 10 and a light chain having the amino acid sequence of SEQ ID NO.: 14. In certain embodiments, the amount of hamster PLBL2 in the composition is quantified using an immunoassay or a mass spectrometry assay. In certain embodiments, the immunoassay is a total Chinese hamster ovary protein ELISA or a hamster PLBL2 ELISA. In certain embodiments, the mass spectrometry assay is LC-MS/MS.

In another aspect, anti-IL13 monoclonal antibody preparations isolated and purified from CHO cells by a process comprising a hydrophobic interaction chromatography (HIC) step are provided. In certain embodiments, the purified preparation comprises the anti-IL13 antibody and a residual amount of hamster PLBL2. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the HIC step comprises PHENYL SEPHAROSE™ 6 Fast Flow (High Sub) resin. In certain embodiments, the HIC step comprises operating a resin-containing column in flow-through mode. In certain embodiments, the HIC step comprises an equilibration buffer and a wash buffer, wherein each of the equilibration buffer and the wash buffer comprise 50 mM sodium acetate pH 5.0. In certain embodiments, the flow-through is monitored by absorbance at 280 nanometers and the flow-through is collected between 0.5 OD to 1.5 OD. In certain embodiments, the flow-through is collected for a maximum of 8 column volumes. In certain embodiments, the process further comprises an affinity chromatography step. In certain embodiments, the affinity chromatography is protein A chromatography. In certain embodiments, the process further comprises an ion exchange chromatography step. In certain embodiments, the ion exchange chromatography is anion exchange chromatography. In certain embodiments, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6. In certain embodiments, the anti-IL13 antibody comprises a heavy chain variable region having the amino acid sequence of SEQ ID NO.: 7. In certain embodiments, the anti-IL13 antibody comprises a light chain variable region having the amino acid sequence of SEQ ID NO.: 9. In certain embodiments, the anti-IL13 antibody comprises a heavy chain having the amino acid sequence of SEQ ID NO.: 10. In certain embodiments, the anti-IL13 antibody comprises a light chain having the amino acid sequence of SEQ ID NO.: 14. In certain embodiments, the anti-IL13 antibody comprises a heavy chain variable region having the amino acid sequence of SEQ ID NO.: 7 and a light chain variable region having the amino acid sequence of SEQ ID NO.: 9. In certain embodiments, the anti-IL13 antibody comprises a heavy chain having the amino acid sequence of SEQ ID NO.: 10 and a light chain having the amino acid sequence of SEQ ID NO.: 14. In certain embodiments, the amount of hamster PLBL2 is quantified using an immunoassay or a mass spectrometry assay. In certain embodiments, the immunoassay is a total Chinese hamster ovary protein ELISA or a hamster PLBL2 ELISA. In certain embodiments, the mass spectrometry assay is LC-MS/MS.

In yet another aspect, purified anti-IL13 monoclonal antibody preparations isolated from CHO cells are provided. In certain embodiments, the antibody preparation is purified by a process comprising a first Protein A affinity chromatography step, a second anion exchange chromatography step, and a third hydrophobic interaction chromatography (HIC) step thereby producing a purified preparation, In certain embodiments, the purified preparation comprises the anti-IL13 antibody and a residual amount of hamster PLBL2. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the affinity chromatography step comprises MABSELECT SURE™ resin, the anion exchange chromatography step comprises Q SEPHAROSE™ Fast Flow, and the HIC step comprises PHENYL SEPHAROSE™ 6 Fast Flow (high sub). In certain embodiments, the affinity chromatography step comprises operating a MABSELECT SURE™ resin-containing column in bind-elute mode, the anion exchange chromatography step comprises operating a Q SEPHAROSE™ Fast Flow resin-containing column in bind-elute mode, and the HIC step comprises operating a PHENYL SEPHAROSE™ 6 Fast Flow (High Sub) resin-containing column in flow-through mode. In certain embodiments, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6. In certain embodiments, the anti-IL13 antibody comprises a heavy chain variable region having the amino acid sequence of SEQ ID NO.: 7. In certain embodiments, the anti-IL13 antibody comprises a light chain variable region having the amino acid sequence of SEQ ID NO.: 9. In certain embodiments, the anti-IL13 antibody comprises a heavy chain having the amino acid sequence of SEQ ID NO.: 10. In certain embodiments, the anti-IL13 antibody comprises a light chain having the amino acid sequence of SEQ ID NO.: 14. In certain embodiments, the anti-IL13 antibody comprises a heavy chain variable region having the amino acid sequence of SEQ ID NO.: 7 and a light chain variable region having the amino acid sequence of SEQ ID NO.: 9. In certain embodiments, the anti-IL13 antibody comprises a heavy chain having the amino acid sequence of SEQ ID NO.: 10 and a light chain having the amino acid sequence of SEQ ID NO.: 14. In certain embodiments, the amount of hamster PLBL2 is quantified using an immunoassay or a mass spectrometry assay. In certain embodiments, the immunoassay is a total Chinese hamster ovary protein ELISA or a hamster PLBL2 ELISA. In certain embodiments, the mass spectrometry assay is LC-MS/MS.

In still yet another aspect, methods of purifying a recombinant polypeptide produced in CHO cells, wherein the method provides a purified preparation comprising the recombinant polypeptide and residual amount of hamster PLBL2 are provided. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the recombinant polypeptide is selected from a growth factor, a cytokine, an antibody, an antibody fragment, and an immunoadhesin. In certain embodiments, the recombinant polypeptide is an antibody. In certain embodiments, the antibody is a humanized monoclonal antibody. In certain embodiments, the antibody is IgG1, or IgG2, or IgG3, or IgG4. In certain embodiments, the antibody is IgG1. In certain embodiments, the antibody is IgG2. In certain embodiments, the antibody is IgG3. In certain embodiments, the antibody is IgG4. In certain embodiments, the methods comprise a hydrophobic interaction chromatography (HIC) step. In certain embodiments, the HIC step comprises PHENYL SEPHAROSE™ 6 Fast Flow (High Sub) resin.

In certain embodiments of the above purification methods, the purified antibody is anti-IL13. In certain embodiments, the antibody is lebrikizumab. In certain embodiments, the HIC step comprises operating a resin-containing column in flow-through mode. In certain embodiments, the HIC step comprises an equilibration buffer and a wash buffer, wherein each of the equilibration buffer and the wash buffer comprise 50 mM sodium acetate pH 5.0. In certain embodiments, the flow-through is monitored by absorbance at 280 nanometers and the flow-through is collected between 0.5 OD to 1.5 OD. In certain embodiments, the flow-through is collected for a maximum of 8 column volumes. In certain embodiments, the methods further comprise an affinity chromatography step. In certain embodiments, the affinity chromatography is protein A chromatography. In certain embodiments, the methods further comprise an ion exchange chromatography step. In certain embodiments, the ion exchange chromatography is anion exchange chromatography. In certain embodiments, the methods comprise a first Protein A affinity chromatography step, a second anion exchange chromatography step, and a third hydrophobic interaction chromatography (HIC) step. In certain embodiments, the affinity chromatography step comprises MABSELECT SURE™ resin, the anion exchange chromatography step comprises Q SEPHAROSE™ Fast Flow, and the HIC step comprises PHENYL SEPHAROSE™ 6 Fast Flow (high sub). In certain embodiments, the affinity chromatography step comprises operating a MABSELECT SURE™ resin-containing column in bind-elute mode, the anion exchange chromatography step comprises operating a Q SEPHAROSE™ Fast Flow resin-containing column in bind-elute mode, and the HIC step comprises operating a PHENYL SEPHAROSE™ 6 Fast Flow (High Sub) resin-containing column in flow-through mode. In certain embodiments, the amount of hamster PLBL2 is quantified using an immunoassay or a mass spectrometry assay. In certain embodiments, the immunoassay is a total Chinese hamster ovary protein ELISA or a hamster PLBL2 ELISA. In certain embodiments, the mass spectrometry assay is LC-MS/MS.

In certain embodiments of the above purification methods, the purified antibody is anti-Abeta. In certain embodiments, the anti-Abeta antibody is crenezumab. In certain embodiments, the anti-Abeta antibody comprises three heavy chain CDRs, CDR-H1 having the amino acid sequence of SEQ ID NO.:23, CDR-H2 having the amino acid sequence of SEQ ID NO.:24, and CDR-H3 having the amino acid sequence of SEQ ID NO.:25, and three light chain CDRs, CDR-L1 having the amino acid sequence of SEQ ID NO.:26, CDR-L2 having the amino acid sequence of SEQ ID NO.:27, and CDR-L3 having the amino acid sequence of SEQ ID NO.:28. In certain embodiments, the anti-Abeta antibody comprises a heavy chain variable region having the amino acid sequence of SEQ ID NO.:29. In certain embodiments, the anti-Abeta antibody comprises a light chain variable region having the amino acid sequence of SEQ ID NO.:30. In certain embodiments, the anti-Abeta antibody comprises a heavy chain variable region having the amino acid sequence of SEQ ID NO.:29 and a light chain variable region having the amino acid sequence of SEQ ID NO.:30. In certain embodiments, the HIC step comprises operating a resin-containing column in flow-through mode. In certain embodiments, the HIC step comprises an equilibration buffer and a wash buffer, wherein each of the equilibration buffer and the wash buffer comprise 150 mM sodium acetate pH 5.0. In certain embodiments, the HIC step comprises an equilibration buffer and a wash buffer, wherein each of the equilibration buffer and the wash buffer comprise 150 mM sodium acetate pH 4.0. In certain embodiments, the HIC step comprises an equilibration buffer and a wash buffer, wherein each of the equilibration buffer and the wash buffer comprise 150 mM sodium acetate, 240 mM sodium sulfate pH 4.0. In certain embodiments, the HIC step comprises an equilibration buffer and a wash buffer, wherein each of the equilibration buffer and the wash buffer comprise 150 mM sodium acetate, 240 mM sodium sulfate pH 5.0. In certain embodiments, the load density is 300 g/L. In certain embodiments, the load density is 100 g/L. In certain embodiments, the flow-through is monitored by absorbance at 280 nanometers and the flow-through is collected beginning at 0.5 OD and collection continues for 10 column volumes. In certain embodiments, the methods further comprise an affinity chromatography step. In certain embodiments, the affinity chromatography is protein A chromatography. In certain embodiments, the methods further comprise a mixed mode chromatography step. In certain embodiments, the methods comprise a first Protein A affinity chromatography step, a second mixed mode chromatography step, and a third hydrophobic interaction chromatography (HIC) step. In certain embodiments, the affinity chromatography step comprises MABSELECT SURE™ resin, the mixed mode chromatography step comprises CAPTO™ Adhere, and the HIC step comprises PHENYL SEPHAROSE™ 6 Fast Flow (high sub). In certain embodiments, the affinity chromatography step comprises operating a MABSELECT SURE™ resin-containing column in bind-elute mode, the mixed mode chromatography step comprises operating a CAPTO™ Adhere resin-containing column in flow-through mode, and the HIC step comprises operating a PHENYL SEPHAROSE™ 6 Fast Flow (High Sub) resin-containing column in flow-through mode. In certain embodiments, the amount of hamster PLBL2 is quantified using an immunoassay or a mass spectrometry assay. In certain embodiments, the immunoassay is a total Chinese hamster ovary protein ELISA or a hamster PLBL2 ELISA. In certain embodiments, the mass spectrometry assay is LC-MS/MS.

In yet a further aspect of the above purification methods, the purified antibody is IgG1. In some embodiments, the antibody is anti-IL17 A/F. In some embodiments, the anti-IL17 A/F antibody comprises three heavy chain CDRs, CDR-H1 having the amino acid sequence of SEQ ID NO.:15, CDR-H2 having the amino acid sequence of SEQ ID NO.:16, and CDR-H3 having the amino acid sequence of SEQ ID NO.:17, and three light chain CDRs, CDR-L1 having the amino acid sequence of SEQ ID NO.:18, CDR-L2 having the amino acid sequence of SEQ ID NO.:19 and CDR-L3 having the amino acid sequence of SEQ ID NO.:20. In certain embodiments, the anti-IL17 A/F antibody comprises a heavy chain variable region having the amino acid sequence of SEQ ID NO.:21. In certain embodiments, the anti-IL17 A/F antibody comprises a light chain variable region having the amino acid sequence of SEQ ID NO.:22. In certain embodiments, the anti-IL17 A/F antibody comprises a heavy chain variable region having the amino acid sequence of SEQ ID NO.:21 and a light chain variable region having the amino acid sequence of SEQ ID NO.:22. In certain embodiments, the HIC chromatography step comprises an equilibration buffer and a wash buffer, wherein each of the equilibration buffer and the wash buffer comprise 50 mM sodium acetate pH 5.5. In certain embodiments, the flow-through is monitored by absorbance at 280 nanometers and the flow-through is collected beginning at 0.5 OD and for 10 column volumes. In certain embodiments, the methods further comprise an affinity chromatography step. In certain embodiments, the affinity chromatography is protein A chromatography. In certain embodiments, the methods further comprise a cation exchange chromatography step. In some embodiments, the methods comprise a first Protein A affinity chromatography step and a second cation exchange chromatography step prior to the hydrophobic interaction chromatography (HIC) step. In some embodiments, the affinity chromatography step comprises MABSELECT SURE™ resin, the cation exchange chromatography step comprises POROS 50 HS resin, and the HIC step comprises PHENYL SEPHAROSE™ 6 Fast Flow (high sub) resin. In some embodiments, the affinity chromatography step comprises operating a MABSELECT SURE™ resin-containing column in bind-elute mode; the cation exchange chromatography step comprises operating a POROS 50 HS resin-containing column in bind-elute mode, and the HIC step comprises operating a PHENYL SEPHAROSE™ 6 Fast Flow (High Sub) resin-containing column in flow-through mode.

In still yet another aspect, anti-Abeta monoclonal antibody preparations purified from CHO cells by a process comprising a hydrophobic interaction chromatography (HIC) step are provided. In certain embodiments, the purified preparation comprises the anti-Abeta antibody and a residual amount of hamster PLBL2. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the HIC step comprises PHENYL SEPHAROSE™ 6 Fast Flow (High Sub) resin. In certain embodiments, the HIC step comprises operating a resin-containing column in flow-through mode. In certain embodiments, the HIC step comprises an equilibration buffer and a wash buffer, wherein each of the equilibration buffer and the wash buffer comprise 150 mM sodium acetate pH 5.0. In certain embodiments, the HIC step comprises an equilibration buffer and a wash buffer, wherein each of the equilibration buffer and the wash buffer comprise 150 mM sodium acetate pH 4.0. In certain embodiments, the HIC step comprises an equilibration buffer and a wash buffer, wherein each of the equilibration buffer and the wash buffer comprise 150 mM sodium acetate, 240 mM sodium sulfate pH 4.0. In certain embodiments, the HIC step comprises an equilibration buffer and a wash buffer, wherein each of the equilibration buffer and the wash buffer comprise 150 mM sodium acetate, 240 mM sodium sulfate pH 5.0. In certain embodiments, the load density is 300 g/L. In certain embodiments, the load density is 100 g/L. In certain embodiments, the flow-through is monitored by absorbance at 280 nanometers and the flow-through is collected between 0.5 OD and for 10 column volumes. In certain embodiments, the process further comprises an affinity chromatography step. In certain embodiments, the affinity chromatography is protein A chromatography. In certain embodiments, the process further comprises a mixed mode chromatography step. In certain embodiments, the anti-Abeta antibody comprises three heavy chain CDRs, CDR-H1 having the amino acid sequence of SEQ ID NO.: 23, CDR-H2 having the amino acid sequence of SEQ ID NO.: 24, and CDR-H3 having the amino acid sequence of SEQ ID NO.: 25, and three light chain CDRs, CDR-L1 having the amino acid sequence of SEQ ID NO.: 26, CDR-L2 having the amino acid sequence of SEQ ID NO.: 27, and CDR-L3 having the amino acid sequence of SEQ ID NO.: 28. In certain embodiments, the anti-Abeta antibody comprises a heavy chain variable region having the amino acid sequence of SEQ ID NO.: 29. In certain embodiments, the anti-Abeta antibody comprises a light chain variable region having the amino acid sequence of SEQ ID NO.: 30. In certain embodiments, the anti-Abeta antibody comprises a heavy chain variable region having the amino acid sequence of SEQ ID NO.: 29 and a light chain variable region having the amino acid sequence of SEQ ID NO.: 30. In certain embodiments, the amount of hamster PLBL2 is quantified using an immunoassay or a mass spectrometry assay. In certain embodiments, the immunoassay is a total Chinese hamster ovary protein ELISA or a hamster PLBL2 ELISA. In certain embodiments, the mass spectrometry assay is LC-MS/MS.

In one aspect, anti-IL17 A/F monoclonal antibody preparations isolated and purified from CHO cells by a process comprising a hydrophobic interaction chromatography (HIC) step are provided. In certain embodiments, the purified preparation comprises the anti-IL17 A/F antibody and a residual amount of hamster PLBL2. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the HIC step comprises PHENYL SEPHAROSE™ 6 Fast Flow (High Sub) resin. In certain embodiments, the HIC step comprises operating a resin-containing column in flow-through mode. In certain embodiments, the HIC step comprises an equilibration buffer and a wash buffer, wherein each of the equilibration buffer and the wash buffer comprise 50 mM sodium acetate pH 5.5. In certain embodiments, the flow-through is monitored by absorbance at 280 nanometers and the flow-through is collected between 0.5 OD and for 10 column volumes. In certain embodiments, the process further comprises an affinity chromatography step. In certain embodiments, the affinity chromatography is protein A chromatography. In certain embodiments, the process further comprises a cation exchange chromatography step. In certain embodiments, the anti-IL17 A/F antibody comprises three heavy chain CDRs, CDR-H1 having the amino acid sequence of SEQ ID NO.: 15, CDR-H2 having the amino acid sequence of SEQ ID NO.: 16, and CDR-H3 having the amino acid sequence of SEQ ID NO.: 17, and three light chain CDRs, CDR-L1 having the amino acid sequence of SEQ ID NO.: 18, CDR-L2 having the amino acid sequence of SEQ ID NO.: 19, and CDR-L3 having the amino acid sequence of SEQ ID NO.: 20. In certain embodiments, the anti-IL17 A/F antibody comprises a heavy chain variable region having the amino acid sequence of SEQ ID NO.: 21. In certain embodiments, the anti-IL17 A/F antibody comprises a light chain variable region having the amino acid sequence of SEQ ID NO.: 22. In certain embodiments, the anti-IL17 A/F antibody comprises a heavy chain variable region having the amino acid sequence of SEQ ID NO.: 21 and a light chain variable region having the amino acid sequence of SEQ ID NO.: 32. In certain embodiments, the amount of hamster PLBL2 is quantified using an immunoassay or a mass spectrometry assay. In certain embodiments, the immunoassay is a total Chinese hamster ovary protein ELISA or a hamster PLBL2 ELISA. In certain embodiments, the mass spectrometry assay is LC-MS/MS.

In still another aspect, compositions comprising an anti-Abeta monoclonal antibody purified from CHO cells comprising the anti-Abeta antibody and a residual amount of hamster PLBL2 are provided. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the anti-Abeta antibody is crenezumab. In certain embodiments, the anti-Abeta antibody comprises three heavy chain CDRs, CDR-H1 having the amino acid sequence of SEQ ID NO.: 23, CDR-H2 having the amino acid sequence of SEQ ID NO.:24, and CDR-H3 having the amino acid sequence of SEQ ID NO.:25, and three light chain CDRs, CDR-L1 having the amino acid sequence of SEQ ID NO.:26, CDR-L2 having the amino acid sequence of SEQ ID NO.:27, and CDR-L3 having the amino acid sequence of SEQ ID NO.: 28. In certain embodiments, the anti-Abeta antibody comprises a heavy chain variable region having the amino acid sequence of SEQ ID NO.:29. In certain embodiments, the anti-Abeta antibody comprises a light chain variable region having the amino acid sequence of SEQ ID NO.:30. In certain embodiments, the anti-Abeta antibody comprises a heavy chain variable region having the amino acid sequence of SEQ ID NO.:29 and a light chain variable region having the amino acid sequence of SEQ ID NO.:30.

In yet still another aspect, compositions comprising an anti-IL17 A/F monoclonal antibody purified from CHO cells comprising the anti-IL17 A/F antibody and a residual amount of hamster PLBL2 are provided. In certain embodiments, the composition comprises the anti-IL17 A/F antibody and a residual amount of hamster PLBL2, wherein the amount of hamster PLBL2 is less than 20 ng/mg, or less than 15 ng/mg, or less than 10 ng/mg, or less than 8 ng/mg, or less than 5 ng/mg, or less than 3 ng/mg, or less than 2 ng/mg, or less than 1 ng/mg, or less than 0.5 ng/mg. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the anti-IL17 A/F antibody comprises three heavy chain CDRs, CDR-H1 having the amino acid sequence of SEQ ID NO.:15, CDR-H2 having the amino acid sequence of SEQ ID NO.:16, and CDR-H3 having the amino acid sequence of SEQ ID NO.:17, and three light chain CDRs, CDR-L1 having the amino acid sequence of SEQ ID NO.: 18, CDR-L2 having the amino acid sequence of SEQ ID NO.:19, and CDR-L3 having the amino acid sequence of SEQ ID NO.:20. In certain embodiments, the anti-IL17 A/F antibody comprises a heavy chain variable region having the amino acid sequence of SEQ ID NO.:21. In certain embodiments, the anti-IL17 A/F antibody comprises a light chain variable region having the amino acid sequence of SEQ ID NO.:22. In certain embodiments, the anti-IL17 A/F antibody comprises a heavy chain variable region having the amino acid sequence of SEQ ID NO.:21 and a light chain variable region having the amino acid sequence of SEQ ID NO.:22.

In one aspect, methods of treating an IL-13-mediated disorder comprising administering a treatment composition comprising an anti-IL13 monoclonal antibody purified from CHO cells and a residual amount of hamster PLBL2 are provided. In certain embodiments, the amount of hamster PLBL2 is less than 20 ng/mg. In certain embodiments, the amount of hamster PLBL2 is less than 15 ng/mg. In certain embodiments, the amount of hamster PLBL2 is less than 10 ng/mg. In certain embodiments, the amount of hamster PLBL2 is less than 8 ng/mg. In certain embodiments, the amount of hamster PLBL2 is less than 5 ng/mg. In certain embodiments, the amount of hamster PLBL2 is less than 3 ng/mg. In certain embodiments, the amount of hamster PLBL2 is less than 2 ng/mg. In certain embodiments, the amount of hamster PLBL2 is less than 1 ng/mg. In certain embodiments, the amount of hamster PLBL2 is less than 0.5 ng/mg. In certain embodiments, the amount of hamster PLBL2 is between 0.5 ng/mg and 20 ng/mg, or between 0.5 ng/mg and 15 ng/mg, or between 0.5 ng/mg and 10 ng/mg, or between 0.5 ng/mg and 8 ng/mg, or between 0.5 ng/mg and 5 ng/mg, or between 0.5 ng/mg and 3 ng/mg, or between 0.5. ng/mg and 2 ng/mg, or between 0.5 ng/mg and 1 ng/mg, or between the limit of assay quantitation (LOQ) and 1 ng/mg. In certain embodiments, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6. In certain embodiments, the anti-IL13 antibody comprises a heavy chain variable region having the amino acid sequence of SEQ ID NO.: 7. In certain embodiments, the anti-IL13 antibody comprises a light chain variable region having the amino acid sequence of SEQ ID NO.: 9. In certain embodiments, the anti-IL13 antibody comprises a heavy chain having the amino acid sequence of SEQ ID NO.: 10. In certain embodiments, the anti-IL13 antibody comprises a light chain having the amino acid sequence of SEQ ID NO.: 14. In certain embodiments, the anti-IL13 antibody comprises a heavy chain variable region having the amino acid sequence of SEQ ID NO.: 7 and a light chain variable region having the amino acid sequence of SEQ ID NO.: 9. In certain embodiments, the anti-IL13 antibody comprises a heavy chain having the amino acid sequence of SEQ ID NO.: 10 and a light chain having the amino acid sequence of SEQ ID NO.: 14. In certain embodiments, the treatment composition is administered subcutaneously once every four weeks. In certain embodiments, the treatment composition is administered subcutaneously once every eight weeks. In certain embodiments, the treatment composition is administered subcutaneously once every 12 weeks. In certain embodiments, the patient is treated once every four weeks for at least one month. In certain embodiments, the patient is treated once every four weeks for at least three months. In certain embodiments, the patient is treated once every four weeks for at least six months. In certain embodiments, the patient is treated once every four weeks for at least nine months. In certain embodiments, the patient is treated once every four weeks for at least 12 months. In certain embodiments, the patient is treated once every four weeks for at least 18 months. In certain embodiments, the patient is treated once every four weeks for at least two years. In certain embodiments, the patient is treated once every four weeks for more than two years. In certain embodiments, the IL-13-mediated disorder is asthma. In certain embodiments, the IL-13-mediated disorder is idiopathic pulmonary fibrosis. In certain embodiments, the IL-13-mediated disorder is atopic dermatitis. In certain embodiments, the IL-13-mediated disorder is selected from allergic asthma, non-allergic asthma, allergic rhinitis, allergic conjunctivitis, eczema, urticaria, food allergies, chronic obstructive pulmonary disease, ulcerative colitis, RSV infection, uveitis, scleroderma, and osteoporosis.

In another aspect, administration of a treatment composition to a patient according to any of the methods described above is less immunogenic for hamster PLBL2 compared to administration of a reference composition, wherein the reference composition comprises an anti-IL13 monoclonal antibody purified from Chinese hamster ovary host cells and a residual amount of hamster PLBL2 of greater than 30 ng/mg. In certain embodiments, the amount of hamster PLBL2 in the reference composition is greater than 50 ng/mg. In certain embodiments, the amount of hamster PLBL2 in the reference composition is greater than 100 ng/mg. In certain embodiments, the amount of hamster PLBL2 in the reference composition is greater than 200 ng/mg. In certain embodiments, the amount of hamster PLBL2 in the reference composition is greater than 300 ng/mg. In certain embodiments, the amount of hamster PLBL2 in the reference composition is between 30 ng/mg and 300 ng/mg, or between 30 ng/mg and 200 ng/mg, or between 30 ng/mg and 100 ng/mg, or between 30 ng/mg and 50 ng/mg.

BRIEF DESCRIPTION OF THE DRAWINGS

(FIG. 1A) Caprylic acid precipitation of Protein A pool at pH 4.5; (FIG. 1B) Caprylic acid precipitation of Protein A pool at pH 5.0. CHOP levels in ng/mg are indicated along the vertical axis; percentage of caprylic acid is shown along the horizontal axis, each bar represents the value from 2-fold serial dilution.

(FIG. 3A) OCTYL-SEPHAROSE® Fast Flow resin; (FIG. 3B) PHENYL SEPHAROSE™ 6 Fast Flow (low sub) resin; (FIG. 3C) BUTYL-SEPHAROSE® 4 Fast Flow resin; (FIG. 3D) PHENYL SEPHAROSE™ 6 Fast Flow (high sub) resin; highest dilution CHOP (in ppm) is shown on the vertical axis and sodium sulfate concentration is shown on the horizontal axis; pH (5.5, 6.0, 7.0, or 8.0 is indicated by the legend.

DETAILED DESCRIPTION

Figure 1A:
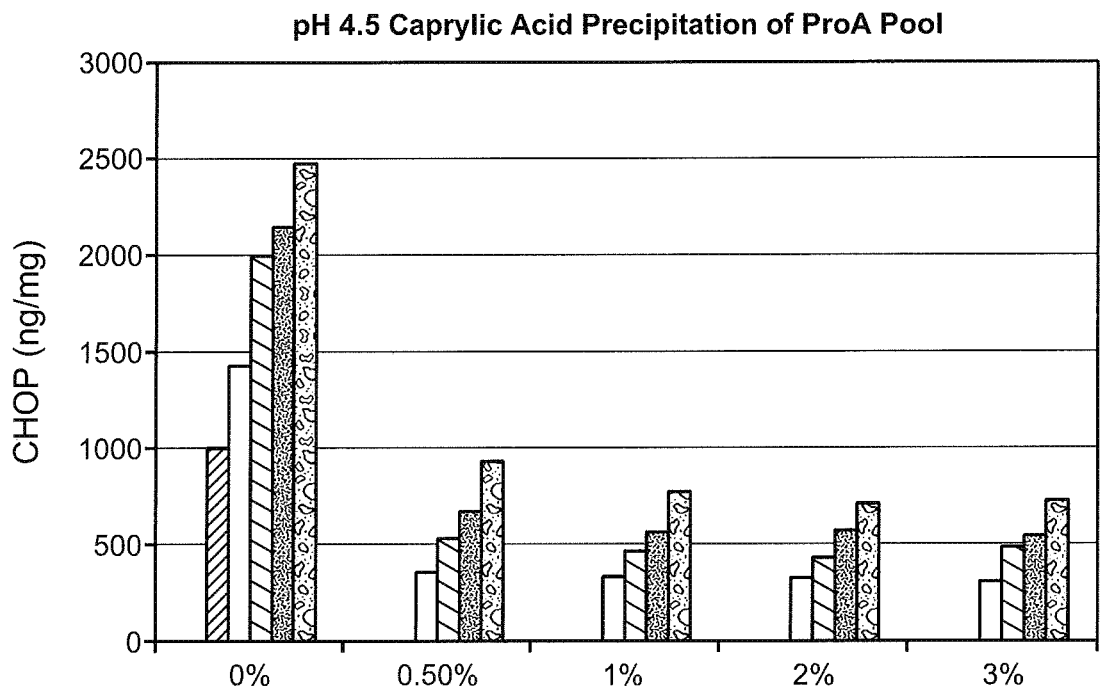
FIGS. 1A-1B show total CHOP levels in caprylic acid-treated Protein A pools of anti-IL13 MAb as described in Example 2.
Figure 1B:
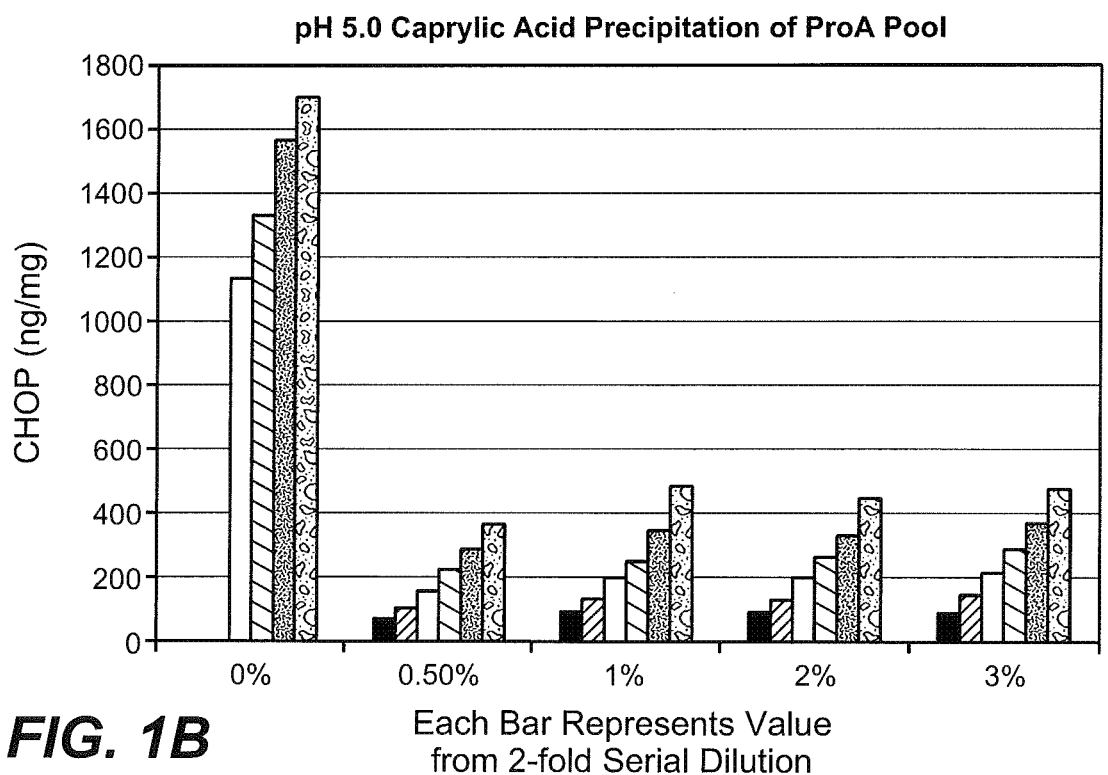

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" or an "antibody" includes a plurality of proteins or antibodies, respectively; reference to "a cell" includes mixtures of cells, and the like.

The term "detecting" is used herein in the broadest sense to include both qualitative and quantitative measurements of a target molecule. Detecting includes identifying the mere presence of the target molecule in a sample as well as determining whether the target molecule is present in the sample at detectable levels.

A "sample" refers to a small portion of a larger quantity of material. Generally, testing according to the methods described herein is performed on a sample. The sample is typically obtained from a recombinant polypeptide preparation obtained, for example, from cultured host cells. A sample may be obtained from, for example but not limited to, harvested cell culture fluid, from an in-process pool at a certain step in a purification process, or from the final purified product.

The term "product" as described herein is the substance to be purified by various chromatographic methods; for example, a polypeptide.

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

The term "epitope tagged" when used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (in certain instances, between about 10 and 20 amino acid residues).

"Active" or "activity" for the purposes herein refers to form(s) of a polypeptide which retain a biological and/or an immunological activity of interest, wherein "biological" activity refers to a biological function (either inhibitory or stimulatory) caused by the polypeptide other than the ability to induce the production of an antibody against an antigenic epitope possessed by the polypeptide and an "immunological" activity refers to the ability to induce the production of an antibody against an antigenic epitope possessed by the polypeptide.

The term "antagonist" is used in the broadest sense, and includes any molecule that partially or fully blocks, inhibits, or neutralizes a biological activity of a native polypeptide, e.g., a cytokine. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, and the like. Methods for identifying agonists or antagonists of a polypeptide may comprise contacting a polypeptide with a candidate agonist or antagonist molecule and measuring a detectable change in one or more biological activities normally associated with the polypeptide.

A polypeptide "which binds" an antigen of interest, e.g. a tumor-associated polypeptide antigen target, is one that binds the antigen with sufficient affinity such that the polypeptide is useful as an assay reagent, a diagnostic and/or therapeutic agent in targeting a sample containing the antigen, a cell or tissue expressing the antigen, and does not significantly cross-react with other polypeptides.

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "antibody" herein is used in the broadest sense and encompasses various antibody structures, including but not limited to monoclonal antibodies, polyclonal antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a (3-sheet configuration, connected by three hypervariable regions, which form loops connecting, and in some cases forming part of, the (3-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "hypervariable region" when used herein refers to certain amino acid residues of an antibody that are responsible for antigen binding. The hypervariable region may comprise amino acid residues from a "complementarity determining region" or "CDR" as discussed above (e.g., around about residues 24-34 (L1), 50-56 (L2) and 89-97 (L3) in the $V_L$, and around about 31-35B (H1), 50-65 (H2)

and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 μM to 0.001 pM, 3 μM to 0.001 pM, 1 μM to 0.001 pM, 0.5 μM to 0.001 pM, or 0.1 μM to 0.001 pM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "anti-IL-13 antibody" and "an antibody that binds to IL-13" refer to an antibody that is capable of binding IL-13 with sufficient affinity such that the antibody is useful as a diagnostic and/or therapeutic agent in targeting IL-13. In some embodiments, the extent of binding of an anti-IL-13 antibody to an unrelated, non-IL-13 protein is less than about 10% of the binding of the antibody to IL-13 as measured, e.g., by a radioimmunoassay (RIA). In certain embodiments, an antibody that binds to IL-13 has a dissociation constant (Kd) of ≤1 μM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). In certain embodiments, an anti-IL-13 antibody binds to an epitope of IL-13 that is conserved among IL-13 from different species.

"IL-13 mediated disorder" means a disorder associated with excess IL-13 levels or activity in which atypical symptoms may manifest due to the levels or activity of IL-13 locally and/or systemically in the body. Examples of IL-13 mediated disorders include: cancers (e.g., non-Hodgkin's lymphoma, glioblastoma), atopic dermatitis, allergic rhinitis, asthma, fibrosis, inflammatory bowel disease, Crohn's disease, lung inflammatory disorders (including pulmonary fibrosis such as IPF), COPD, and hepatic fibrosis.

The term "respiratory disorder" includes, but is not limited to, asthma (e.g., allergic and non-allergic asthma (e.g., due to infection, e.g., with respiratory syncytial virus (RSV), e.g., in younger children)); bronchitis (e.g., chronic bronchitis); chronic obstructive pulmonary disease (COPD) (e.g., emphysema (e.g., cigarette-induced emphysema); conditions involving airway inflammation, eosinophilia, fibrosis and excess mucus production, e.g., cystic fibrosis, pulmonary fibrosis, and allergic rhinitis. Examples of diseases that can be characterized by airway inflammation, excessive airway secretion, and airway obstruction include asthma, chronic bronchitis, bronchiectasis, and cystic fibrosis.

The term "therapeutic agent" refers to any agent that is used to treat a disease. A therapeutic agent may be, for example, a polypeptide(s) (e.g., an antibody, an immunoadhesin or a peptibody), an aptamer or a small molecule that can bind to a protein or a nucleic acid molecule that can bind to a nucleic acid molecule encoding a target (i.e., siRNA), and the like.

A "naked antibody" is an antibody (as herein defined) that is not conjugated to a heterologous molecule, such as a cytotoxic moiety or radiolabel.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "sequential" as used herein with regard to chromatography refers to having a first chromatography followed by a second chromatography. Additional steps may be included between the first chromatography and the second chromatography.

The term "continuous" as used herein with regard to chromatography refers to having a first chromatography material and a second chromatography material either directly connected or some other mechanism which allows for continuous flow between the two chromatography materials.

"Impurities" and "contaminants" refer to materials that are different from the desired polypeptide product. Impurities and contaminants include, without limitation: host cell materials, such as CHOP, including single CHOP species; leached Protein A; nucleic acid; a variant, fragment, aggregate or derivative of the desired polypeptide; another polypeptide; endotoxin; viral contaminant; cell culture media component, etc. In some examples, the contaminant may be a host cell protein (HCP) from, for example but not limited to, a bacterial cell such as an *E. coli* cell, an insect cell, a prokaryotic cell, a eukaryotic cell, a yeast cell, a mammalian cell, an avian cell, a fungal cell.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid ("HCCF")) comprising a protein of interest such as an antibody or immunoadhesin expressed in a CHO cell.) The amount of CHOP present in a mixture comprising a protein of interest provides a measure of the degree of purity for the protein of interest. HCP or CHOP includes, but is not limited to, a protein of interest expressed by the host cell, such as a CHO host cell. Typically, the amount of CHOP in a protein mixture is expressed in parts per million relative to the amount of the protein of interest in the mixture. It is understood that where the host cell is another mammalian cell type, an *E. coli*, a yeast, an insect cell, or a plant cell, HCP refers to the proteins, other than target protein, found in a lysate of the host cell.

The term "parts per million" or "ppm" are used interchangeably herein to refer to a measure of purity of the protein of interest purified by a method of the invention. The units ppm refer to the amount of HCP or CHOP in nanograms/milliliter per protein of interest in milligrams/milliliter (i.e., CHOP ppm=(CHOP ng/ml)/(protein of interest mg/ml), where the proteins are in solution). Where the proteins are dried (such as by lyophilization), ppm refers to (CHOP ng)/(protein of interest mg)). Impurities may also be expressed as "ng/mg" which is used interchangeably with ppm.

By "purifying" a polypeptide from a composition comprising the polypeptide and one or more impurities is meant increasing the degree of purity of the polypeptide in the composition by removing (completely or partially) at least one impurity from the composition.

A "purification step" may be part of an overall purification process resulting in a "homogeneous" composition, which is used herein to refer to a composition comprising less than 100 ppm HCP (100 ng/mg) in a composition comprising the protein of interest, or less than 90 ppm (90 ng/mg), or less than 80 ppm (80 ng/mg), or less than 70 ppm (70 ng/mg), or less than 60 ppm (60 ng/mg), or less than 50 ppm 50 ng/mg), or less than 40 ppm (40 ng/mg), or less than 30 ppm (30 ng/mg), or less than 20 ppm (20 ng/mg), or less than 10 ppm (10 ng/mg), or less than 5 ppm (5 ng/mg), or less than 3 ppm (3 ng/mg) or less than 1 ppm (1 ng/mg). In certain embodiments, the HCP is a single HCP species. In one embodiment, the single HCP species is hamster PLBL2.

The "composition" to be purified herein comprises the polypeptide of interest and one or more impurities or contaminants. The composition may be "partially purified" (i.e. having been subjected to one or more purification steps or may be obtained directly from a host cell or organism producing the polypeptide (e.g. the composition may comprise harvested cell culture fluid).

The terms "Protein A" and "ProA" are used interchangeably herein and encompasses Protein A recovered from a native source thereof, Protein A produced synthetically (e.g. by peptide synthesis or by recombinant techniques), and variants thereof which retain the ability to bind proteins which have a CH2/CH3 region, such as an Fc region. Protein A can be purchased commercially from various sources. Protein A is generally immobilized on a solid phase support material. The term "ProA" also refers to an affinity chromatography resin or column containing chromatographic solid support matrix to which is covalently attached Protein A.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "affinity chromatography" and "protein affinity chromatography" are used interchangeably herein and refer to a protein separation technique in which a protein of interest or antibody of interest is reversibly and specifically bound to a biospecific ligand. Typically, the biospecific ligand is covalently attached to a chromatographic solid phase material and is accessible to the protein of interest in solution as the solution contacts the chromatographic solid phase material. The protein of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody.

The terms "non-affinity chromatography" and "non-affinity purification" refer to a purification process in which affinity chromatography is not utilized. Non-affinity chromatography includes chromatographic techniques that rely on non-specific interactions between a molecule of interest (such as a protein, e.g. antibody) and a solid phase matrix.

The term "specific binding" as used herein in the context of chromatography, such as to describe interactions between a molecule of interest and a ligand bound to a solid phase matrix, refers to the generally reversible binding of a protein of interest to a ligand through the combined effects of spatial complementarity of protein and ligand structures at a binding site coupled with electrostatic forces, hydrogen bonding, hydrophobic forces, and/or van der Waals forces at the binding site. The greater the spatial complementarity and the stronger the other forces at the binding site, the greater will be the binding specificity of a protein for its respective ligand. Non-limiting examples of specific binding includes antibody-antigen binding, enzyme-substrate binding, enzyme-cofactor binding, metal ion chelation, DNA binding protein-DNA binding, regulatory protein-protein interactions, and the like. Typically, in affinity chromatography specific binding occurs with an affinity of about $10^{-4}$ to $10^{-8}$ M in free solution.

The term "non-specific binding" as used herein in the context of chromatography, such as to describe interactions between a molecule of interest and a ligand or other compound bound to a solid phase matrix, refers to binding of a protein of interest to the ligand or compound on a solid phase matrix through electrostatic forces, hydrogen bonding, hydrophobic forces, and/or van der Waals forces at an interaction site, but lacking structural complementarity that enhances the effects of the non-structural forces. Examples of non-specific interactions include, but are not limited to, electrostatic, hydrophobic, and van der Waals forces as well as hydrogen bonding.

A "salt" is a compound formed by the interaction of an acid and a base. Exemplary salts include, but are not limited to, acetate (e.g. sodium acetate), citrate (e.g. sodium citrate), chloride (e.g. sodium chloride), sulphate (e.g. sodium sulphate), or a potassium salt.

As used herein, "solvent" refers to a liquid substance capable of dissolving or dispersing one or more other substances to provide a solution. Solvents include aqueous and organic solvents, where certain organic solvents include a non-polar solvent, ethanol, methanol, isopropanol, acetonitrile, hexylene glycol, propylene glycol, and 2,2-thiodiglycol.

The term "detergent" refers to ionic and nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polysorbate, such as polysorbate 20 (TWEEN 20®) or polysorbate 80 (TWEEN 80®).

A "polymer" herein is a molecule formed by covalent linkage of two or more monomers, where the monomers are not amino acid residues. Examples of polymers include, but are not limited to, polyethyl glycol, polypropyl glycol, and copolymers (e.g. PLURONICS™, PF68 etc), polyethylene glycol (PEG), e.g. PEG 400 and PEG 8000.

The term "ion-exchange" and "ion-exchange chromatography" refers to the chromatographic process in which a solute of interest (such as a protein) in a mixture interacts with a charged compound linked (such as by covalent attachment) to a solid phase ion exchange material such that the solute of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode chromatography.

The phrase "ion exchange material" refers to a solid phase that is negatively charged (i.e. a cation exchange resin) or positively charged (i.e. an anion exchange resin). The charge may be provided by attaching one or more charged ligands to the solid phase, e.g. by covalent linking. Alternatively, or in addition, the charge may be an inherent property of the solid phase (e.g. as is the case for silica, which has an overall negative charge).

By "solid phase" is meant a non-aqueous matrix to which one or more charged ligands can adhere. The solid phase may be a purification column, a discontinuous phase of discrete particles, a membrane, or filter etc. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above.

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include, but are not limited to, carboxy-methyl-cellulose, sulphopropyl (SP) immobilized on agarose (e.g. SP-SEPHAROSE FAST FLOW (or SP-SEPHAROSE HIGH PERFORMANCE) and sulphonyl immobilized on agarose (e.g. S-SEPHAROSE FAST FLOW), and POROS®HS.

A "mixed mode ion exchange resin" refers to a solid phase which is covalently modified with cationic, anionic, and hydrophobic moieties. Mixed mode ion exchange is also referred to as "multimodal ion exchange." Commercially available mixed mode ion exchange resin are available, e.g., BAKERBOND ABX containing weak cation exchange groups, a low concentration of anion exchange groups, and hydrophobic ligands attached to a silica gel solid phase support matrix. Additional exemplary mixed mode ion exchange resins include, but are not limited to, CAPTO™ Adhere resin, QMA resin, CAPTO™ MMC resin, MEP HyperCel resin, HEA HyperCel resin, PPA HyperCel resin, or ChromaSorb membrane or Sartobind STIC. In some embodiments, the mixed mode material is CAPTO™ Adhere resin.

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPHADEX and FAST Q SEPHAROSE™ and Q SEPHAROSE™ FAST FLOW.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). In certain instances, the buffer has a pH in the range from about 2 to about 9, alternatively from about 3 to about 8, alternatively from about 4 to about 7 alternatively from about 5 to about 7. Non-limiting examples of buffers that will control the pH in this range include MES, MOPS, MOPSO, Tris, HEPES, phosphate, acetate, citrate, succinate, and ammonium buffers, as well as combinations of these.

The term "hydrophobic interaction chromatography" or "HIC" is used herein to refer to a chromatographic process that separates molecule based on their hydrophobicity. Exemplary resins that can be used for HIC include, but are not limited to phenyl-, butyl-, octyl-SEPHAROSE, BUTYL-SEPHAROSE® 4 Fast Flow, PHENYL SEPHAROSE™ High Performance, PHENYL SEPHAROSE™ 6 Fast Flow (low sub), and PHENYL SEPHAROSE™ 6 Fast Flow (high sub). Typically, sample molecules in a high salt buffer are loaded onto the HIC column. The salt in the buffer interacts with water molecules to reduce the solvation of the molecules in solution, thereby exposing hydrophobic regions in the sample molecules which are consequently adsorbed by the HIC column. The more hydrophobic the molecule, the less salt needed to promote binding. Typically, a decreasing salt gradient is used to elute samples from the column. As the ionic strength decreases, the exposure of the hydrophilic regions of the molecules increases and molecules elute from the column in order of increasing hydrophobicity. Sample elution may also be achieved by the addition of mild organic modifiers or detergents to the elution buffer.

The "loading buffer" is that which is used to load the composition comprising the polypeptide molecule of interest and one or more impurities onto the ion exchange resin. The loading buffer has a conductivity and/or pH such that the polypeptide molecule of interest (and generally one or more impurities) is/are bound to the ion exchange resin or such that the protein of interest flows through the column while the impurities bind to the resin.

The "intermediate buffer" is used to elute one or more impurities from the ion exchange resin, prior to eluting the polypeptide molecule of interest. The conductivity and/or pH of the intermediate buffer is/are such that one or more impurity is eluted from the ion exchange resin, but not significant amounts of the polypeptide of interest.

The term "wash buffer" when used herein refers to a buffer used to wash or re-equilibrate the ion exchange resin, prior to eluting the polypeptide molecule of interest. In certain instances, for convenience, the wash buffer and loading buffer may be the same, but this is not required.

The "elution buffer" is used to elute the polypeptide of interest from the solid phase. The conductivity and/or pH of the elution buffer is/are such that the polypeptide of interest is eluted from the ion exchange resin.

A "regeneration buffer" may be used to regenerate the ion exchange resin such that it can be re-used. The regeneration buffer has a conductivity and/or pH as required to remove substantially all impurities and the polypeptide of interest from the ion exchange resin.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSeimens per centimeter (mS/cm), and can be measured using a conductivity meter sold, e.g., by Orion. The conductivity of a solution may be altered by changing the concentration of ions therein. For example, the concentration of a buffering agent and/or concentration of a salt (e.g. NaCl or KCl) in the solution may be altered in order to achieve the desired conductivity.

The "pI" or "isoelectric point" of a polypeptide refer to the pH at which the polypeptide's positive charge balances its negative charge. pI can be calculated from the net charge of the amino acid residues or sialic acid residues of attached carbohydrates of the polypeptide or can be determined by isoelectric focusing.

By "binding" a molecule to an ion exchange material is meant exposing the molecule to the ion exchange material under appropriate conditions (pH/conductivity) such that the molecule is reversibly immobilized in or on the ion exchange material by virtue of ionic interactions between the molecule and a charged group or charged groups of the ion exchange material.

By "washing" the ion exchange material is meant passing an appropriate buffer through or over the ion exchange material.

To "elute" a molecule (e.g. polypeptide or impurity) from an ion exchange material is meant to remove the molecule therefrom by altering the ionic strength of the buffer surrounding the ion exchange material such that the buffer competes with the molecule for the charged sites on the ion exchange material.

"Ultrafiltration" is a form of membrane filtration in which hydrostatic pressure forces a liquid against a semipermeable membrane. Suspended solids and solutes of high molecular weight are retained, while water and low molecular weight solutes pass through the membrane. In some examples, ultrafiltration membranes have pore sizes in the range of 1 to 100 nm. The terms "ultrafiltration membrane" and "ultrafiltration filter" may be used interchangeably.

"Diafiltration" is a method that incorporates ultrafiltration membranes to remove salts or other microsolutes from a solution. Small molecules are separated from a solution while retaining larger molecules in the retentate. The process selectively utilizes permeable (porous) membrane filters to separate the components of solutions and suspensions based on their molecular size.

As used herein, "filtrate" refers to that portion of a sample that passes through the filtration membrane.

As used herein, "retentate" refers to that portion of a sample that is substantially retained by the filtration membrane.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies are used to delay development of a disease or to slow the progression of a disease.

Reference to "about" a value or parameter herein includes (and describes) variations that are directed to that value or parameter per se. For example, description referring to "about X" includes description of "X".

Anti-IL13 Antibodies

In some embodiments, isolated and purified antibodies that bind IL-13 are provided. Exemplary anti-IL13 antibodies are known and include, for example, but not limited to, lebrikizumab, IMA-026, IMA-638 (also referred to as, anrukinzumab, INN No. 910649-32-0; QAX-576), tralokinumab (also referred to as CAT-354, CAS No. 1044515-88-9); AER-001, ABT-308 (also referred to as humanized 13C5.5 antibody. Examples of such anti-IL13 antibodies and other inhibitors of IL13 are disclosed, for example, in WO 2005/062967, WO2008/086395, WO2006/085938, U.S. Pat. Nos. 7,615,213, 7,501,121, WO2007/036745, WO2010/073119, WO2007/045477. In one embodiment, the anti-IL13 antibody is a humanized IgG4 antibody. In one embodiment, the anti-IL13 antibody is lebrikizumab. In one embodiment, the anti-IL13 antibody comprises three heavy chain CDRs, CDR-H1 (SEQ ID NO.: 1), CDR-H2 (SEQ ID NO.: 2), and CDR-H3 (SEQ ID NO.: 3). In one embodiment, the anti-IL13 antibody comprises three light chain CDRS, CDR-L1 (SEQ ID NO.: 4), CDR-L2 (SEQ ID NO.: 5), and CDR-L3 (SEQ ID NO.: 6). In one embodiment, the anti-IL13 antibody comprises three heavy chain CDRs and three light chain CDRs, CDR-H1 (SEQ ID NO.: 1), CDR-H2 (SEQ ID NO.: 2), CDR-H3 (SEQ ID NO.: 3), CDR-L1 (SEQ ID NO.: 4), CDR-L2 (SEQ ID NO.: 5), and CDR-L3 (SEQ ID NO.: 6). In one embodiment, the anti-IL13 antibody comprises a variable heavy chain region, VH, having an amino acid sequence selected from SEQ ID NOs. 7 and 8. In one embodiment, the anti-IL13 antibody comprises a variable light chain region, VL, having the amino acid sequence of SEQ ID NO.: 9. In one embodiment, the anti-IL13 antibody comprises a variable heavy chain region, VH, having an amino acid sequence selected from SEQ ID NOs. 7 and 8 and a variable light chain region, VL, having an amino acid sequence of SEQ ID NO.: 9. In one embodiment, the anti-IL13 antibody comprises a heavy chain having the amino acid sequence of SEQ ID NO.: 10 or SEQ ID NO.: 11 or SEQ ID NO.: 12 or SEQ ID NO.: 13. In one embodiment, the anti-IL13 antibody comprises a light chain having the amino acid sequence of SEQ ID NO.: 14. In one embodiment, the anti-IL13 antibody comprises a heavy chain having an amino acid sequence selected from SEQ ID NO.: 10, SEQ ID NO.: 11, SEQ ID NO.: 12, and SEQ ID NO.: 13 and a light chain having the amino acid sequence of SEQ ID NO.: 14.

In another aspect, an anti-IL-13 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO.: 8. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to human IL-13. In certain embodiments, a total of 1 to 10 amino acids have been substituted, altered inserted and/or deleted in SEQ ID NO.: 8. In certain embodiments, substitutions, insertions, or deletions occur in regions outside the CDRs (i.e., in the FRs). Optionally, the anti-IL13 antibody comprises the VH sequence in SEQ ID NO.: 8, including post-translational modifications of that sequence.

In another aspect, an anti-IL-13 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO.: 9. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to IL-13. In certain embodiments, a total of 1 to 10 amino acids have been substituted, inserted and/or deleted in SEQ ID NO.: 9. In certain embodiments, the substitutions, insertions, or deletions occur in regions outside the CDRs (i.e., in the FRs). Optionally, the anti-IL13 antibody comprises the VL sequence in SEQ ID NO.: 9, including post-translational modifications of that sequence.

In yet another embodiment, the anti-IL-13 antibody comprises a VL region having at least 90%, 91%, 92%, 93%, 94%, 95%, 96%, 97%, 98%, 99%, or 100% sequence identity to the amino acid sequence of SEQ ID NO.: 9 and a VH region having at least 90%, 91%, 92%, 93%, 94%, 95%, 96%, 97%, 98%, 99%, or 100% sequence identity to the amino acid sequence of SEQ ID NO.: 8.

The table below shows the amino acid sequences of the CDR-H1, CDR-H2, CDR-H3, CDR-L1, CDR-L2, and CDR-L3 regions of lebrikizumab, along with VH, VL, heavy chain sequences and light chain sequences. As indicated in Table 1 below, VH and the heavy chain may include an N-terminal glutamine and the heavy chain may also include a C-terminal lysine. As is well known in the art, N-terminal glutamine residues can form pyroglutamate and C-terminal lysine residues can be clipped during manufacturing processes.

TABLE 1

Anti-IL13 antibody (lebrikizumab) amino acid sequences.

| | |
|---|---|
| CDR-H1 (SEQ ID NO.: 1) | Ala Tyr Ser Val Asn |
| CDR-H2 (SEQ ID NO.: 2) | Met Ile Trp Gly Asp Gly Lys Ile Val Tyr Asn Ser Ala Leu Lys Ser |
| CDR-H3 (SEQ ID NO.: 3) | Asp Gly Tyr Tyr Pro Tyr Ala Met Asp Asn |
| CDR-L1 (SEQ ID NO.: 4) | Arg Ala Ser Lys Ser Val Asp Ser Tyr Gly Asn Ser Phe Met His |
| CDR-L2 (SEQ ID NO.: 5) | Leu Ala Ser Asn Leu Glu Ser |
| CDR-L3 (SEQ ID NO.: 6) | Gln Gln Asn Asn Glu Asp Pro Arg Thr |
| VH (SEQ ID NO.: 7) | Val Thr Leu Arg Glu Ser Gly Pro Ala Leu Val Lys Pro Thr Gln Thr Leu Thr Leu Thr Cys Thr Val Ser Gly Phe Ser Leu Ser Ala Tyr Ser Val Asn Trp Ile Arg Gln Pro Pro Gly Lys Ala Leu Glu Trp Leu Ala Met Ile Trp Gly Asp Gly Lys Ile Val Tyr Asn Ser Ala Leu Lys Ser Arg Leu Thr Ile Ser Lys Asp Thr Ser Lys Asn Gln Val Val Leu Thr Met Thr Asn Met Asp Pro Val Asp Thr Ala Thr Tyr Tyr Cys Ala Gly Asp Gly Tyr Tyr Pro Tyr Ala Met Asp Asn Trp Gly Gln Gly Ser Leu Val Thr Val Ser Ser |
| VH (SEQ ID NO.: 8) | Gln Val Thr Leu Arg Glu Ser Gly Pro Ala Leu Val Lys Pro Thr Gln Thr Leu Thr Leu Thr Cys Thr Val Ser Gly Phe Ser Leu Ser Ala Tyr Ser Val Asn Trp Ile Arg Gln Pro Pro Gly Lys Ala Leu Glu Trp Leu Ala Met Ile Trp Gly Asp Gly Lys Ile Val Tyr Asn Ser Ala Leu Lys Ser Arg Leu Thr Ile Ser Lys Asp Thr Ser Lys Asn Gln Val Val Leu Thr Met Thr Asn Met Asp Pro Val Asp Thr Ala Thr Tyr Tyr Cys Ala Gly Asp Gly Tyr Tyr Pro Tyr Ala Met Asp Asn Trp Gly Gln Gly Ser Leu Val Thr Val Ser Ser |
| VL (SEQ ID NO.: 9) | Asp Ile Val Met Thr Gln Ser Pro Asp Ser Leu Ser Val Ser Leu Gly Glu Arg Ala Thr Ile Asn Cys Arg Ala Ser Lys Ser Val Asp Ser Tyr Gly Asn Ser Phe Met His Trp Tyr Gln Gln Lys Pro Gly Gln Pro Pro Lys Leu Leu Ile Tyr Leu Ala Ser Asn Leu Glu Ser Gly Val Pro Asp Arg Phe Ser Gly Ser Gly Ser Gly Thr Asp Phe Thr Leu Thr Ile Ser Ser Leu Gln Ala Glu Asp Val Ala Val Tyr Tyr Cys Gln Gln Asn Asn Glu Asp Pro Arg Thr Phe Gly Gly Gly Thr Lys Val Glu Ile Lys Arg |
| H Chain (SEQ ID NO.: 10) | VTLRESGPA LVKPTQTLTL TCTVSGFSLS AYSVNWIRQP PGKALEWLAM IWGDGKIVYN SALKSRLTIS KDTSKNQVVL TMTNMDPVDT ATYYCAGDGY YPYAMDNWGQ GSLVTVSSAS TKGPSVFPLA PCSRSTSEST AALGCLVKDY FPEPVTVSWN SGALTSGVHT FPAVLQSSGL YSLSSVVTVP SSSLGTKTYT |

TABLE 1-continued

Anti-IL13 antibody (lebrikizumab) amino acid sequences.

|  |  |
|---|---|
|  | CNVDHKPSNT KVDKRVESKY GPPCPPCPAP EFLGGPSVFL FPPKPKDTLM<br>ISRTPEVTCV VVDVSQEDPE VQFNWYVDGV EVHNAKTKPR EEQFNSTYRV<br>VSVLTVLHQD WLNGKEYKCK VSNKGLPSSI EKTISKAKGQ PREPQVYTLP<br>PSQEEMTKNQ VSLTCLVKGF YPSDIAVEWE SNGQPENNYK TTPPVLDSDG<br>SFFLYSRLTV DKSRWQEGNV FSCSVMHEAL HNHYTQKSLS LSLG |
| H Chain<br>(SEQ ID<br>NO.: 11) | QVTLRESGPA LVKPTQTLTL TCTVSGFSLS AYSVNWIRQP PGKALEWLAM<br>IWGDGKIVYN SALKSRLTIS KDTSKNQVVL TMTNMDPVDT ATYYCAGDGY<br>YPYAMDNWGQ GSLVTVSSAS TKGPSVFPLA PCSRSTSEST AALGCLVKDY<br>FPEPVTVSWN SGALTSGVHT FPAVLQSSGL YSLSSVVTVP SSSLGTKTYT<br>CNVDHKPSNT KVDKRVESKY GPPCPPCPAP EFLGGPSVFL FPPKPKDTLM<br>ISRTPEVTCV VVDVSQEDPE VQFNWYVDGV EVHNAKTKPR EEQFNSTYRV<br>VSVLTVLHQD WLNGKEYKCK VSNKGLPSSI EKTISKAKGQ PREPQVYTLP<br>PSQEEMTKNQ VSLTCLVKGF YPSDIAVEWE SNGQPENNYK TTPPVLDSDG<br>SFFLYSRLTV DKSRWQEGNV FSCSVMHEAL HNHYTQKSLS LSLG |
| H Chain<br>(SEQ ID<br>NO.: 12) | VTLRESGPA LVKPTQTLTL TCTVSGFSLS AYSVNWIRQP PGKALEWLAM<br>IWGDGKIVYN SALKSRLTIS KDTSKNQVVL TMTNMDPVDT ATYYCAGDGY<br>YPYAMDNWGQ GSLVTVSSAS TKGPSVFPLA PCSRSTSEST AALGCLVKDY<br>FPEPVTVSWN SGALTSGVHT FPAVLQSSGL YSLSSVVTVP SSSLGTKTYT<br>CNVDHKPSNT KVDKRVESKY GPPCPPCPAP EFLGGPSVFL FPPKPKDTLM<br>ISRTPEVTCV VVDVSQEDPE VQFNWYVDGV EVHNAKTKPR EEQFNSTYRV<br>VSVLTVLHQD WLNGKEYKCK VSNKGLPSSI EKTISKAKGQ PREPQVYTLP<br>PSQEEMTKNQ VSLTCLVKGF YPSDIAVEWE SNGQPENNYK TTPPVLDSDG<br>SFFLYSRLTV DKSRWQEGNV FSCSVMHEAL HNHYTQKSLS LSLGK |
| H Chain<br>(SEQ ID<br>NO.: 13) | QVTLRESGPA LVKPTQTLTL TCTVSGFSLS AYSVNWIRQP PGKALEWLAM<br>IWGDGKIVYN SALKSRLTIS KDTSKNQVVL TMTNMDPVDT ATYYCAGDGY<br>YPYAMDNWGQ GSLVTVSSAS TKGPSVFPLA PCSRSTSEST AALGCLVKDY<br>FPEPVTVSWN SGALTSGVHT FPAVLQSSGL YSLSSVVTVP SSSLGTKTYT<br>CNVDHKPSNT KVDKRVESKY GPPCPPCPAP EFLGGPSVFL FPPKPKDTLM<br>ISRTPEVTCV VVDVSQEDPE VQFNWYVDGV EVHNAKTKPR EEQFNSTYRV<br>VSVLTVLHQD WLNGKEYKCK VSNKGLPSSI EKTISKAKGQ PREPQVYTLP<br>PSQEEMTKNQ VSLTCLVKGF YPSDIAVEWE SNGQPENNYK TTPPVLDSDG<br>SFFLYSRLTV DKSRWQEGNV FSCSVMHEAL HNHYTQKSLS LSLGK |
| L Chain<br>(SEQ ID<br>NO.: 14) | DIVMTQSPDS LSVSLGERAT INCRASKSVD SYGNSFMHWY QQKPGQPPKL<br>LIYLASNLES GVPDRFSGSG SGTDFTLTIS SLQAEDVAVY YCQQNNEDPR<br>TFGGGTKVEI KRTVAAPSVF IFPPSDEQLK SGTASVVCLL NNFYPREAKV<br>QWKVDNALQS GNSQESVTEQ DSKDSTYSLS STLTLSKADY EKHKVYACEV<br>THQGLSSPVT KSFNRGEC |

Other Recombinant Polypeptides

Recombinant polypeptides produced in CHO cells may be purified according to the methods described herein to remove or reduce levels of hamster PLBL2 such that only residual amounts or an undetectable amount remain. Such polypeptides include, without limitation, growth factors, cytokines, immunoglobulins, antibodies, peptibodies and the like.

Certain exemplary antibodies include antibodies to Abeta, antibodies to IL17A/F and antibodies to CMV. Exemplary anti-Abeta antibodies and methods of producing such antibodies have been described previously, for example, in WO2008011348, WO2007068429, WO2001062801, and WO2004071408. Exemplary anti-IL17 A/F antibodies and methods of producing such antibodies have been described previously, for example, in WO 2009136286 and U.S. Pat. No. 8,715,669. Exemplary anti-CMV antibodies, including anti-CMV-MSL, and methods of producing such antibodies have been described previously, for example, in WO 2012047732.

Exemplary polypeptides include include mammalian proteins, such as, e.g., CD4, integrins and their subunits, such as beta7, growth hormone, including human growth hormone and bovine growth hormone; growth hormone releasing factor; parathyroid hormone; thyroid stimulating hormone; lipoproteins; ct-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or tissue-type plasminogen activator (t-PA, e.g., Activase®, TNKase®, Retevase®); bombazine; thrombin; tumor necrosis factor-α and -β; enkephalinase; RANTES (regulated on activation normally T-cell expressed and secreted); human macrophage inflammatory protein (MIP-I-a); serum albumin such as human serum albumin; mullerian-inhibiting substance; mouse gonadotropin-associated peptide; DNase; inhibin; activin; vascular endothelial growth factor (VEGF); IgE, receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-α and TGF-β including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; other CD proteins such as CD3, CD8, CD19 and CD20; erythropoietin (EPO); thrombopoietin (TPO); osteoinductive factors; immunotoxins; a bone morphogenetic protein (BMP); an interferon such as interferon-α, -β, or -γ; colony stimulating factors (CSFs), e.g., M-CSF, GM-CSF, and G-CSF; interleukins (ILs), e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33 and so on; superoxide dismutase; T-cell receptors; surface membrane proteins; decay accelerating factor (DAF); a viral antigen such as, for example, a portion of an HIV envelope; transport proteins; homing receptors; addressins; regulatory proteins; integrins such as CD11a, CD11b, CD11c, CD18, integrin subunits such alpha4, alphaE, beta7; cellular adhesion molecules such as an ICAM, VLA-4 and VCAM; a tumor associated antigen such as HER1, (EGFR), HER2, HER3 or HER4 receptor; Apo2L/TRAIL, and fragments of any of the above listed polypeptides; as well as immunoadhesins and antibodies binding to; and biologically active fragments or variants of any of the above-listed proteins.

Additional exemplary polypeptides include brain polypeptides, including but not limited to, beta-secretase 1 (BACE1), Abeta, epidermal growth factor receptor (EGFR), human epidermal growth factor receptor 2 (HER2), tau, apolipoprotein E (ApoE), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), P-selectin, and caspase 6, and fragments of any of the above listed polypeptides; as well as immunoadhesins and antibodies binding to; and biologically active fragments or variants of any of the above-listed proteins.

Further exemplary polypeptides include therapeutic antibodies and immunoadhesins, including, without limitation, antibodies, including antibody fragments, to one or more of the following antigens: HER1 (EGFR), HER2 (e.g., trastuzumab, pertuzumab), HER3, HER4, VEGF (e.g., bevacizumab, ranibizumab), MET (e.g., onartuzumab), CD20 (e.g., rituximab, obinutuzumab, ocrelizumab), CD22, CD11a, CD11b, CD11c, CD18, an ICAM, VLA-4, VCAM, IL-17A and/or F, IgE (e.g., omalizumab), DR5, CD40, Apo2L/TRAIL, EGFL7 (e.g., parsatuzumab), NRP1, integrin beta7 (e.g., etrolizumab), IL-13 (e.g., lebrikizumab), Abeta (e.g., crenezumab, gantenerumab), P-selectin (e.g., inclacumab), IL-6R (e.g., tociluzumab), IFNα (e.g., rontalizumab), M1prime (e.g., quilizumab), mitogen activated protein kinase (MAPK), OX40L, TSLP, Factor D (e.g., lampalizumab) and receptors such as: IL-9 receptor, IL-5 receptor, IL-4receptor alpha, IL-13receptoralpha1 and IL-13receptoralpha2, OX40, TSLP-R, IL-7Ralpha (a co-receptor for TSLP), IL17RB (receptor for IL-25), ST2 (receptor for IL-33), CCR3, CCR4, CRTH2, FcepsilonRI and FcepsilonRII/CD23 (receptors for IgE). Other exemplary antibodies include those selected from, and without limitation, antiestrogen receptor antibody, anti-progesterone receptor antibody, anti-p53 antibody, anticathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

Certain Purification Methods

The protein to be purified using the methods described herein is generally produced using recombinant techniques. Methods for producing recombinant proteins are described, e.g., in U.S. Pat. Nos. 5,534,615 and 4,816,567, specifically incorporated herein by reference. In certain embodiments, the protein of interest is produced in a CHO cell (see, e.g. WO 94/11026). Examples of proteins, including anti-IL13 monoclonal antibodies (anti-IL13 MAb), which can be purified using the processes described herein have been described above.

When using recombinant techniques, the protein can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, the recombinant host cells may be separated from the cell culture medium by tangential flow filtration, for example.

Protein A immobilized on a solid phase is used to purify the anti-IL13 MAb preparation. In certain embodiments, the solid phase is a column comprising a glass, silica, agarose or polystyrene surface for immobilizing the Protein A. In certain embodiments, the solid phase is a controlled pore glass column or a silicic acid column. Sometimes, the column has been coated with a reagent, such as glycerol, in an attempt to prevent nonspecific adherence to the column. The PROSEP A™ column, commercially available from Bioprocessing Limited, is an example of a Protein A controlled pore glass column which is coated with glycerol. Other examples of columns contemplated herein include the POROS® 50 ATM (polystyrene) column or rProtein A SEPHAROSE FAST FLOW™ (agarose) column or MABSELECT SURE™ (agarose) column available from GE Healthcare Life Sciences (agarose).

The solid phase for the Protein A chromatography is equilibrated with a suitable buffer. For example, the equilibration buffer may be 25 mM Tris, 25 mM NaCl, pH 7.70±0.20.

The preparation derived from the recombinant host cells and containing impurities and/or contaminants is loaded on the equilibrated solid phase using a loading buffer which may be the same as the equilibration buffer. As the preparation containing impurities/contaminants flows through the solid phase, the protein is adsorbed to the immobilized Protein A and other impurities/contaminants (such as Chinese Hamster Ovary Proteins, CHOP, where the protein is produced in a CHO cell) may bind nonspecifically to the solid phase.

The next step performed sequentially entails removing the impurities/contaminants bound to the solid phase, antibody and/or Protein A, by washing the solid phase in an intermediate wash step. After loading, the solid phase may be equilibrated with equilibration buffer before beginning the intermediate wash step.

The intermediate wash buffer may comprise salt and optionally a further compound, such as (a) detergent (for example, polysorbate, e.g. polysorbate 20 or polysorbate 80); (b) solvent (such as hexylene glycol); and (c) polymer (such as polyethylene glycol {PEG]).

The salt employed may be selected based on the protein of interest. Exemplary salts include, but are not limited to, sodium acetate, sodium citrate, and potassium phosphate.

The amounts of the salt and further compound (if any) in the composition are such that the combined amount elutes the impurity(ies)/contaminant(s), without substantially removing the protein of interest. Exemplary salt concentrations in such wash buffers are from about 0.1 to about 2M, or from about 0.2M to about 0.6M. Useful detergent concentrations are from about 0.01 to about 5%, or from about 0.1 to 1%, or about 0.5%, e.g. where the detergent is polysorbate. Exemplary solvent concentrations are from about 1% to 40%, or from about 5 to about 25%. Where the further compound is a polymer (e.g. PEG 400 or PEG 8000), the concentration thereof may, for example, be from about 1% to about 20%, or from about 5% to about 15%.

The pH of the intermediate wash buffer is typically from about 4 to about 8, or from about 4.5 to about 5.5, or about 5.0. In one embodiment, the pH is 7.00±0.10.

Following the intermediate wash step described above, the protein of interest is recovered from the column. This is typically achieved using a suitable elution buffer. The protein may, for example, be eluted from the column using an elution buffer having a low pH (also referred to as acidic conditions), e.g. in the range from about 2 to about 5, or in the range from about 2.5 to about 3.5. Examples of elution buffers for this purpose include citrate or acetate buffers.

The eluted protein preparation may be subjected to additional purification steps either prior to, or after, the Protein A chromatography step. Exemplary further purification steps include hydroxyapatite chromatography; dialysis; affinity chromatography using an antibody to capture the protein; hydrophobic interaction chromatography (HIC); ammonium sulphate precipitation; anion or cation exchange chromatography; ethanol precipitation; reverse phase HPLC; chromatography on silica; chromatofocusing; ultrafiltration-diafiltration (UFDF), and gel filtration. In the examples herein, the Protein A chromatography step is followed by downstream anion exchange (e.g., Q-Sepharose-Fast Flow) or multimodal (e.g. mixed-mode) ion exchange (e.g., CAPTO™ Adhere) and HIC (e.g., PHENYL SEPHAROSE™ 6 fast flow-high sub) purification steps.

The protein thus recovered may be formulated in a pharmaceutically acceptable carrier and is used for various diagnostic, therapeutic or other uses known for such molecules.

In some embodiments of any of the methods described herein, the chromatography material is an ion exchange chromatography material; for example, an anion exchange chromatography material. In some embodiments, the anion exchange chromatography material is a solid phase that is positively charged and has free anions for exchange with anions in an aqueous solution passed over or through the solid phase. In some embodiments of any of the methods described herein, the anion exchange material may be a membrane, a monolith, or resin. In an embodiment, the anion exchange material may be a resin. In some embodiments, the anion exchange material may comprise a primary amine, a secondary amine, a tertiary amine or a quarternary ammonium ion functional group, a polyamine functional group, or a diethylaminoethyl functional group. In some embodiments of the above, the anion exchange chromatography material is an anion exchange chromatography column. In some embodiments of the above, the anion exchange chromatography material is an anion exchange chromatography membrane.

In some embodiments of any of the methods described herein, the ion exchange material may utilize a conventional chromatography material or a convective chromatography material. The conventional chromatography materials include, for example, perfusive materials (e.g., poly(styrene-divinylbenzene) resin) and diffusive materials (e.g., cross-linked agarose resin). In some embodiments, the poly(styrene-divinylbenzene) resin can be POROS® resin. In some embodiments, the cross-linked agarose resin may be sulphopropyl-Sepharose Fast Flow ("SPSFF") resin. The convective chromatography material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

Examples of anion exchange materials include, but are not limited to, POROS® HQ 50, POROS® PI 50, POROS® D, Mustang Q, Q SEPHAROSE™ FF, and DEAE Sepharose.

In some aspects, the chromatography material is a hydrophobic interaction chromatography material. Hydrophobic interaction chromatography (HIC) is a liquid chromatography technique that separates biomolecules according to hydrophobicity. Examples of HIC chromatography materials include, but are not limited to, Toyopearl hexyl 650, Toyopearl butyl 650, Toyopearl phenyl 650, Toyopearl ether 650, Source, Resource, Sepharose Hi-Trap, Octyl sepharose, PHENYL SEPHAROSE™ high performance, PHENYL SEPHAROSE™ 6 fast flow (low sub) and PHENYL SEPHAROSE™ 6 fast flow (high sub). In some embodiments of the above, the HIC chromatography material is a HIC chromatography column. In some embodiments of the above, the HIC chromatography material is a HIC chromatography membrane.

In some aspects, the chromatography material is an affinity chromatography material. Examples of affinity chromatography materials include, but are not limited to chromatography materials derivatized with protein A or protein G. Examples of affinity chromatography material include, but are not limited to, Prosep-VA, Prosep-VA Ultra Plus, Protein A sepharose fast flow, Tyopearl Protein A, MAbSelect, MABSELECT SURE™ and MABSELECT SURE™ LX. In some embodiments of the above, the affinity chromatography material is an affinity chromatography column. In some embodiments of the above, the affinity chromatography material is an affinity chromatography membrane.

Various buffers which can be employed depending, for example, on the desired pH of the buffer, the desired conductivity of the buffer, the characteristics of the protein of interest, and the purification method. In some embodiments of any of the methods described herein, the methods comprise using a buffer. The buffer can be a loading buffer, an equilibration buffer, or a wash buffer. In some embodiments, one or more of the loading buffer, the equilibration buffer, and/or the wash buffer are the same. In some embodiments, the loading buffer, the equilibration buffer, and/or the wash buffer are different. In some embodiments of any of the methods described herein, the buffer comprises a salt. The loading buffer may comprise sodium chloride, sodium acetate, or a mixture thereof. In some embodiments, the loading buffer is a sodium chloride buffer. In some embodiments, the loading buffer is a sodium acetate buffer.

Load, as used herein, is the composition loaded onto a chromatography material. Loading buffer is the buffer used to load the composition comprising the product of interest onto a chromatography material. The chromatography material may be equilibrated with an equilibration buffer prior to loading the composition which is to be purified. In some examples, the wash buffer is used after loading the composition onto a chromatography material and before elution of the polypeptide of interest from the solid phase. However, some of the product of interest, e.g. a polypeptide, may be removed from the chromatography material by the wash buffer (e.g. flow-through mode).

Elution, as used herein, is the removal of the product, e.g. polypeptide, from the chromatography material. Elution buffer is the buffer used to elute the polypeptide or other product of interest from a chromatography material. In many cases, an elution buffer has a different physical characteristic than the load buffer. For example, the elution buffer may have a different conductivity than load buffer or a different pH than the load buffer. In some embodiments, the elution buffer has a lower conductivity than the load buffer. In some embodiments, the elution buffer has a higher conductivity than the load buffer. In some embodiments, the elution buffer has a lower pH than the load buffer. In some embodiments, the elution buffer has a higher pH than the load buffer. In some embodiments the elution buffer has a different conductivity and a different pH than the load buffer. The elution buffer can have any combination of higher or lower conductivity and higher or lower pH.

Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

In some embodiments of any of the methods described herein, the flow rate is less than about any of 50 CV/hr, 40 CV/hr, or 30 CV/hr. The flow rate may be between about any of 5 CV/hr and 50 CV/hr, 10 CV/hr and 40 CV/hr, or 18 CV/hr and 36 CV/hr. In some embodiments, the flow rate is about any of 9 CV/hr, 18 CV/hr, 25 CV/hr, 30 CV/hr, 36 CV/hr, or 40 CV/hr. In some embodiments of any of the methods described herein, the flow rate is less than about any of 100 cm/hr, 75 cm/hr, or 50 cm/hr. The flow rate may be between about any of 25 cm/hr and 150 cm/hr, 25 cm/hr and 100 cm/hr, 50 cm/hr and 100 cm/hr, or 65 cm/hr and 85 cm/hr, or 50 cm/hr and 250 cm/hr, or 100 cm/hr and 250 cm/hr, or 150 cm/hr and 250 cm/hr.

Bed height is the height of chromatography material used. In some embodiments of any of the method described herein, the bed height is greater than about any of 3 cm, 10 cm, or 15 cm. The bed height may be between about any of 3 cm and 35 cm, 5 cm and 15 cm, 3 cm and 10 cm, or 5 cm and 8 cm. In some embodiments, the bed height is about any of 3 cm, 5 cm, 10 cm, or 15 cm. In some embodiments, bed height is determined based on the amount of polypeptide or contaminants in the load.

In some embodiments, the chromatography is in a column of vessel with a volume of greater than about 1 mL, 2 mL, 3 mL, 4 mL, 5 mL, 6 mL, 7 mL, 8 mL, 9 mL, 10 mL, 15 mL, 20 mL, 25 mL, 30 mL, 40 mL, 50 mL, 75 mL, 100 mL, 200 mL, 300 mL, 400 mL, 500 mL, 600 mL, 700 mL, 800 mL, 900 mL, 1 L, 2 L, 3 L, 4 L, 5 L, 6 L, 7 L, 8 L, 9 L, 10 L, 25 L, 50 L, 100 L, 200 L, 400 L, or 450 L.

In some embodiments, fractions are collected from the chromatography. In some embodiments, fractions collected are greater than about 0.01 CV, 0.02 CV, 0.03 CV, 0.04 CV, 0.05 CV, 0.06 CV, 0.07 CV, 0.08 CV, 0.09 CV, 0.1 CV, 0.2 CV, 0.3 CV, 0.4 CV, 0.5 CV, 0.6 CV, 0.7 CV, 0.8 CV, 0.9 CV, 1.0 CV, 2.0 CV, 3.0 CV, 4.0 CV, 5.0, CV. In some embodiments, fractions containing the product, e.g. polypeptide, are pooled. In some embodiments, fractions containing the polypeptide from the load fractions and from the elution fractions are pooled. The amount of polypeptide in a fraction can be determined by one skilled in the art; for example, the amount of polypeptide in a fraction can be determined by UV spectroscopy. In some embodiments, fractions containing detectable polypeptide fragment are pooled.

In some embodiments of any of the methods described herein, the at least one impurity or contaminant is any one or more of host cell materials, such as CHOP; leached Protein A; nucleic acid; a variant, fragment, aggregate or derivative of the desired polypeptide; another polypeptide; endotoxin; viral contaminant; cell culture media component, gentamicin, etc. In some examples, the impurity or contaminant may be a host cell protein (HCP) from, for example but not limited to, a bacterial cell such as an *E. coli* cell, an insect cell, a prokaryotic cell, a eukaryotic cell, a yeast cell, a mammalian cell, an avian cell, a fungal cell.

Host cell proteins (HCP) are proteins from the cells in which the polypeptide was produced. For example, CHOP are proteins from host cells, i.e., Chinese Hamster Ovary Proteins. The amount of CHOP may be measured by enzyme-linked immunosorbent assay ("ELISA") or mass spectrometry. In some embodiments of any of the methods described herein, the amount of HCP (e.g. CHOP) is reduced by greater than about any of 10%, 20%, 30%, 40%, 50%, 60%, 70%, 80%, 90%, or 95%. The amount of HCP may be reduced by between about any of 10% and 99%, 30% and 95%, 30% and 99%, 50% and 95%, 50% and 99%, 75% and 99%, or 85% and 99%. In some embodiments, the amount of HCP is reduced by about any of 10%, 20%, 30%, 40%, 50%, 60%, 70%, 80%, 85%, 90%, 95%, or 98%. In some embodiments, the reduction is determined by comparing the amount of HCP in the composition recovered from a purification step(s) to the amount of HCP in the composition before the purification step(s).

In some embodiments of any of the methods described herein, the methods further comprise recovering the purified polypeptide. In some embodiments, the purified polypeptide is recovered from any of the purification steps described herein. The chromatography step may be anion exchange chromatography, HIC, or Protein A chromatography. In some embodiments, the first chromatography step is protein A, followed by anion exchange or multimodal ion exchange, followed by HIC.

In some embodiments, the polypeptide is further purified following chromatography by viral filtration. Viral filtration is the removal of viral contaminants in a polypeptide purification feedstream. Examples of viral filtration include ultrafiltration and microfiltration. In some embodiments the polypeptide is purified using a parvovirus filter.

In some embodiments, the polypeptide is concentrated after chromatography. Examples of concentration methods are known in the art and include but are not limited to ultrafiltration and diafiltration.

In some embodiments of any of the methods described herein, the methods further comprise combining the purified polypeptide of the methods of purification with a pharmaceutically acceptable carrier.

Monoclonal Antibodies

In some embodiments, the antibodies purified according to the methods of the invention are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature* 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., *Monoclonal Antibody Production Techniques and Applications* pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal.* Biochem. 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature* 348:552-554 (1990). Clackson et al., *Nature* 352: 624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., *Proc. Natl Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.

Humanized Antibodies

In some embodiments, the antibody is a humanized antibody. Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.* 151:2296 (1993); Chothia et al., *J. Mol. Biol.* 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

In some embodiments, the antibody is a human antibody. As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region (JO gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669; 5,589,369; and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat polypeptide gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229, 275).

Antibody Fragments

In some embodiments, the antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')2 fragments (Carter et al., *Bio/Technology* 10:163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a F(ab')2 fragment, a scFv, a Fv, and a diabody.

Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

Other

Another type of covalent modification of the polypeptide comprises linking the polypeptide to one of a variety of nonproteinaceous polymers, e.g., polyethylene glycol, polypropylene glycol, polyoxyalkylenes, or copolymers of polyethylene glycol and polypropylene glycol. The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 18th edition, Gennaro, A. R., Ed., (1990).

Obtaining Polypeptides

The polypeptides used in the methods of purification described herein may be obtained using methods well-known in the art, including the recombination methods. The following sections provide guidance regarding these methods.

Polynucleotides

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and F(ab')$_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

Suitably, the polynucleotides described herein may be isolated and/or purified. In some embodiments, the polynucleotides are isolated polynucleotides.

The term "isolated polynucleotide" is intended to indicate that the molecule is removed or separated from its normal or natural environment or has been produced in such a way that it is not present in its normal or natural environment. In some embodiments, the polynucleotides are purified polynucleotides. The term purified is intended to indicate that at least some contaminating molecules or substances have been removed.

Suitably, the polynucleotides are substantially purified, such that the relevant polynucleotides constitutes the dominant (i.e., most abundant) polynucleotides present in a composition.

Expression of Polynucleotides

The description below relates primarily to production of polypeptides by culturing cells transformed or transfected with a vector containing polypeptide-encoding polynucleotides. It is, of course, contemplated that alternative methods, which are well known in the art, may be employed to prepare polypeptides. For instance, the appropriate amino acid sequence, or portions thereof, may be produced by direct peptide synthesis using solid-phase techniques (see, e.g., Stewart et al., *Solid-Phase Peptide Synthesis* W.H. Freeman Co., San Francisco, Calif. (1969); Merrifield, *J. Am. Chem. Soc.* 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the polypeptide may be chemically synthesized separately and combined using chemical or enzymatic methods to produce the desired polypeptide.

Polynucleotides as described herein are inserted into an expression vector(s) for production of the polypeptides. The term "control sequences" refers to DNA sequences necessary for the expression of an operably linked coding sequence in a particular host organism. The control sequences include, but are not limited to, promoters (e.g., naturally-associated or heterologous promoters), signal sequences, enhancer elements, and transcription termination sequences.

A polynucleotide is "operably linked" when it is placed into a functional relationship with another polynucleotide sequence. For example, nucleic acids for a presequence or secretory leader is operably linked to nucleic acids for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

For antibodies, the light and heavy chains can be cloned in the same or different expression vectors. The nucleic acid segments encoding immunoglobulin chains are operably linked to control sequences in the expression vector(s) that ensure the expression of immunoglobulin polypeptides.

The vectors containing the polynucleotide sequences (e.g., the variable heavy and/or variable light chain encoding sequences and optional expression control sequences) can be transferred into a host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *Escherichia coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

Vectors may be transformed into a suitable host cell as described below to provide for expression of a polypeptide. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

The vectors may be for example, plasmid, virus or phage vectors provided with an origin of replication, optionally a promoter for the expression of the said polynucleotide and optionally a regulator of the promoter. Vectors may contain one or more selectable marker genes which are well known in the art.

These expression vectors are typically replicable in the host organisms either as episomes or as an integral part of the host chromosomal DNA.

Host Cells

The host cell may be a bacterium, a yeast or other fungal cell, insect cell, a plant cell, or a mammalian cell, for example.

A transgenic multicellular host organism which has been genetically manipulated may be used to produce a polypeptide. The organism may be, for example, a transgenic mammalian organism (e.g., a transgenic goat or mouse line).

Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P), *Pseudomonas* such as *P. aeruginosa*, and *Streptomyces*. These examples are illustrative rather than limiting. Strain W3110 is one particularly preferred host or parent host because it is a common host strain for recombinant polynucleotide product fermentations. Preferably, the host cell secretes minimal amounts of proteolytic enzymes. For example, strain W3110 may be modified to effect a genetic mutation in the genes encoding polypeptides endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan'; *E. coli* W3110 strain 37D6, which has the complete genotype tonA ptr3 phoA E15 (argF-lac)169 degP ompT rbs7 ilvG kan'; *E. coli* W3110 strain 40B4, which is strain 37D6 with a non-kanamycin resistant degP deletion mutation; and an *E. coli* strain having mutant periplasmic protease. Alternatively, in vitro methods of cloning, e.g., PCR or other nucleic acid polymerase reactions, are suitable.

In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Eukaryotic microbes may be used for expression. Eukaryotic microbes such as filamentous fungi or yeast are suitable cloning or expression hosts for polypeptide-encoding vectors. *Saccharomyces cerevisiae* is a commonly used lower eukaryotic host microorganism. Others include *Schizosaccharomyces pombe; Kluyveromyces* hosts such as, e.g., *K. lactis* (MW98-8C, CBS683, CBS4574), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris; Candida; Trichoderma reesia; Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans*, and *A. niger.* Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula. Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides as described herein and in some instances are preferred (See Winnacker, *From Genes to Clones* VCH Publishers, N.Y., N.Y. (1987). For some embodiments, eukaryotic cells may be preferred, because a number of suitable host cell lines capable of secreting heterologous polypeptides (e.g., intact immunoglobulins) have been developed in the art, and include CHO cell lines, various Cos cell lines, HeLa cells, preferably, myeloma cell lines, or transformed B-cells or hybridomas. In some embodiments, the mammalian host cell is a CHO cell.

In some embodiments, the host cell is a vertebrate host cell. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR(CHO or CHO-DP-12 line); mouse sertoli cells; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Formulations and Methods of Making the Formulation

Provided herein are also formulations and methods of making the formulation comprising the polypeptides (e.g., antibodies) purified by the methods described herein. For example, the purified polypeptide may be combined with a pharmaceutically acceptable carrier.

The polypeptide formulations in some embodiments may be prepared for storage by mixing a polypeptide having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some embodiments, the polypeptide in the polypeptide formulation maintains functional activity.

The formulations to be used for in vivo administration must be sterile. This is readily accomplished by filtration through sterile filtration membranes.

The formulations herein may also contain more than one active compound as necessary for the particular indication being treated, preferably those with complementary activities that do not adversely affect each other. For example, in addition to a polypeptide, it may be desirable to include in the one formulation, an additional polypeptide (e.g., antibody). Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

Exemplary formulations of the anti-IL13 antibodies described herein are provided in International Patent Pub. No. WO 2013/066866.

Articles of Manufacture

The polypeptides purified by the methods described herein and/or formulations comprising the polypeptides purified by the methods described herein may be contained within an article of manufacture. The article of manufacture may comprise a container containing the polypeptide and/or the polypeptide formulation. In certain embodiments, the article of manufacture comprises: (a) a container comprising a composition comprising the polypeptide and/or the polypeptide formulation described herein within the container; and (b) a package insert with instructions for administering the formulation to a subject.

The article of manufacture comprises a container and a label or package insert on or associated with the container. Suitable containers include, for example, bottles, vials, syringes, etc. The containers may be formed from a variety of materials such as glass or plastic. The container holds or contains a formulation and may have a sterile access port (for example the container may be an intravenous solution bag or a vial having a stopper pierceable by a hypodermic injection needle). At least one active agent in the composition is the polypeptide. The label or package insert indicates that the composition's use in a subject with specific guidance regarding dosing amounts and intervals of polypeptide and any other drug being provided. The article of manufacture may further include other materials desirable from a commercial and user standpoint, including other buffers, diluents, filters, needles, and syringes. In some embodiments, the container is a syringe. In some embodiments, the syringe is further contained within an injection device. In some embodiments, the injection device is an autoinjector.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products.

Exemplary articles of manufacture containing formulations of the anti-IL13 antibodies described herein are provided in International Patent Pub. No. WO 2013/066866.

Further details of the invention are illustrated by the following non-limiting Examples. The disclosures of all references in the specification are expressly incorporated herein by reference.

EXAMPLES

As used in the Examples below and elsewhere herein, "PLB2" and "PLBL2" and "PLBD2" are used interchangeably and refer to the enzyme "phospholipase B-like 2" or its synonym, "phospholipase B-domain-like 2".

Example 1—General Methods

Materials and methods for all Examples were performed as indicated below unless otherwise noted in the Example.

MAb Feedstocks

MAb feedstocks for all examples were selected from industrial, pilot or small scale cell culture batches at Genentech (South San Francisco, Calif., U.S.A.). After a period of cell culture fermentation, the cells were separated and, in certain instances, the clarified fluid (harvested cell culture fluid, HCCF) was purified by Protein A chromatography and one or more additional chromatography steps and filtration steps as indicated in the Examples below.

MAb Quantification

The concentration of antibody was determined via absorbance at 280 and 320 nm using a UV-visible spectrophotometer (8453 model G1103A; Agilent Technologies; Santa Clara, Calif., U.S.A.) or NanoDrop 1000 model ND-1000 (Thermo Fisher Scientific; Waltham, Mass., U.S.A.). Species other than antibody (i.e. impurities) were too low in concentration to have an appreciable effect on UV absorbance. As needed, samples were diluted with an appropriate non-interfering diluent in the range of 0.1-1.0 absorbance unit. Sample preparation and UV measurements were performed in duplicate and the average value was recorded. The mAb absorption coefficients ranged from 1.42 to 1.645/ mg·ml·cm.

Total CHO Host Cell Protein (CHOP) Quantification

An ELISA was used to quantify the levels of the total host cell proteins called CHOP. The ELISAs used to detect CHO proteins in products were based upon a sandwich ELISA format. Affinity-purified polyclonal antibody to CHOP was coated onto a 96-well microtiter plate. Standards, controls, and samples were then loaded in duplicate into separate wells. CHOP, if present in the sample, will bind to the coat antibody (polyclonal anti-CHOP). After an incubation step, anti-CHOP polyclonal antibody-conjugated to horseradish peroxidase (HRP) was added to the plate. After a final wash step, CHOP was quantified by adding a solution of tetramethyl benzidine (TMB), also available as SUREBLUE RESERVE™ from KPL, Kirkegaard & Perry Laboratories, Inc., Gaithersburg, Md., cat no. 53-00-03), which when acted on by the HRP enzyme produces a colorimetric signal. The optical density (OD) at 450 nm was measured in each well. A five-parameter curve-fitting program (SOFTMAX® Pro, Molecular Devices, Sunnyvale, Calif.) was used to generate a standard curve, and sample CHOP concentrations were computed from the standard curve. The assay range for the total CHOP ELISA was from 5 to 320 ng/ml. CHOP concentration, in ng/mL, refers to the amount of CHOP in a sample using the CHOP standard as a calibrator. CHOP ratio (in ng/mg or ppm) refers to the calculated ratio of CHOP concentration to product concentration and, in certain instances, was the reported value for the test methods. The Total CHOP ELISA may be used to quantify total CHOP levels in a sample but does not quantify the concentration of individual proteins.

Murine Monoclonal Anti-Hamster PLBL2 ELISA Assay

The generation of mouse anti-hamster PLBL2 monoclonal antibodies and development of an ELISA assay for the detection and quantification of PLBL2 in recombinant polypeptide preparations using such antibodies is described in U.S. Provisional Patent Application Nos. 61/877,503 and 61/991,228. Briefly, the assay is carried out as follows.

Murine monoclonal antibody 19C10 was coated onto a half area 96-well microtiter plate at a concentration of 0.5 µg/mL in carbonate buffer (0.05M sodium carbonate, pH 9.6), overnight at 2-8° C. After coating, the plate was blocked with Blocking Buffer (0.15M NaCl, 0.1M sodium phosphate, 0.1% fish gelatin, 0.05% polysorbate 20, 0.05% Proclin® 300 [Sigma-Aldrich]; also referred to as Assay Diluent) to prevent non-specific sticking of proteins. Standards, controls, and samples were diluted in Assay Diluent (0.15M NaCl, 0.1M sodium phosphate, 0.1% fish gelatin, 0.05% polysorbate 20, 0.05% Proclin® 300 [Sigma-Aldrich]) then loaded in duplicate into separate wells and incubated for 2 hrs at room temperature (22-27° C.). PLBL2, if present in the sample, would bind to the coat (also referred to herein as capture) antibody. After the incubation step described above, unbound materials were washed away using Wash Buffer (0.05% polysorbate 20/PBS [Corning cellgro Cat. No. 99-717-CM]) and the 15G11 anti-PLBL2 murine monoclonal antibody conjugated to biotin was diluted in Assay Diluent to a concentration of 0.03125 µg/mL and added to the wells of the microtiter plate.

Biotin conjugation was carried out as follows. A biotinylation kit was purchased from Pierce Thermo Scientific, (P/N 20217, E-Z Link NHS-Biotin), and streptavidin-HRP (SA-HRP) from Jackson Immuno Cat. No. 016-030-084. Instructions in the Pierce Kit were followed. Briefly, IgG was dialyzed into PBS, pH 7.4, and biotin was added to the protein and mixed at room temperature for 1 hr. The labeled antibody was then dialized against PBS, pH 7.4 to remove excess biotin, filtered, and protein concentration determined by A280. After a 2 hr. incubation step with biotinylated 15G11 at room temperature, Streptavidin HRP (1:200,000 dilution in Assay Diluent) was added to the microtiter plate wells. After a final wash step with Wash Buffer (described above), color was developed (for PLBL2 quantification) by adding a solution of TMB (50 µl/well) (SUREBLUE RESERVE™ from KPL, Kirkegaard & Perry Laboratories, Inc., Gaithersburg, Md., cat no. 53-00-03) followed by incubation at room temperature for 10-20 minutes. Detection was carried out by assessing optical density (OD) at 450 nm in each well using a Molecular Devices SpectraMax M5e. A four-parameter curve-fitting program (SoftMax Pro v5.2 rev C) was used to generate a standard curve, and sample PLBL2 concentrations were computed from the linear range of the standard curve. Values in the linear range of the standard curve were used to calculate nominal PLBL2 (ng/mg or ppm). The linear range was approximately $EC_{10}$-$EC_{85}$ or 1.5-40 ng/mL as the range varied slightly from plate to plate. Values obtained for PLBL2 using this ELISA were comparable to estimates made by other methods (e.g., LC- MS/MS, polyclonal PLBL2 ELISA or total CHOP ELISA when diluted to the LOQ of the assay Rabbit Polyclonal Anti-Hamster PLBL2 ELISA Assay The generation of rabbit anti-hamster PLBL2 polyclonal antibodies and development of an ELISA assay for the detection and quantification of PLBL2 in recombinant polypeptide preparations using such antibodies is described in U.S. Provisional Patent Application Nos. 61/877,503 and 61/991,228. Briefly, the assay is carried out as follows.

Affinity purified rabbit polyclonal antibody was coated onto a half area 96-well microtiter plate at a concentration of 0.5 ug/mL in carbonate buffer (0.05M sodium carbonate, pH 9.6), overnight at 2-8° C. After coating, the plate was blocked with Blocking Buffer (0.15M NaCl, 0.1M sodium phosphate, 0.1% fish gelatin, 0.05% Polysorbate 20, 0.05% Proclin® 300 [Sigma-Aldrich]) to prevent non-specific sticking of proteins. Standards, controls, and samples were diluted in Assay Diluent (0.15M NaCl, 0.1M sodium phosphate, 0.1% fish gelatin, 0.05% Polysorbate 20, 0.05% Proclin® 300 [Sigma-Aldrich]) then loaded in duplicate into separate wells and incubated for 2 hr at room temperature (22-27° C.). PLBL2, if present in the sample, would bind to the coat (also referred to herein as capture) antibody. After the incubation step described above, unbound materials were washed away using Wash Buffer (0.05% Polysorbate 20/PBS [Corning Cellgro Cat. No. 99-717-CM]) and the affinity purified rabbit polyclonal antibody conjugated to horseradish peroxidase (HRP) was diluted in Assay Diluent to a concentration of 40 ng/mL and added to the wells of the microtiter plate.

HRP conjugation was carried out as follows. A HRP conjugation kit was purchased from Pierce Thermo Scientific, (P/N 31489, E-Z Link Plus Activated Peroxidase and Kit). Instructions in the Pierce Kit were followed. Briefly, IgG was dialyzed into Carbonate-Bicarbonate buffer, pH 9.4, and EZ-Link Plus Activated Peroxidase was added to the protein and mixed at room temperature for 1 hr. Sodium cyanoborohydride and Quenching buffer were added subsequently to stabilize the conjugation and quench the reaction. The labeled antibody was then dialyzed against PBS, pH 7.4, filtered, and protein concentration determined by A280.

After a 2 hr. incubation step with HRP conjugated rabbit polyclonal antibody at room temperature, a final wash step with Wash Buffer (described above) was performed. Afterwards, color was developed (for PLBL2 quantification) by adding a solution of TMB (50 ul/well) (SUREBLUE RESERVE™ from KPL, Kirkegaard & Perry Laboratories, Inc., Gaithersburg, Md., cat no. 53-00-03) followed by incubation at room temperature for 10-20 minutes. Detection was carried out by assessing optical density (OD) at 450 nm in each well using a Molecular Devices SpectraMax M5e. A five-parameter curve-fitting program (SoftMax Pro v5.2 rev C) was used to generate a standard curve, and sample PLBL2 concentrations were computed from the linear range of the standard curve. Values in the linear range of the standard curve were used to calculate nominal PLBL2 (ng/mg or ppm). The quantitative range of the assay was 0.5-50 ng/mL. Values obtained for PLBL2 using this ELISA were comparable to estimates made by other methods (e.g., murine monoclonal PLBL2 ELISA, LC-MS/MS or total CHOP ELISA when diluted to the LOQ of the assay).

LC-MS/MS Assay

For quantification of PLBL2 by LC-MS/MS, a Waters Acquity H-Class Bio UPLC and AB Sciex TripleTOF 5600+ mass spectrometer were used. Samples and calibration standards (recombinant PLBL2 spiked into a recombinant humanized monoclonal antibody preparation obtained from a mouse NS0 cell line [the NS0 cell line does not contain hamster PLBL2]) were reduced and digested by trypsin. A total of 40 µg digested sample was injected onto the UPLC, using a Waters BEH300 C18 column, particle size 1.7 µm. A linear gradient of acetonitrile was used to elute the peptides, at a flow rate of 300 µl/min and a column temperature of 60° C.

Peptides eluting from the UPLC were introduced to the mass spectrometer by electrospray ionization in positive ionization mode. Ion source temperature was set at 400° C., with an IonSpray voltage of 5500 v. and declustering potential of 76 v. A collision energy setting of 32 was used for the fragmentation of selected peptide ions. The mass spectrometer was operated in multiple reaction monitoring high resolution (MRM$^{HR}$) mode, using four specific PLBL2 peptides and their fragment ion transitions. The parent ions were selected by the quadrupole mass spectrometer with a mass to charge (m/z) selection window of 1.2 amu. Fragment ions of each parent ion were separated by the time-of-flight mass spectrometer and selected for quantification post data acquisition with a selection window of 0.025 amu.

The concentration of PLBL2 in samples was determined by measuring the specific signal responses of the four transitions, calibrated by those from the standards in the range of 2-500 ppm using a linear fit. Table 2 below shows the list of PLBL2 peptides monitored by LC-MS/MS.

TABLE 2

List of PLBL2 Peptides Monitored by LC-MS/MS.
TripleTOF 5600+ Scan Cycle

| Scan # | Scan Type | Peptide | Fragment Ion of Interest | Parent m/z | Fragment m/z |
|---|---|---|---|---|---|
| 1 | TOF MS | N/A | N/A | N/A | N/A |
| 2 | Product Ion | SVLLDAASGQLR (SEQ ID NO: 31) | +2y8 | 615.3461 | 817.4163 |
| 3 | Product Ion | GLEDSYEGR (SEQ ID NO: 32) | +2y7 | 513.2304 | 855.3479 |
| 4 | Product Ion | AFIPNGPSPGSR (SEQ ID NO: 33) | +2y9 | 600.3120 | 868.4272 |
| 5 | Product Ion | VTSFSLAK (SEQ ID NO: 34) | +2y6 | 426.7449 | 652.3665 |

Example 2—Improved Purification Process to Reduce Hamster PLBL2

A purification process for CHO-produced anti-IL13 MAb (lebrikizumab) was established to support early stage clinical trials and is referred to herein as the "Initial Process." The Initial Process employed the following chromatographic steps in order: Protein A affinity chromatography (MABSELECT SURE™) followed by cation exchange (POROS® HS) followed by anion exchange (Q SEPHAROSE™ Fast Flow). Additional virus inactivation and filtration steps were included and a final ultrafiltration-diafiltration (UFDF) step. The final product (drug substance) was formulated at a concentration of 125 mg/mL in 20 mM histidine acetate, 6% sucrose, 0.03% polysorbate 20, pH 5.7.

Using the Total CHOP ELISA Assay (described in Example 1 above), we observed that in-process intermediates and drug substance purified according to the Initial Process demonstrated atypical dilution-dependent behavior resulting in a >20% coefficient of variation across a normalized series of sample dilutions. This dilution-dependent behavior is exemplified by the data presented in Table 3 in which each successive two-fold dilution of anti-IL13 MAb product resulted in higher levels of CHOP (expressed in ppm) as determined using the Total CHOP ELISA. Using sensitive analytical methods, such as LC-MS/MS, we determined that a single CHOP species, or HCP, was the cause of this atypical dilution-dependent behavior. In particular, we established that the dilution-dependent behavior on the Total CHOP ELISA was due to antigen excess. Further investigation enabled us to identify the single HCP as an enzyme, hamster phospholipase B-like 2 (PLBL2). By diluting the product samples to the limit of assay quantitation (LOQ), we were able to estimate the level of PLBL2 in clinical lots of lebrikizumab purified using the Initial Process and determined that levels as high as 300 ppm (300 ng/mg) and above were present.

TABLE 3

Product dilution and CHOP levels.

| Fold Dilution | Total CHOP (ppm) |
| --- | --- |
| 2 | 0.58 |
| 4 | 1 |
| 8 | 2 |
| 16 | 4 |
| 32 | 7 |
| 64 | 14 |
| 128 | 26 |
| 256 | 49 |
| 512 | 97 |
| 1024 | 147 |
| 2048 | 228 |
| 4096 | 314 |
| 8192 | 346 |

This level of impurity (>300 ppm) of a single CHOP species such as we observed, is considered undesirable in MAb products intended for human clinical and/or therapeutic use, particularly late stage clinical trials and beyond. For example, such levels may be immunogenic when administered to human subjects as described in Example 3.

Accordingly, we investigated various modifications to the Initial Process as briefly outlined below. Based on the results of these investigations, we developed an improved purification process, described in detail below, and referred to herein as "Improved Process." Use of the Improved Process resulted in purified anti-IL13 MAb (lebrikizumab) product containing substantially reduced levels of PLBL2.

Efforts for modifying the purification process to reduce PLBL2 included methods orthogonal to the Initial Process including: precipitation, testing various additives to HCCF, additional column washes, hydrophobic interaction and mixed mode chromatography. These efforts were informed by use of one or more of the assays described in Example 1 to monitor the effectiveness of each of the modifications investigated for reduction in total CHOP and/or PLBL2 levels. The various modifications explored are described below.

Precipitation of CHOP in HCCF and Protein a Pool with Caprylic Acid

Caprylic acid precipitation has been described previously, including use in the monoclonal antibody industry (Wang et al., BioPharm International; Downstream Processing 2010, p4-10, October 2009; Brodsky et al., Biotechnology and Bioengineering, 109(10):2589, 2012) to selectively precipitate impurities from target proteins of interest. Caprylic acid, also known as octanoic acid, is a saturated fatty acid with eight carbons (formula $CH_3(CH_2)_6COOH$). Studies were done with anti-IL13 MAb to determine whether precipitation of the harvested cell culture fluid (HCCF) or Protein A pool with caprylic acid would lead to reduced CHOP and/or reduction of dilution-dependent behavior in the Total CHOP ELISA.

The anti-IL13 MAb starting material for these studies was HCCF and Protein A pools from a 1 kL harvest. 1% (v/v) caprylic acid was added to the HCCF and varying concentrations of caprylic acid (0%-3% v/v) were added to Protein A pools at pH 4.5 or pH 5.0. Samples were mixed for 5 hours at ambient temperature, 0.2 μm filtered, and diluted with Total CHOP ELISA diluent for detection and quantification using the Total CHOP ELISA. Titer of anti-IL13 MAb in HCCF before and after caprylic acid treatment was determined using an HPLC titer assay performed according to standard methods known in the art.

Treatment of HCCF with 1% v/v caprylic acid reduced CHOP by approximately 5-fold and resulted in a yield of anti-IL13 MAb of 91%. When Protein A pools were treated with various concentrations of caprylic acid, ranging from 0-3% v/v, we observed a loss in yield of >20% at pH 5.0 and no loss in yield at pH 4.5. When we assessed total CHOP in these caprylic acid-treated Protein A pools, we found a 2-fold to 3-fold reduction of CHOP (FIGS. 1A and B). However, as also shown in FIGS. 1A and B, dilution-dependence was still present under each of the conditions tested indicating that caprylic acid precipitation was not effective for addressing the dilution-dependent behavior observed in the Total CHOP ELISA and would thus not be effective for reducing PLBL2 levels in this product.

Additives to HCCF

Previous work by Sisodiya et al., Biotech J. 7:1233 (2012) has demonstrated that additives such as guanidine or sodium chloride to HCCF can reduce the CHOP in the subsequently purified Protein A pools. As arginine has also been shown to reduce CHOP when utilized as a wash on Protein A columns (Millipore Technical Bulletin, Lit. No. TB1024EN00, Rev. A, December, 2005; Millipore Technical Bulletin, Lit. No. 1026EN00, July, 2006, available at www(dot)Millipore(dot)com), we included it as an additive to HCCF. Various salts, chaotropes, and caprylic acid were added to the anti-IL13 MAb HCCF to assess the effectiveness of each for reducing the product and CHOP interaction during capture of product on MABSELECT SURE™ (MSS) protein A chromatography. The additives to HCCF tested were: 0.6M guanidine, 0.6M arginine, 0.6M NaCl, phosphate-buffered saline, and 1% caprylic acid.

Samples that had been treated with each of the HCCF additives were subjected to Protein A chromatography on MSS. Protein A pools were adjusted to pH 4.9 and further purified on the POROS® HS cation exchange chromatography step using the Initial Process conditions. Protein A pools and POROS® HS pools were diluted and submitted to the Total Chop ELISA. Adjusted Protein A pools were also tested on SEC-HPLC according to methods known in the art for the assessment of % aggregate, % variant species and the like.

Figure 2:
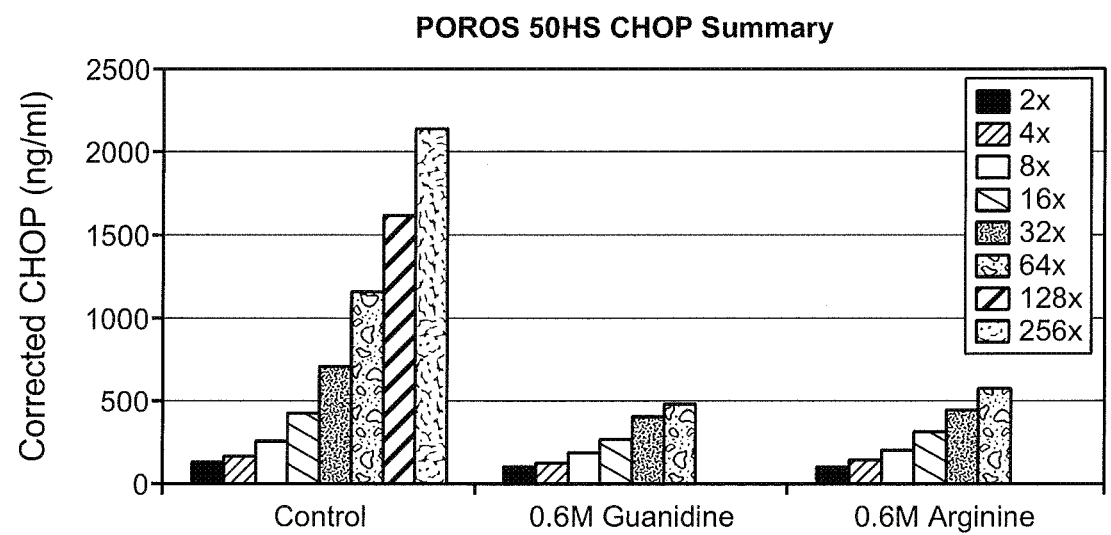
FIG. 2 shows total CHOP levels in additive-treated HCCF anti-IL13 MAb following Protein A chromatography which was followed by cation exchange chromatography on POROS® 50HS as described in Example 2. Corrected CHOP levels in ng/ml are shown on the vertical axis; the additive (control, 0.6M guanidine, or 0.6M arginine) is indicated on the horizontal axis, each bar represents the value from 2-fold serial dilution as indicated.

Yields on MABSELECT SURE™ were slightly lower for the runs where guanidine or arginine was added to HCCF. Of all the additives to HCCF tested, guanidine and arginine were the most effective for reducing CHOP levels substantially (see Table 4) and appeared to reduce dilution-dependence on the Protein A pools (data not shown). Further downstream processing of the Protein A pools on POROS® HS, however, showed CHOP ELISA dilution-dependence remaining in the corresponding POROS® pools as shown in FIG. 2. Accordingly, the data demonstrate that addition of guanidine or arginine to HCCF would not be effective for reducing PLBL2 levels in this product.

TABLE 4

HCCF Additives and effect on CHOP.

| Additive | Load pH | Yield (%) | Total CHOP (ppm) |
| --- | --- | --- | --- |
| Control (no additive) | 7.4 | 101 | 3417 |
| 0.6M guanidine | 7.6 | 90 | 892 |
| 0.6M arginine | 7.1 | 88 | 1237 |
| 0.6M NaCl | 7.7 | 99 | 2619 |
| PBS | 7.4 | 98 | 2773 |
| 1% caprylic acid | 6 | 93 | 3173 |

Washing of Protein A Column (MABSELECT SURE™)

It was observed that the more dilution-dependent CHOP eluted in early product-containing fractions on MABSELECT SURE™ (MSS) Protein A chromatography. This suggested that an additional wash step on MSS before elution might further reduce CHOP/PLBL2. Several washes on MSS were tested for their ability to reduce CHOP/PLBL2 in the Protein A pools. For this study, purified anti-IL13 MAb UFDF pool was used as the load material. The UFDF pool was diluted to 1.7 mg/mL (approximate HCCF titer) and loaded onto MSS at 29 g/L resin. Various washes were tested, for example; 0.5M arginine pH 8.5, 0.5M arginine pH 9.5 with and without 1% polysorbate 20, 0.5M TMAC pH 7.1, 25 mM MOPS pH 7.1, and compared with a high salt wash pH 7.0. Product was eluted under acidic conditions (pH 2.8) and pooled beginning at 0.5 OD (A280) and continuing for a total volume of 2.4 column volumes. Each adjusted pool was diluted and assayed using the Total CHOP ELISA. The summary of these results is that none of the washes adequately reduced CHOP/PLBL2 or dilution-dependence in the Total CHOP ELISA. It thus appeared unlikely we would find protein A wash conditions that would be effective for reducing PLBL2 levels in this anti-IL13 MAb product and we did not investigate these further.

Washing of Cation Exchange Column (POROS® HS)

Based on theoretical calculations using the amino acid sequences of anti-IL13 MAb and the PLBL2 impurity, we estimated that the pI of PLBL2 is approximately 6.0 and similar to anti-IL13 MAb (pI 6.1). We also estimated that there would be a significant difference in net charge between anti-IL13 MAb and PLBL2 at pH 4 and pH 10. As such, we tested various low pH washes on the Initial Process POROS® HS cation exchange step to assess whether these would be effective for selectively reducing total CHOP and/or PLBL2 and dilution-dependence behavior. The following washes were tested at pH 4: (i) acetate gradient, 300 mM-1,000 mM over 20 column volumes (CV); (ii) citrate gradient, 100 mM-500 mM over 20 CV; (iii) citrate wash step at 260 mM; and (iv) arginine gradient to 15 mS/cm (conductivity measurement) over 20 CV.

The results showed that anti-IL13 MAb and CHOP did not elute with the pH 4 acetate gradient up to the tested salt concentration of 1M. Increasing amounts of citrate or acetate resulted in product insolubility and precipitation. All of the pH 4 washes resulted in low yield on the POROS® HS step and none of the washes significantly reduced CHOP dilution-dependence. Accordingly, inclusion of a low pH wash of the cation exchange column was not effective for reducing PLBL2 levels in this product.

Hydroxyapatite Resin and CAPTO™ Adhere Resin

Ceramic hydroxyapatite (CHT) macroporous resin Type I, 40 um (BioRad) is comprised of calcium phosphate $(Ca_5(PO_4)_3OH)_2$ in repeating hexagonal structures. There are two distinct binding sites; C-sites with sets of 5 calcium ion doublets and P-sites containing pairs of —OH containing phosphate triplets. This resin has mixed mode properties and has been shown to separate challenging impurities such as aggregates (P. Gagnon, New Biotechnology 25(5):287 (2009)).

To identify initial conditions for running a CHT column, we performed high throughput robot screening of CHT resin Type I, 40 um testing a pH range of 6.5-8.0 and varying concentrations of sodium chloride and sodium phosphate for elution. Such high throughput robot screenings have been previously described, for example, in Wensel et al., Biotechnol. Bioeng. 100:839 (2008). Samples from these screenings were tested in the Total CHOP ELISA.

CAPTO™ Adhere (GE Healthcare) is a mixed mode resin that exhibits both ionic and hydrophobic properties. The base matrix is a rigid agarose, and the ligand is N-benzyl-N-methylethanolamine. The ability of this resin to reduce total CHOP and/or PLBL2 was assessed first with a high-throughput screening study and then with subsequent column conditions.

Initial studies to identify conditions for running a CAPTO™ Adhere column were done using a high-throughput robot screening method similar to that described above to test binding of anti-IL13 MAb to CAPTO™ Adhere at two load densities (5 g/L resin and 40 g/L resin). Salt and pH ranges were also tested; from 25 mM-200 mM sodium acetate and pH 4.0-6.5. The load material was the Initial Process UFDF pool that contained approximately 200 ppm of total CHOP at LOQ by the Total CHOP ELISA. Samples of the unbound (flow-through) on CAPTO™ Adhere were diluted and assayed using the Total CHOP ELISA.

The results were as follows. For CHT chromatography, none of the tested conditions substantially reduced total CHOP or PLBL2 or affected assay dilution-dependence behavior. In addition, yields were poor and no clearance of high molecular weight species was achieved. For CAPTO™ Adhere chromatography, yields were poor and the assayed material showed substantial dilution-dependence behavior in the Total CHOP ELISA. Accordingly, the use of CHT and CAPTO™ Adhere resins were not explored further as it was clear that we would be unlikely to find conditions using these resins that would be effective for reducing PLBL2 levels in this anti-IL13 MAb product.

Hydrophobic Interaction Chromatography Resins and Membranes

We initially tested HIC membrane adsorber referred to as Sartobind and manufactured by Sartorius. Sartobind is made with a base matrix of regenerated cellulose and covalently linked hydrophobic phenyl ligand groups.

The membrane tested was Sartobind HIC 3 mL device (8 mm bed height). We adjusted the pool from the Initial Process POROS® HS pool to 0.55M potassium phosphate pH 7.0 and used a flow rate of 10 mL/min. Product was eluted in 0.55M potassium phosphate pH 7.0 (collected in the unbound fractions in 3 mL fractions).

We observed that the anti-IL13 MAb became hazy and turbid upon conditioning to 0.55M potassium phosphate and required an additional 0.2 um filtration step. The results showed a reduction in total CHOP, however, the remaining CHOP still demonstrated dilution dependent behavior in the Total CHOP ELISA. Use of this membrane was not evaluated further as it seemed unlikely that effective conditions would be identified for reducing PLBL2 levels in this product.

Next, we employed a high throughput screen to evaluate several different HIC resins. OCTYL-SEPHAROSE® Fast Flow (FF), BUTYL-SEPHAROSE® 4 Fast Flow, PHENYL SEPHAROSE™ 6 Fast Flow (high sub) and PHENYL SEPHAROSE™ 6 Fast Flow (low sub) were obtained from GE Healthcare. These four resins were chosen because they represent a wide range of varying hydrophobicity (OCTYL-SEPHAROSE® Fast Flow is the least hydrophobic, followed by PHENYL SEPHAROSE™ 6 Fast Flow (low sub) and BUTYL-SEPHAROSE® 4 Fast Flow, with PHENYL SEPHAROSE™ 6 Fast Flow (high sub) the most hydrophobic. We tested several combinations of pH and salt concentrations for their effectiveness at reducing PLBL2 in anti-IL13 MAb preparations. The anti-IL13 MAb preparation employed for the HIC resin experiments was a UFDF pool from a run using the Initial Process. The anti-IL13 MAb concentration was 180 mg/mL and the load density was 40 mg antibody/mL resin. We tested pH 5.5 (25 mM sodium acetate), pH 6.0 (25 mM MES), pH 7.0 (25 mM MOPS), and pH 8.0 (25 mM Tris) and sodium sulfate concentrations between 0 mM and 400 mM. For each condition tested, flow-through samples were collected, diluted and tested using the Total CHOP ELISA assay.

Figure 3A:
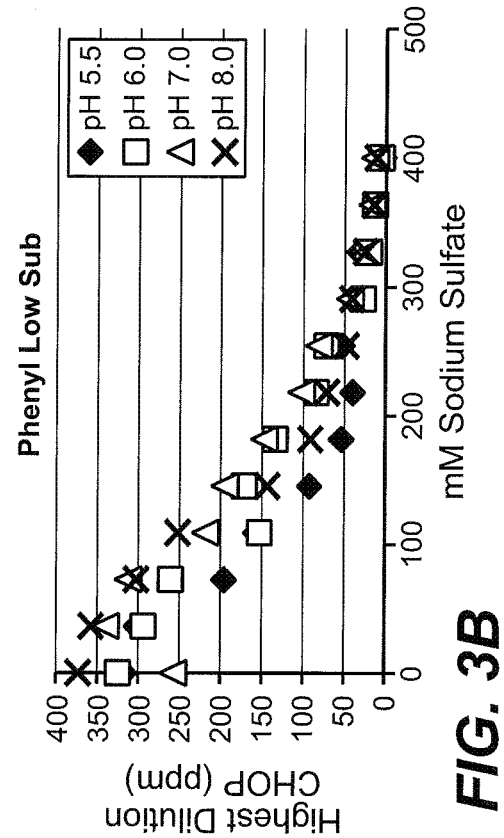
FIGS. 3A-3D show total CHOP levels in UFDF pools of anti-IL13 MAb subjected to different HIC resins under varying salt and pH conditions as described in Example 2.
Figure 3B:
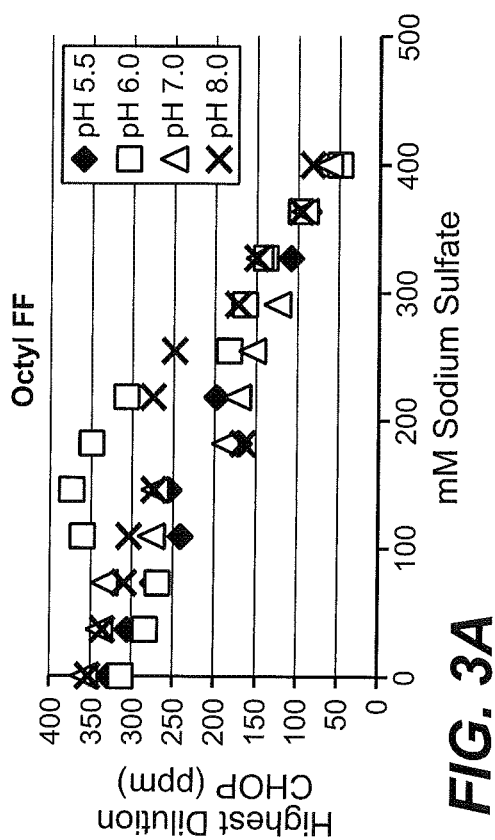
Figure 3C:
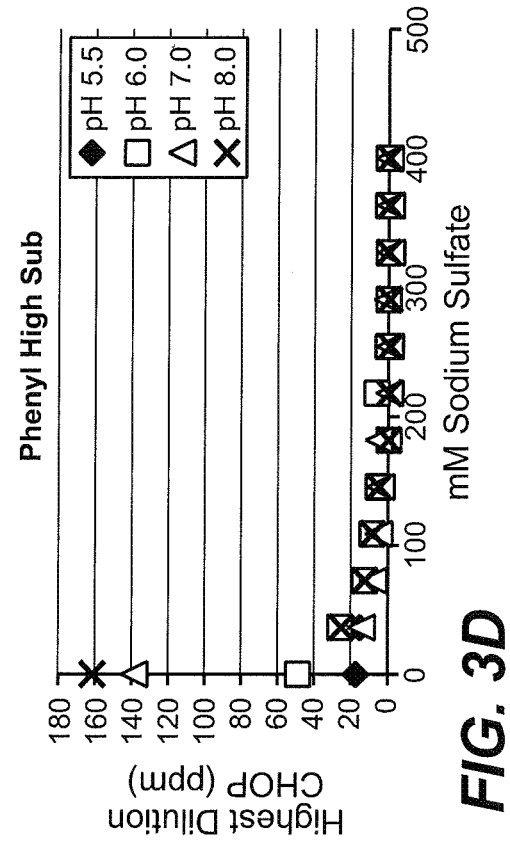
Figure 3D:
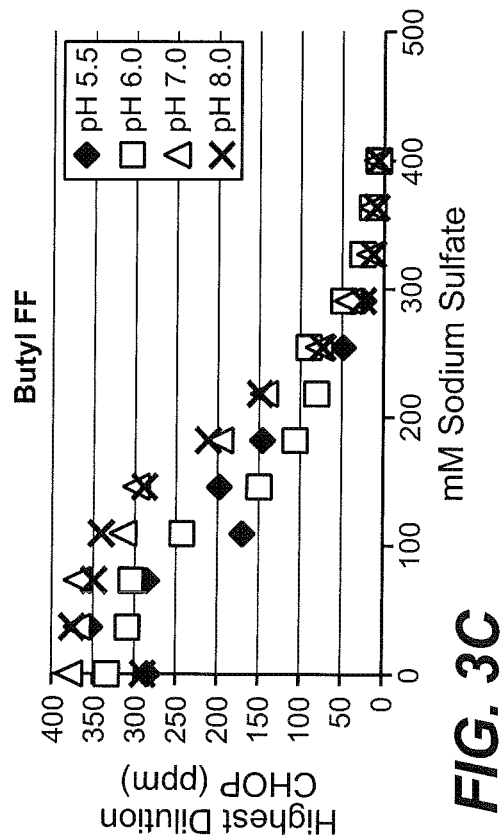

The results are shown in FIGS. 3A-D. With increasing salt, we observed less total CHOP in the flow-through for each resin. The OCTYL-SEPHAROSE® Fast Flow resin (FIG. 3A) showed the highest level of total CHOP while the PHENYL SEPHAROSE™ 6 Fast Flow (high sub) resin reduced total CHOP to very low levels, even with lower amounts of salt (FIG. 3D) and the PHENYL SEPHAROSE™ 6 Fast Flow (low sub) and BUTYL-SEPHAROSE® Fast Flow resins showed intermediate levels of total CHOP. Interestingly, there was also minimal effect of pH on CHOP removal using each of the resins except for PHENYL SEPHAROSE™ 6 Fast Flow (high sub) in low salt conditions (FIG. 3D). For this resin, at low salt conditions, higher pH resulted in higher CHOP in the flow-through fraction (FIG. 3D). Based on these results, PHENYL SEPHAROSE™ 6 Fast Flow (high sub) appeared promising and was chosen for further studies which included running the column in either bind-elute or flow-through mode.

Operation of HIC using the PHENYL SEPHAROSE™ 6 Fast Flow (high sub) resin in the bind-elute mode required conditioning of the anti-IL13 MAb load with salt to enable binding of the antibody to the resin. Increasing salt increased the dynamic binding capacity (mg of anti-IL13/mL resin) for loading product to the resin. But with increasing salt concentration in the product, we observed increased turbidity and formation of high molecular weight species (HMWs), in particular in combination with lower pH.

As mentioned above, PHENYL SEPHAROSE™ 6 Fast Flow (high sub) may also be operated in flow-through mode and such operation would require less salt conditioning of the load. From a product quality and product stability viewpoint, for example, product with less turbidity and less HMWs, less salt conditioning would be desirable. Accordingly, we proceeded with process optimization using PHENYL SEPHAROSE™ 6 Fast Flow (high sub) resin in flow-through mode.

To optimize the process, we investigated numerous parameters for running the HIC column including load concentration, load pH, load salt molarity, load density on the resin, bed height, flowrate, temperature, equilibration buffer pH and molarity. For these experiments, we monitored total CHOP using the Total CHOP ELISA and also PLBL2 by LC-MS/MS. Certain exemplary data is shown in Table 5. The data in Table 5 shows that the HIC column run under the indicated conditions in flow-through mode was effective for substantially reducing PLBL2 levels from the high levels detected in the Protein A pool. The PLBL2 levels after HIC were reduced by several hundred fold compared to the levels in the Protein A pool.

TABLE 5

Total CHOP and PLBL2 Levels under Varying HIC Column Conditions.

| Sample (bed height, flow rate) | % Yield | Total CHOP (ppm by ELISA at LOQ) | PLBL2 (ppm by LC-MS/MS) |
| --- | --- | --- | --- |
| Protein A pool (Load for HIC Column) |  | 3324 | 957 |
| 15 cm, 150 cm/hr | 88 | 43 | 4 |
| 25 cm, 150 cm/hr | 92 | 44 | 2 |
| 15 cm, 100 cm/hr | 90 | 67 | 5 |
| 25 cm, 100 cm/hr | 92 | 63 | 3 |
| 15 cm, 200 cm/hr | 93 | 62 | 6 |
| 25 cm, 200 cm/hr | 90 | 72 | 4 |
| 15 cm, 150 cm/hr | 54 | 76 | 2 |

Using the PLBL2 LC-MS/MS assay and other typical product quality assays (e.g., SE-HPLC, CE-SDS, iCIEF) to guide process parameter selections, we identified the following conditions as desirable for running of the HIC column as assessed by product quality attributes and reduction of PLBL2: equilibration and wash buffer: 50 mM sodium acetate, pH 5.0; target load density: 100 g/L, flow rate: 150 cm/hr, 22° C.±3° C. Certain small variations of these conditions may also be desirable, for example, 25° C.±3° C. or 27° C.±3° C. Optical density (OD) was monitored by absorbance at 280 nm (A280) and the pool (i.e. the flow-through) was collected between 0.5 OD to 1.5 OD or after 8 column volumes of wash.

As mentioned above, the Initial Process was: Protein A affinity chromatography (MABSELECT SURE™) followed by cation exchange (POROS® HS) followed by anion exchange (Q SEPHAROSE™ Fast Flow). After developing processes to reduce PLBL2 levels as described above, we next sought to implement process changes in a convenient manner. Accordingly, we explored adding the HIC column to the Initial Process thereby creating a four-column process as well as substituting the HIC column for either the CEX column or the AEX column and finally we explored the order of the columns. We found that a three column process, Protein A affinity chromatography (MABSELECT SURE™), followed by anion exchange (Q SEPHAROSE™ Fast Flow), followed by HIC operated in flow-through mode (PHENYL SEPHAROSE™ 6 Fast Flow (high sub)) provided the most convenient process and was the most effective for reducing PLBL2 in the final drug substance. This three-column process is described in detail below.

The first affinity chromatography step was a bind-and-elute process using MABSELECT SURE™ resin. After column equilibration (25 mM sodium chloride, 25 mM Tris pH 7.7), the HCCF was loaded on the column and washed with the equilibration buffer and a high salt pH 7.0 wash buffer. Anti-IL13 MAb was eluted from the column under acidic conditions (pH 2.8).

The second anion-exchange chromatography step was operated in a bind-and-elute mode using Q SEPHAROSE™ Fast Flow (QSFF) resin. After column equilibration (50 mM Tris, pH 8.0), the anti-IL13 pool from the MABSELECT SURE™ column was adjusted to pH 8.05 and loaded onto the column. The column was washed (50 mM Tris, pH 8.0) and anti-IL13 MAb eluted from the column with 85 mM sodium chloride, 50 mM Tris pH 8.0.

The third and final hydrophobic interaction chromatography step was operated in a flow-through mode using PHENYL SEPHAROSE™ 6 Fast Flow (High Sub) resin. After column equilibration (50 mM sodium acetate pH 5.0), the anti-IL13 pool from the QSFF column was adjusted to pH 5.0 and loaded on the column. The anti-IL13 MAb flowed through and the column was also washed with equilibration buffer (50 mM sodium acetate pH 5.0). The anti-IL13 MAb pool was initiated and terminated based on A280 with pooling occurring between 0.5 to 1.5 OD or a maximum of 8 column volumes.

(242, 328, and 273 ng/mg in three different runs) while the data in Table 7 clearly shows that the Improved Process was quite effective for producing purified product with substantially reduced levels of total CHOP (1.1, <0.9, 2.8, and 3.4 ng/mg in four different runs) and substantially reduced levels of PLBL2 (0.21, 0.42, 0.35, and 0.24 ng/mg in four different runs). Consistent with the data presented above, the data in Table 7 shows that the HIC column run under the conditions described above was particularly effective for reducing total CHOP and PLBL2 levels in anti-IL13 MAb preparations.

TABLE 6

Total CHOP and PLBL2 Levels at Various Stages of Purification of Anti-IL13 MAb Using the Initial Process.

| | In-process sample | | | | | |
|---|---|---|---|---|---|---|
| | Total CHOP (ng/mg at LOQ by ELISA) | | | PLBL2 (ng/mg by ELISA) | | |
| | Run No. | | | | | |
| | 1 | 2 | 3 | 1 | 2 | 3 |
| HCCF | 620920 | 541072 | 608789 | 1895 | 3669 | 2535 |
| ProA Pool | 2892 | 2855 | 3505 | 587 | 769 | 478 |
| CEX Pool | 136 | 310 | 138 | 345 | 439 | 287 |
| AEX Pool | 104 | 163 | 93 | 291 | 304 | 261 |
| UFDF Pool | 179 | 310 | 189 | 242 | 328 | 273 |

TABLE 7

Total CHOP and PLBL2 Levels at Various Stages of Purification of Anti-IL13 MAb Using the Improved Process.

| | In-process sample | | | | | | | |
|---|---|---|---|---|---|---|---|---|
| | Total CHOP (ng/mg at LOQ by ELISA) | | | | PLBL2 (ng/mg by ELISA) | | | |
| | Run No. | | | | | | | |
| | 1 | 2 | 3 | 4 | 1 | 2 | 3 | 4 |
| HCCF | 332132 | 399157 | 540134 | 644549 | 4084 | 3770 | 3077 | 2986 |
| ProA Pool | 2318 | 2768 | 3552 | 3797 | 1354 | 1995 | 1027 | 975 |
| AEX Pool | 495 | 653 | 414 | 377 | 723 | 933 | 677 | 616 |
| HIC Pool | <2.1 | <1.9 | 5.0 | 7.7 | <0.6 | <0.6 | <0.6 | <0.6 |
| UFDF Pool | 1.1 | <0.9 | 2.8 | 3.4 | 0.21 | 0.42 | 0.35 | 0.24 |

As with the Initial Process, additional virus inactivation and filtration steps were included and a final ultrafiltration-diafiltration (UFDF) step. The final product (drug substance) was formulated at a concentration of 125 mg/mL in 20 mM histidine acetate, 6% sucrose, 0.03% polysorbate 20, pH 5.7.

A comparison of the Initial Process to the Improved Process with respect to total CHOP and PLBL2, as measured by the Total CHOP ELISA and the monoclonal PLBL2 ELISA, respectively, is provided in Tables 6 (Initial Process) and 7 (Improved Process). The data in Table 6 clearly shows that the Initial Process resulted in purified product (UFDF pool) containing high levels of total CHOP (179, 310, and 189 ng/mg in three different runs) and high levels of PLBL2

In summary, faced with the problem of assay non-linear dilution behavior attributable to high levels of a single CHOP species in purified anti-IL13 MAb preparations, we first identified the CHOP species as hamster PLBL2, an impurity which has not been previously described in recombinant protein preparations produced from CHO cells. We next identified purification conditions to effectively reduce the levels of PLBL2 in the anti-IL13 MAb preparations. Finally, we integrated these purification conditions into the overall purification process resulting in an improvement to the prior anti-IL13 MAb purification process. This Improved Process employs a HIC column run in flow-through mode to reduce PLBL2 levels, which is run in combination with an affinity chromatography step and an anion exchange chromatography step. We showed that the Improved Process is robust and effective for substantially reducing hamster PLBL2 levels in anti-IL13 MAb preparations. We showed that the Improved Process reproducibly reduced PLBL2 levels by approximately 1000 fold compared to the Initial Process. Such reduction in PLBL2 levels was important for producing a purified anti-IL13 MAb product suitable for therapeutic use in patients in late stage clinical trials and beyond.

Purification Process to Reduce Hamster PLBL2 in Anti-Abeta Antibody Preparations We next sought to assess whether the purification methods described above, particularly use of a HIC column for a final chromatography step, would similarly be effective for reducing PLBL2 levels in other antibody preparations. For this experiment, we chose an anti-Abeta antibody, which was produced in CHO cells. Exemplary anti-Abeta antibodies and methods of producing such antibodies have been described previously, for example, in WO2008011348, WO2007068429, WO2001062801, and WO2004071408. These particular experiments used the anti-Abeta antibody known as crenezumab. As described for the anti-IL13 MAb, we explored various resins and buffers for the second column after the Protein A affinity column and we explored various buffers and run conditions for the HIC column to identify those that were optimal for anti-Abeta for product quality and stability attributes as well as for removal of hamster PLBL2.

We found that a three column process, Protein A affinity chromatography (MABSELECT SURE™), followed by use of a mixed mode resin (CAPTO™ Adhere), followed by HIC operated flow-through mode (PHENYL SEPHAROSE™ 6 Fast Flow (high sub)) was convenient and effective for reducing PLBL2 in the final drug substance. This three-column process is described in detail below.

The first affinity chromatography step was a bind-and-elute process using MABSELECT SURE™ resin similar to that described above for the anti-IL13 MAb.

The second mixed mode chromatography step was operated in a flow-through mode using CAPTO™ Adhere resin. After column equilibration (20 mM MES, 150 mM sodium acetate, pH 6.25), the anti-Abeta pool from the MABSELECT SURE™ column was adjusted to pH 6.25 and loaded onto the column. Pooling began at 0.5 OD during the load phase. After completing the load, the column was washed with 5 column volumes (CVs) of equilibration buffer (20 mM MES, 150 mM sodium acetate, pH 6.25) and the entire 5 CVs were also collected.

The third and final hydrophobic interaction chromatography step was operated in a flow-through mode using PHENYL SEPHAROSE™ 6 Fast Flow (High Sub) resin. After column equilibration (150 mM sodium acetate pH 5.0), the anti-Abeta pool from the CAPTO™ Adhere column was adjusted to pH 5.0 and loaded on the column. The anti-Abeta MAb flowed through and the column was also washed with equilibration buffer (150 mM sodium acetate pH 5.0). The anti-Abeta MAb pool was initiated during the load phase based on A280 with pooling beginning at 0.5 OD. The column was washed with 10 CVs of equilibration buffer (150 mM sodium acetate pH 5.0) and the entire 10 CVs were also collected. As with the anti-IL13 MAb, additional virus inactivation and filtration steps were included and a final ultrafiltration-diafiltration (UFDF) step.

The results of using the above process during four different purification runs are shown in Table 8 below.

TABLE 8

PLBL2 Levels at Various Stages of Purification of Anti-Abeta MAb Using HIC.

| In-process sample | PLBL2 (ng/mg by ELISA) Run No. | | | |
|---|---|---|---|---|
| | 1 | 2 | 3 | 4 |
| HCCF | 622 | 564 | 1264 | 553 |
| CpA Pool | 7 | 8 | 9 | 2.5 |
| HIC Pool (300 g/L Load density) | 0.7 | 0.6 | 0.3 | 0.3 |
| HIC Pool (100 g/L Load density) | <0.2 | <0.2 | <0.2 | Not tested |

The results shown in Table 8 demonstrate that use of a HIC resin as a final chromatography step effectively reduced residual PLBL2 levels in the anti-Abeta MAb preparation to an amount similar to that seen for the anti-IL13 MAb. While a load density of 300 g/L produced desirable results from the viewpoint of both product recovery and reduction in PLBL2, further reduction in residual PLBL2 was seen by reducing the load density for the HIC column from 300 g/L to 100 g/L.

We also investigated two other conditions for the HIC chromatography step, load pH and load sulfate molarity. For these experiments, we started with a CAPTO™ Adhere pool containing 51 ng/mg PLBL2 (as measured by ELISA), 15 mM sodium acetate pH 5.5. We adjusted the load pH and the load sulfate molarity to the values shown in Table 9 below using 0 mM sodium sulfate or 800 mM sodium sulfate stock solutions at varying pH. We tested each load pH indicated in Table 9 under low sulfate molarity conditions (0 mM) and high sulfate molarity conditions (240 mM). Each condition was tested at a load density of 60 g/L. As shown by the results presented in Table 9, decreasing the load pH to pH 4 or pH 5 or increasing the load sulfate molarity (to 240 mM sulfate) were each effective for reducing the levels of PLBL2 in the final HIC pool. The combination of pH 4.0 and 240 mM sulfate in the load was particularly effective for minimizing the amount of residual PLBL2 in the HIC pool.

TABLE 9

PLBL2 levels in the HIC pool observed over a range of load pH and sulfate molarity.

| Load pH | PLBL2 (ng/mg by ELISA) | |
|---|---|---|
| | Low Sulfate Molarity (0 mM) | High Sulfate Molarity (240 mM) |
| 4 | 4 | 1 |
| 5 | 10 | 3 |
| 6 | 27 | 5 |
| 7 | 64 | 6 |

Accordingly, use of a HIC resin as a final chromatography step in the purification of CHO-produced polypeptides, such as the anti-IL13 MAb and the anti-Abeta MAb described herein, effectively reduced the residual amount of hamster PLBL2 to very low levels, e.g., 1 ng/mg or less in the HIC pool.

Purification Process to Reduce Hamster PLBL2 in IgG1 Antibody Preparations

Next, we assessed whether the purification methods described for the anti-IL13 and anti-Abeta IgG4 antibody preparations, particularly use of a HIC column for a final chromatography step, would similarly be effective for reducing PLBL2 levels in IgG1 antibody preparations. For these experiments, we first chose an anti-IL17 A/F antibody, which is an IgG1 antibody and which was produced in CHO cells. Exemplary anti-IL17 A/F antibodies and methods of producing such antibodies have been described previously, for example, in WO 2009136286 and U.S. Pat. No. 8,715,669. As described for the anti-IL13 and anti-Abeta MAbs, we explored various resin (in particular, PHENYL SEPHAROSE™ FF [low sub] and PHENYL SEPHAROSE™ FF [high sub] and buffer conditions (in particular, 50 mM sodium acetate, pH 5.5 and 50 mM Tris, 85 mM sodium acetate, pH 8.0) for the HIC column to identify those that were optimal for anti-IL17 A/F for product quality and stability attributes as well as for removal of hamster PLBL2.

We found that a three column process, Protein A affinity chromatography (MABSELECT SURE™), followed by cation exchange chromatography (POROS® 50HS) operated in bind-and-elute mode, and HIC (PHENYL SEPHAROSE™ 6 Fast Flow (high sub)) operated in flow-through mode was convenient and effective for reducing PLBL2 in the final drug substance. This three-column process is described in detail below.

The first affinity chromatography step was a bind-and-elute process using MABSELECT SURE™ resin similar to that described above for the anti-IL13 and anti-Abeta MAbs. The second cation exchange chromatography step used POROS® 50HS resin and was operated in bind-and-elute mode. After column equilibration (40 mM sodium acetate, pH 5.5), the pH-adjusted anti-IL17 A/F MABSELECT SURE™ pool (pH 5.0) was loaded onto the column. The column was washed (40 mM sodium acetate, pH 5.5), and then the anti-IL17 A/F antibody was eluted from the column with a conductivity gradient created with 40 and 400 mM sodium acetate, pH 5.5. Pooling was based on A280 and was initiated at ≥0.5 OD and ended at ≤2.0 OD during the gradient elution phase.

The third and final hydrophobic interaction chromatography step used PHENYL SEPHAROSE™ 6 Fast Flow (High Sub) resin and was operated in a flow-through mode. After column equilibration (50 mM sodium acetate pH 5.5), the anti-IL17 A/F pool from the POROS® 50HS column was loaded directly on the column without pH adjustment. The anti-IL17 A/F MAb flowed through. Anti-IL17 A/F MAb pooling was based on A280 and was initiated during the load phase at ≥0.5 OD. The column was washed with 10 CVs of equilibration buffer (50 mM sodium acetate, pH 5.5) and pooling ended during this wash phase at ≤1.0 OD.

The results of using the above process during one purification run are shown in Table 10 below.

TABLE 10

PLBL2 Levels at Various Stages of Purification of Anti-IL17 A/F MAb Using HIC.

| In-Process Sample | PLBL2 (ng/mg by ELISA) Run No. 1 |
|---|---|
| HCCF | 713 |
| MABSELECT SURE ™ Pool | 151 |
| POROS ® 50HS Pool | 47 |
| HIC Pool (100 g/L load density) | <0.7 |

The results shown in Table 10 demonstrate that use of a HIC resin as a final chromatography step effectively reduced residual PLBL2 levels in the anti-IL17 A/F MAb (IgG1) preparation to an amount similar to that seen for the anti-IL13 and anti-ABeta MAbs (IgG4).

Anti-CMV Antibody

In addition to testing anti-IL17 A/F, we tested another IgG1 MAb, anti-CMV-MSL antibody, which is also produced in CHO cells. Exemplary anti-CMV antibodies, including anti-CMV-MSL, and methods of producing such antibodies have been described previously, for example, in WO 2012047732.

Again, we found that a three column process, Protein A affinity chromatography (MABSELECT SURE™), followed by cation exchange chromatography (POROS® 50HS) operated in bind-and-elute mode, and HIC (PHENYL SEPHAROSE™ 6 Fast Flow (high sub)) operated in flow-through mode was convenient and effective for reducing PLBL2 in the final drug substance. This three-column process is described in detail below.

The first affinity chromatography step was a bind-and-elute process using MABSELECT SURE™ resin similar to that described above for the anti-IL13, anti-Abeta and anti-IL17 A/F MAbs. The second cation exchange chromatography step that used POROS® 50HS resin and was operated in bind-and-elute mode. After column equilibration (40 mM sodium acetate, pH 5.5), the pH-adjusted aCMV-MSL MABSELECT SURE™ pool (pH 5.0) was loaded onto the column. The column was washed (40 mM sodium acetate, pH 5.5), and then the aCMV-MSL antibody was eluted from the column with a conductivity gradient created with 40 and 400 mM sodium acetate, pH 5.5. Pooling was based on A280 and was initiated at ≥0.5 OD and ended at ≤1.0 OD during the gradient elution phase.

In this particular run, a viral filtration step was performed in between the cation exchange and hydrophobic interaction chromatography steps using Viresolve Pro as the virus filter and Fluorodyne UEDF filter as the pre-filter.

The third and final hydrophobic interaction chromatography step used PHENYL SEPHAROSE™ 6 Fast Flow (High Sub) resin and was operated in a flow-through mode. After column equilibration (50 mM sodium acetate pH 5.5), the anti-CMV-MSL pool from the POROS® 50HS column was loaded directly on the column without pH adjustment. The anti-CMV-MSL MAb flowed through. Anti-CMV-MSL MAb pooling was based on A280 and was initiated during the load phase at ≥0.5 OD. The column was washed with 10 CVs of equilibration buffer (50 mM sodium acetate, pH 5.5) and pooling ended during this wash phase at ≤0.5 OD.

The results of using the above process during one purification run is shown in Table 11 below.

TABLE 11

PLBL2 Levels at Various Stages of Purification of Anti-CMV-MSL MAb Using HIC.

| In-Process Sample | PLBL2 (ng/mg by ELISA) Run No. 1 |
|---|---|
| HCCF | 2608 |
| MABSELECT SURE ™ Pool | 319 |
| POROS ® 50HS Pool | 33 |
| Viresolve Pro Pool | 32 |
| HIC Pool (60 g/L load density) | <0.6 |

The results shown in Table 11 demonstrate that use of a HIC resin as a final chromatography step effectively reduced residual PLBL2 levels in the anti-CMV-MSL MAb preparation to an amount similar to that seen for the anti-IL13, anti-ABeta, and anti-IL17 A/F MAbs. Accordingly, use of a HIC resin as a final chromatography step in the purification of CHO-produced polypeptides, such as the anti-IL13 MAb and other MAbs described herein, effectively reduced the residual amount of hamster PLBL2 to very low levels, e.g., less than 1 ng/mg in the HIC pool. Thus, we showed that use of the HIC chromatography step as described herein for reducing PLBL2 levels was as effective for IgG1 MAbs as for IgG4 MAbs, illustrating the general applicability of this method for reducing hamster PLBL2 levels in recombinant polypeptide preparations.

Example 3—Assessment of Human Anti-Hamster PLBL2 Response in Patients Administered Anti-IL13 MAb Compositions Containing Varying Amounts of Hamster PLBL2

To assess the potential impact of the CHO PLBL2 impurity, we developed an ELISA assay (a bridging ELISA assay) to detect antibodies to hamster PLBL2 in human subjects who had received the anti-IL13 MAb, lebrikizumab. Serum samples from patients who participated in various clinical studies of lebrikizumab were analyzed for evidence of anti-hamster PLBL2 antibodies pre-dose and post-dose as well as in subjects who received placebo. The details of the clinical studies have been described previously (WO 2012/083132, Corren et al., N Engl J Med 365:1088-98 (2011)) and only the most relevant details of these studies are provided below.

The antibody bridging ELISA assay that was developed and validated to detect antibodies to hamster PLBL2 in human serum used two conjugated reagents to capture all isotypes of antibodies directed against hamster PLBL2: purified hamster PLBL2 conjugated to biotin (Biotin-PLBL2) and purified hamster PLBL2 conjugated to digoxigenin (DIG-PLBL2). Production and purification of hamster PLBL2 was carried out using standard methods known to one skilled in the art is also described in U.S. Provisional Application Nos. 61/877,503 and 61/991,228 and conjugation to biotin or DIG were carried out using standard methods known to one skilled in the art. In this semi-homogenous antibody bridging ELISA assay, 75 µL/well of conjugated solution in assay diluent (PBS/0.5% BSA/0.05% Polysorbate 20/0.05% ProClin 300, pH 7.4±0.1) containing 3 µg/mL of each Biotin-PLBL2 and DIG-PLBL2 were co-incubated overnight (16-24 hours) at ambient temperature with 75 µL/well of 1:20 diluted serum samples and controls in assay diluent in polypropylene micronic tubes (National Scientific Supply Co.; Claremont, Calif.). After incubation, 100 µL/well of mixture from the micronic tubes were transferred to a streptavidin-coated 96-well microplate (StreptaWell™ High Bind; Roche Diagnostics; Indianapolis, Ind.) that was washed 3 times with 400 µL/well of wash buffer (PBS/0.05% Polysorbate 20) in an automatic plate washer (BioTek ELx405) and incubated at ambient temperature for 2 hours±10 minutes. The plate was washed 4 times with 400 µL/well of wash buffer in the plate washer, Subsequently, 100 µL/well of 400 ng/mL mouse anti-digoxin antibody conjugated with horseradish peroxidase (HRP) (Jackson ImmunoResearch Cat.200-032-156) was added and incubated at ambient temperature for 2 hours±10 minutes for detection. After the plate was washed 4 times with 400 µL/well of wash buffer in the plate washer, 100 µL/well of equal mixture solution of peroxidase substrate (tetramethyl benzidine) (0.4 g/L TMB) and Peroxidase Solution B (0.02% hydrogen peroxide) (KPL Cat. 50-76-03) was added and incubated at ambient temperature for 18-28 minutes for color development and the reaction was stopped by adding 100 µL/well of 1 M phosphoric acid. The plates were read at 450 nm for detection absorbance and 630 nm for reference absorbance. The positive control for the assay was a monoclonal antibody construct consisting of a murine anti-hamster PLBL2-specific complementarity determining region (CDR) on a human IgG1 framework. The relative sensitivity of the assay using this antibody was determined to be 25 ng/mL. Assay drug tolerance experiments using this antibody demonstrated that up to 50 µg/mL of lebrikizumab or 1 µg/mL of hamster PLBL2 in serum did not cause interference or cross-reactivity in the assay.

To carry out the assay, serum samples were first screened in the assay at a minimum dilution of 1/20. Samples that screened positive were then confirmed for hamster PLBL2 specificity using a competition confirmatory assay. If the sample was confirmed as positive, it was serially diluted to obtain a titer value. Positive responses were reported in titer units, which is the log 10 of the dilution factor at which the sample signal was equal to the signal of the assay cutpoint (threshold for determining positivity).

The four clinical studies in which patient samples were analyzed using the anti-hamster PLBL2 ELISA described above are briefly described as follows. Study 1 was a Phase II randomized, double-blind, placebo-controlled, proof-of-concept study to evaluate the effects of lebrikizumab in patients with asthma whose disease was inadequately controlled during chronic therapy with inhaled corticosteroids (ICS). A total of 219 patients were randomized, with 106 receiving at least one 250 mg subcutaneous (SC) dose of lebrikizumab and 92 receiving six monthly doses.

Study 2 was a Phase II randomized, double-blind, placebo-controlled, dose-ranging study in patients with asthma who were not on ICS therapy. Patients received one of three doses (500, 250, or 125 mg) of lebrikizumab or placebo via SC administration. Study drug was administered four times during the 12-week treatment period. A total of 158 patients were exposed to at least one dose of lebrikizumab, and 145 patients received all four doses.

Study 3 was a Phase I PK study of lebrikizumab in healthy Japanese and Caucasian volunteers. Three discrete cohorts of 20 healthy Japanese and Caucasian subjects (10 subjects in each racial group) were randomized between lebrikizumab (125, 250, and 375 mg SC) and placebo in a 7:3 ratio. Subjects were dosed once on Day 1 and were subsequently monitored for 120 days. A total of 42 subjects each received one dose of lebrikizumab.

In Studies 1-3, a total of 306 subjects, 264 of which were asthma patients, each received at least one dose of material containing hamster PLBL2. Exposure to hamster PLBL2 was variable, depending on the dose of lebrikizumab received.

Study 4 was a Phase IIb randomized, double-blind, placebo-controlled studies to assess the efficacy and safety of lebrikizumab in patients with uncontrolled asthma who were using ICS and a second controller medication. Patients received one of three doses (250, 125, or 37.5 mg) of lebrikizumab or placebo via SC administration monthly. In Study 4, a total of 463 patients were randomized, with 347 receiving at least one dose of lebrikizumab. Exposure to hamster PLBL2 was variable, depending on the dose of lebrikizumab received.

Table 12 below provides a summary of each of the Studies 1-4 showing the range of hamster PLBL2 levels the subjects were exposed to and the dose of lebrikizumab.

TABLE 12

Hamster PLBL2 Exposure in Lebrikizumab Clinical Trials.

| Study | Drug Substance PLBL2 (ng/mg) | Lebrikizumab Dose (mg/month) | PLBL2 (μg/dose) |
|---|---|---|---|
| 1 | 34-137[a] | 250 | 9-34 |
| 2 | 34-137[a] | 125 | 4-17 |
|   |   | 250 | 9-34 |
|   |   | 500 | 17-69 |
| 3 | 34 | 125 | 4 |
|   |   | 250 | 9 |
|   |   | 375 | 13 |
| 4 | 242 | 37.5 | 9 |
|   | 328 | 125 | 41 |
|   | 328 | 250 | 82 |

[a]Range from four different lots of clinical material.

A retrospective analysis of selected time points from Study 1 was performed using the anti-hamster PLBL2 antibody assay described above to detect antibodies to hamster PLBL2. Samples from both placebo and dosed subjects were analyzed to determine the level of pre-existing response as well as the development of antibodies in response to lebrikizumab dosing. There were 113 placebo subjects and 106 dosed subjects who received at least one dose of lebrikizumab. Timepoints selected for analysis were Days 0, 29, 85, 141, 225, and early termination. Samples were taken prior to the next dose; therefore, Day 29 samples were taken prior to the administration of the second dose. The percentage of anti-hamster PLBL2 antibody-positive subjects at each timepoint was calculated by taking the number of positive subjects at each timepoint and dividing by the total number of subjects tested at each timepoint. The data is shown in Table 13.

TABLE 13

Anti-Hamster PLBL2 Antibody Results for Study 1.

% Positive at Each Timepoint
(no. positive subjects/total no. subjects evaluable)
Study Day:

|  | 0 | 29 | 85 | 141 | 225 | Early Termination |
|---|---|---|---|---|---|---|
| Placebo | 6 (7/110) | 7 (8/107) | 9 (9/104) | 8 (8/99) | 5 (5/97) | 25 (2/8) |
| 250 mg dose | 5 (5/102) | 6 (6/100) | 89 (90/101) | 98 (92/94) | 98 (91/93) | 100 (8/8)[a] |

[a]Of the 8 lebrikizumab subjects who discontinued study drug early, only 3 reported adverse events as the reason for study drug discontinuation.

The 6 Study 1 placebo subjects who were positive pre-dose on Day 0 continued to be positive throughout the study. Samples from these subjects were confirmed as positive in a confirmatory competition assay and had titers on Day 0 that ranged from 1.6 to 2.9 titer units. Titers obtained on subsequent visits were similar to those obtained on Day 0. A few additional placebo subjects had low-level positive responses during the Study.

Among the Study 1 subjects that received lebrikizumab, 98% (104/106) had a positive antibody response after dosing and remained positive through the end of the study, with most subjects becoming positive after receiving at least two doses of lebrikizumab. Titers after dosing ranged from 1.35 to 4.76 titer units, with titers generally increasing over time. The clinical significance of the development of anti-hamster PLBL2 antibodies is not known. No clinically important safety signals were identified in this study and, given the high incidence of antibodies to hamster PLBL2, no correlation with safety events could be made.

An interim analysis was also performed on samples collected in Study 4. Samples from both placebo and dosed subjects were analyzed to determine the level of pre-existing response as well as the development of anti-hamster PLBL2 antibodies in response to lebrikizumab dosing. There were 116 placebo subjects and 347 dosed subjects who received at least one dose of lebrikizumab. Samples from 92 placebo subjects and 268 dosed subjects are represented in this data set. The results are shown in Table 14.

TABLE 14

Anti-Hamster PLBL2 Antibody Results for Study 4 for Subjects not Previously Exposed to Lebrikizumab.

% Positive at Each Timepoint
(no. positive subjects/total no. subjects evaluable)
Study Day:

|  | 0 | 29 | 85 | 169 | 253 | Early Termination |
|---|---|---|---|---|---|---|
| Placebo | 4 (4/89) | 4 (3/78) | 4 (2/48) | 0 (0/13) | NA | 0 (0/5) |
| 37.5 mg dose | 9 (8/88) | 9 (7/82) | 55 (35/64) | 79 (27/34) | 66 (2/3) | 43 (3/7)[a] |
| 125 mg dose | 4 (3/81) | 11 (8/73) | 87 (48/55) | 100 (9/9) | NA | 0 (0/2)[a] |
| 250 mg dose | 5 (4/88) | 10 (7/72) | 96 (49/51) | 100 (13/13) | NA | 67 (2/3)[a] |

[a]Of the 12 lebrikizumab subjects who discontinued study drug early, only 4 reported adverse events as the reason for study drug discontinuation.

The four Study 4 placebo subjects that were positive pre-dose on Day 0 had low-level positive responses that were just above the detection limit of the assay. The low-level responses were detectable at some, but not all, subsequent timepoints.

The 15 Study 4 subjects receiving lebrikizumab that were positive pre-dose on Day 0 continued to be positive at subsequent timepoints, with increasing titers after multiple doses. In addition, there were 10 subjects in Study 4 who previously received lebrikizumab in Study 1. Nine of these subjects were subsequently re-dosed with lebrikizumab in Study 4 while 1 subject received placebo. All 10 subjects were pre-dose positive on Day 0 for Study 4 and continued to be positive at subsequent timepoints. The data from these 10 subjects were excluded from Table 14 due to their previous lebrikizumab exposure.

Among the Study 4 subjects receiving lebrikizumab, there appear to be differences in positivity rates between dose groups. However, as these data are incomplete, conclusions regarding the significance of these differences cannot be made at this time. Similar to the data from Study 1, the majority of subjects become positive after receiving at least two doses of lebrikizumab. Titers after dosing ranged from 1.68 to 4.55 titer units, with titers generally increasing over time. Since this is an incomplete data set, positive percentages and titer ranges may change as additional data are accumulated.

An interim safety assessment of Study 4 showed a safety profile similar those of the earlier completed studies with no clinically significant safety signals, including no reports of anaphylaxis or serious hypersensitivity reactions. Of note, 6 of the 9 patients who received lebrikizumab in Study 1 and were subsequently re-dosed with lebrikizumab in Study 4 had not reported any adverse events at the time of the interim analysis and only 1 patient reported any local injection-site reactions. No clinical sequelae of this anti-hamster PLBL2 antibody response have been identified in the clinical trials to date.

We also performed an assessment on the 125-mg dose group from Study 2 and those results are shown in Table 15.

TABLE 15

Anti-Hamster PLBL2 Antibody Results for Study 2.

| | % Positive at Each Timepoint (no. positive subjects/total no. subjects evaluable) Study Day: | | | | | |
|---|---|---|---|---|---|---|
| | 0 | 29 | 57 | 85 | 141 | Early Termination |
| 125 mg dose | 4 (2/51) | 21 (11/53) | 70 (35/50) | 88 (45/51) | 86 (43/50) | 100 (2/2)[a] |

[a] Of the 2 subjects who discontinued study drug early, neither reported adverse events as the reason for study drug discontinuation.

The two Study 2 subjects that were positive pre-dose on Day 0 continued to be positive at all subsequent timepoints, with increasing titers after multiple doses. Among the Study 2 subjects that received 125 mg of lebrikizumab, 87% (46/53) had a positive antibody response after dosing and remained positive through the end of the study, with most subjects becoming positive after receiving at least two doses of lebrikizumab. Titers after dosing ranged from 1.51 to 4.09 titer units, with titers generally increasing over time.

CONCLUSIONS

To assess the potential impact of the CHO PLBL2 impurity, an assay was developed to detect antibodies to hamster PLBL2 in subjects who had received lebrikizumab preparations that contained significant levels of hamster PLBL2. On the basis of the completed data sets from Study 1 and the 125 mg dose group of Study 2 and on the partial data set from Study 4, the presence of hamster PLBL2 in lebrikizumab preparations produced immune responses in most subjects exposed to hamster PLBL2.

A number of subjects in both the placebo and lebrikizumab dose groups had pre-existing immunoreactivity in the anti-hamster PLBL2 antibody assay. The cause of this pre-existing response is unknown; antibody reactivity to CHO host cell proteins has previously been characterized and confirmed in normal human serum samples with no known prior exposure to CHO-derived biological products (Xue et al., The AAPS Journal 12(1):98-106 (2010)). However, there are no published data specific to the single species of CHOP, PLBL2.

For subjects with pre-existing immunoreactivity in the anti-hamster PLBL2 antibody assay at the start of the study, there was a sustained rise in antibody titers after repeat administration with lebrikizumab. For subjects that were antibody negative at the start of the study, the majority of subjects across all four studies became positive after at least two administrations of lebrikizumab and remained positive through all subsequent timepoints.

The clinical significance of the development of anti-hamster PLBL2 antibodies is not known. Although there was a high incidence of antibodies to hamster PLBL2 in the study subjects, no correlation between safety events could be made. Importantly, there were no safety signals identified in these completed or interim studies and in particular, no reported events of anaphylaxis, anaphylactoid, or serious hypersensitivity reactions. Nevertheless, there remains a concern that long term exposure with repeat dosing could increase the potential for undesirable effects such as anaphylaxis, hypersensitivity, and immune complex deposition, particularly in asthma patient populations and other allergic or hypersensitive patient populations. Accordingly, it is important to dose patients in late stage clinical studies and beyond, where there may be such repeat dosing over a long period of time, with anti-IL13 MAb (e.g., lebrikizumab) preparations containing substantially reduced levels of hamster PLBL2 so as to minimize immunogenicity as much as possible.

Additional antibody sequences are provided in Table 16 below.

TABLE 16

Anti-IL17 A/F antibody amino acid sequences (SEQ ID NOS.: 15-22) and anti-Abeta antibody amino acid sequences (SEQ ID NOS.: 23-30).

| | |
|---|---|
| CDR-H1 (SEQ ID NO.: 15) | Asp Tyr Ala Met His |
| CDR-H2 (SEQ ID NO.: 16) | Gly Ile Asn Trp Ser Ser Gly Gly Ile Gly Tyr Ala Asp Ser Val Lys Gly |
| CDR-H3 (SEQ ID NO.: 17) | Asp Ile Gly Gly Phe Gly Glu Phe Tyr Trp Asn Phe Gly Leu |
| CDR-L1 (SEQ ID NO.: 18) | Arg Ala Ser Gln Ser Val Arg Ser Tyr Leu Ala |
| CDR-L2 (SEQ ID NO.: 19) | Asp Ala Ser Asn Arg Ala Thr |
| CDR-L3 (SEQ ID NO.: 20) | Gln Gln Arg Ser Asn Trp Pro Pro Ala Thr |
| VH (SEQ ID NO.: 21) | Glu Val Gln Leu Val Glu Ser Gly Gly Gly Leu Val Gln Pro Gly Arg Ser Leu Arg Leu Ser Cys Ala Ala Ser Gly Phe Thr Phe Asp Asp Tyr Ala Met His Trp Val Arg Gln Ala Pro Gly Lys Gly Leu Glu Trp Val |

TABLE 16-continued

Anti-IL17 A/F antibody amino acid sequences (SEQ ID NOS.: 15-22) and anti-Abeta antibody amino acid sequences (SEQ ID NOS.: 23-30).

| | |
|---|---|
| | Ser Gly Ile Asn Trp Ser Ser Gly Gly Ile Gly Tyr Ala Asp Ser Val<br>Lys Gly Arg Phe Thr Ile Ser Arg Asp Asn Ala Lys Asn Ser Leu Tyr<br>Leu Gln Met Asn Ser Leu Arg Ala Glu Asp Thr Ala Leu Tyr Tyr Cys<br>Ala Arg Asp Ile Gly Gly Phe Gly Glu Phe Tyr Trp Asn Phe Gly Leu<br>Trp Gly Arg Gly Thr Leu Val Thr Val Ser Ser |
| VL<br>(SEQ ID<br>NO.: 22) | Glu Ile Val Leu Thr Gln Ser Pro Ala Thr Leu Ser Leu Ser Pro Gly<br>Glu Arg Ala Thr Leu Ser Cys Arg Ala Ser Gln Ser Val Arg Ser Tyr<br>Leu Ala Trp Tyr Gln Gln Lys Pro Gly Gln Ala Pro Arg Leu Leu Ile<br>Tyr Asp Ala Ser Asn Arg Ala Thr Gly Ile Pro Ala Arg Phe Ser Gly<br>Ser Gly Ser Gly Thr Asp Phe Thr Leu Thr Ile Ser Ser Leu Glu Pro<br>Glu Asp Phe Ala Val Tyr Tyr Cys Gln Gln Arg Ser Asn Trp Pro Pro<br>Ala Thr Phe Gly Gly Gly Thr Lys Val Glu Ile Lys |
| CDR-H1<br>(SEQ ID<br>NO.: 23) | GFTFSSYGMS |
| CDR-H2<br>SEQ ID<br>NO.: 24) | SINSNGGSTY YPDSVK |
| CDR-H3<br>SEQ ID<br>NO.: 25) | GDY |
| CDR-L1<br>(SEQ ID<br>NO.: 26) | RSSQSLVYSN GDTYLH |
| CDR-L2<br>(SD) ID<br>NO: 27) | KVSNRFS |
| CDR-L3<br>(SEQ ID<br>NO: 28) | SQSTHVPWT |
| VH<br>(SEQ ID<br>NO: 29) | EVQLVESGGG LVQPGGSLRL SCAASGFTFS SYGMSWVRQA PGKGLELVAS INSNGGSTYY<br>PDSVKGRFTI SRDNAKNSLY LQMNSLRAED TAVYYCASGD YWGQGTTVTV SSASTKGPSV<br>FPLAPCSRST SESTAALGCL VKDYFPEPVT VSWNSGALTS GVHTFPAVLQ SSGLYSLSSV<br>VTVPSSSLGT KTYTCNVDHK PSNTKVDKRV ESKYGPPCPP CPAPEFLGGP SVFLFPPKPK<br>DTLMISRTPE VTCVVVDVSQ EDPEVQFNWY VDGVEVHNAK TKPREEQFNS TYRVVSVLTV<br>LHQDWLNGKE YKCKVSNKGL PSSIEKTISK AKGQPREPQV YTLPPSQEEM TKNQVSLTCL<br>VKGFYPSDIA VEWESNGQPE NNYKTTPPVL DSDGSFFLYS RLTVDKSRWQ EGNVFSCSVM<br>HEALHNHYTQ KSLSLSLG |
| VL<br>(SEQ ID<br>NO: 30) | DIVMTQSPLS LPVTPGEPAS ISCRSSQSLV YSNGDTYLHW YLQKPGQSPQ LLIYKVSNRF<br>SGVPDRFSGS GSGTDFTLKI SRVEAEDVGV YYCSQSTHVP WTFGQGTKVE IKRTVAAPSV<br>FIFPPSDEQL KSGTASVVCL LNNFYPREAK VQWKVDNALQ SGNSQESVTE QDSKDSTYSL<br>SSTLTLSKAD YEKHKVYACE VTHQGLSSPV TKSFNRGEC |

---

What is claimed is:

1. A composition comprising an anti-IL13 monoclonal antibody purified from Chinese hamster ovary host cells, wherein the composition comprises the anti-IL13 antibody and a residual amount of hamster phospholipase B-like 2 (PLBL2), wherein the residual amount of hamster PLBL2 is less than 20 ng/mg, wherein the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6.

2. The composition of claim 1, wherein the anti-IL13 antibody comprises a heavy chain variable region having the amino acid sequence of SEQ ID NO.: 7.

3. The composition of claim 1, wherein the anti-IL13 antibody comprises a light chain variable region having the amino acid sequence of SEQ ID NO.: 9.

4. The composition of claim 2, wherein the anti-IL13 antibody comprises a heavy chain having the amino acid sequence of SEQ ID NO.: 10.

5. The composition of claim 3, wherein the anti-IL13 antibody comprises a light chain having the amino acid sequence of SEQ ID NO.: 14.

6. The composition of claim 1, wherein the anti-IL13 antibody comprises a heavy chain variable region having the amino acid sequence of SEQ ID NO.: 7 and a light chain variable region having the amino acid sequence of SEQ ID NO.: 9.

7. The composition of claim 6, wherein the anti-IL13 antibody comprises a heavy chain having the amino acid sequence of SEQ ID NO.: 10 and a light chain having the amino acid sequence of SEQ ID NO.: 14.

8. The composition of claim 1, wherein the amount of hamster PLBL2 was quantified using an immunoassay or a mass spectrometry assay.

9. The composition of claim 8, wherein the immunoassay is a total Chinese hamster ovary protein ELISA or a hamster PLBL2 ELISA.

10. The composition of claim 8, wherein the mass spectrometry assay is LC-MS/MS.

11. A purified anti-IL13 monoclonal antibody preparation isolated from Chinese hamster ovary host cells, wherein the preparation is purified by a process comprising a hydrophobic interaction chromatography (HIC) step thereby producing a purified preparation, wherein the purified preparation comprises the anti-IL13 antibody and a residual amount of hamster PLBL2, wherein the residual amount of hamster PLBL2 is less than 20 ng/mg, wherein the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6.

12. The anti-IL13 antibody preparation of claim 11, wherein the HIC step comprises PHENYL SEPHAROSE™ 6 Fast Flow (High Sub) resin.

13. The anti-IL13 antibody preparation of claim 12, wherein the HIC step comprises operating a PHENYL SEPHAROSE™ 6 Fast Flow (High Sub) resin-containing column in flow-through mode.

14. The anti-IL13 antibody preparation of claim 13, wherein the HIC step comprises an equilibration buffer and a wash buffer, wherein each of the equilibration buffer and the wash buffer comprise 50 mM sodium acetate pH 5.0.

15. The anti-IL13 antibody preparation of claim 14, wherein the flow-through is monitored by absorbance at 280 nanometers and the flow-through is collected between 0.5 OD to 1.5 OD.

16. The anti-IL13 antibody preparation of claim 14, wherein the flow-through is collected for a maximum of 8 column volumes.

17. The anti-IL13 antibody preparation of claim 11, wherein the process further comprises an affinity chromatography step and/or an ion exchange chromatography step.

18. The anti-IL13 antibody preparation of claim 17, wherein the affinity chromatography is protein A chromatography.

19. The anti-IL13 antibody preparation of claim 17, wherein the ion exchange chromatography is anion exchange chromatography.

20. A purified anti-IL13 monoclonal antibody preparation isolated from Chinese hamster ovary cells, wherein the antibody preparation is purified by a process comprising a first Protein A affinity chromatography step, a second anion exchange chromatography step, and a third hydrophobic interaction chromatography (HIC) step thereby producing a purified preparation, wherein the purified preparation comprises the anti-IL13 antibody and a residual amount of hamster PLBL2, wherein the amount of hamster PLBL2 is less than 20 ng/mg, wherein the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6.

21. The anti-IL13 antibody preparation of claim 20, wherein the affinity chromatography step comprises MAB-SELECT SURE™ resin, the anion exchange chromatography step comprises Q SEPHAROSE™ Fast Flow resin, and the HIC step comprises PHENYL SEPHAROSE™ 6 Fast Flow (high sub) resin.

22. The anti-IL13 antibody preparation of claim 21, wherein:
the affinity chromatography step comprises operating a MABSELECT SURE™ resin-containing column in bind-elute mode;
the anion exchange chromatography step comprises operating a Q SEPHAROSE™ Fast Flow resin-containing column in bind-elute mode; and
the HIC step comprises operating a PHENYL SEPHAROSE™ 6 Fast Flow (High Sub) resin-containing column in flow-through mode.

23. The composition of claim 1, wherein the residual amount of hamster PLBL2 is less than 15 ng/mg.

24. The composition of claim 1, wherein the residual amount of hamster PLBL2 is less than 10 ng/mg.

25. The composition of claim 1, wherein the residual amount of hamster PLBL2 is less than 8 ng/mg.

26. The composition of claim 1, wherein the residual amount of hamster PLBL2 is less than 5 ng/mg.

27. The composition of claim 1, wherein the residual amount of hamster PLBL2 is less than 3 ng/mg.

28. The composition of claim 1, wherein the residual amount of hamster PLBL2 is less than 2 ng/mg.

29. The composition of claim 1, wherein the residual amount of hamster PLBL2 is less than 1 ng/mg.

30. The composition of claim 1, wherein the residual amount of hamster PLBL2 is less than 0.5 ng/mg.

31. The purified anti-IL13 monoclonal antibody preparation of claim 11, wherein the anti-IL13 antibody comprises a heavy chain variable region having the amino acid sequence of SEQ ID NO.: 7 and a light chain variable region having the amino acid sequence of SEQ ID NO.: 9.

32. The purified anti-IL13 monoclonal antibody preparation of claim 11, wherein the anti-IL13 antibody comprises a heavy chain having the amino acid sequence of SEQ ID NO.: 10 and a light chain having the amino acid sequence of SEQ ID NO.: 14.

33. The purified anti-IL13 monoclonal antibody preparation of claim 11, wherein the residual amount of hamster PLBL2 is less than 5 ng/mg.

34. The purified anti-IL13 monoclonal antibody preparation of claim 20, wherein the anti-IL13 antibody comprises a heavy chain variable region having the amino acid sequence of SEQ ID NO.: 7 and a light chain variable region having the amino acid sequence of SEQ ID NO.: 9.

35. The purified anti-IL13 monoclonal antibody preparation of claim 20, wherein the anti-IL13 antibody comprises a heavy chain having the amino acid sequence of SEQ ID NO.: 10 and a light chain having the amino acid sequence of SEQ ID NO.: 14.

36. The purified anti-IL13 monoclonal antibody preparation of claim 20, wherein the residual amount of hamster PLBL2 is less than 5 ng/mg.

\* \* \* \* \*